United States Patent
Yuan

(10) Patent No.: US 7,192,729 B2
(45) Date of Patent: *Mar. 20, 2007

(54) METHODS FOR ASSAYING HOMOCYSTEINE

(75) Inventor: Chong-Sheng Yuan, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/043,787

(22) Filed: Jan. 10, 2002

(65) Prior Publication Data

US 2006/0246529 A1 Nov. 2, 2006

Related U.S. Application Data

(63) Continuation-in-part of application No. 09/457,205, filed on Dec. 6, 1999, now abandoned, which is a continuation-in-part of application No. 09/347,878, filed on Jul. 6, 1999, now Pat. No. 6,376,210.

(60) Provisional application No. 60/301,895, filed on Jun. 29, 2001.

(51) Int. Cl.
   *C12Q 1/34* (2006.01)
   *G01N 33/53* (2006.01)
   *G01N 33/52* (2006.01)
   *C12N 9/14* (2006.01)

(52) U.S. Cl. .......... 435/18; 435/7.1; 435/7.6; 435/7.72; 435/7.8; 435/7.9

(58) Field of Classification Search .......... 435/195, 435/18, 174, 7.1; 436/86, 68, 71, 161; 530/350
See application file for complete search history.

(56) References Cited

U.S. PATENT DOCUMENTS

| | | | |
|---|---|---|---|
| 3,464,890 A | 9/1969 | Weichselbaum | 195/66 |
| 3,647,070 A | 3/1972 | Adler | 210/83 |
| 3,780,935 A | 12/1973 | Lucacs et al. | 233/1 A |
| 3,852,194 A | 12/1974 | Zine et al. | 210/83 |
| 4,140,631 A | 2/1979 | Okuda et al. | 210/83 |
| 4,161,425 A | 7/1979 | Perry | 435/11 |
| 4,164,448 A | 8/1979 | Roeschlau et al. | 435/11 |
| 4,175,183 A | 11/1979 | Ayers | 536/57 |
| 4,177,038 A | 12/1979 | Biebricher et al. | 8/192 |
| 4,188,188 A | 2/1980 | Wilner et al. | 23/230 |
| 4,211,531 A | 7/1980 | Das | 23/230 |
| 4,244,721 A | 1/1981 | Gupta et al. | 65/31 |
| 4,276,280 A | 6/1981 | Akerkar et al. | 424/1 |
| 4,282,287 A | 8/1981 | Giese | 428/407 |
| 4,336,185 A | 6/1982 | Niswender | 260/112 |
| 4,337,339 A | 6/1982 | Farina et al. | 544/257 |
| 4,477,575 A | 10/1984 | Vogel et al. | 436/170 |
| 4,562,157 A | 12/1985 | Lowe et al. | 435/291 |
| 4,681,870 A | 7/1987 | Balint, Jr. et al. | 502/403 |
| 4,795,699 A | 1/1989 | Tabor et al. | 435/5 |
| 4,803,153 A | 2/1989 | Shibata et al. | 435/2 |
| 4,908,405 A | 3/1990 | Bayer et al. | 525/61 |
| 4,954,444 A | 9/1990 | Eveleigh et al. | 435/181 |
| 5,034,332 A | 7/1991 | Rapacz et al. | 436/71 |
| 5,047,327 A | 9/1991 | Caris et al. | 435/11 |
| 5,137,877 A | 8/1992 | Kaneko et al. | 514/25 |
| 5,162,516 A | 11/1992 | Ingram et al. | 536/27 |
| 5,215,899 A | 6/1993 | Dattagupra | 435/6 |
| 5,217,873 A | 6/1993 | Caris et al. | 435/11 |
| 5,342,767 A | 8/1994 | Wong et al. | 435/122 |
| 5,344,777 A | 9/1994 | Tamaki et al. | 435/252.3 |
| 5,349,066 A | 9/1994 | Kaneko et al. | 546/294 |
| 5,356,780 A | 10/1994 | Robinson et al. | 435/7.6 |
| 5,364,533 A | 11/1994 | Ogura et al. | 210/645 |
| 5,374,560 A | 12/1994 | Allen et al. | 436/129 |
| 5,385,833 A | 1/1995 | Bradshaw et al. | 435/156 |
| 5,389,449 A | 2/1995 | Afeyan et al. | 428/523 |
| 5,451,683 A | 9/1995 | Barrett et al. | 548/302.7 |
| 5,523,225 A | 6/1996 | Kraus | 435/240.1 |
| 5,541,098 A | 7/1996 | Caput et al. | 435/191 |
| 5,593,894 A | 1/1997 | Purdie | 436/71 |
| 5,612,474 A | 3/1997 | Patel | 536/27.14 |
| 5,624,836 A | 4/1997 | Lange, III et al. | 435/325 |
| 5,631,127 A | 5/1997 | Sundrehagen | 435/4 |
| 5,665,560 A | 9/1997 | Fujishiro et al. | 435/11 |
| 5,679,548 A | 10/1997 | Barbas et al. | 435/69.6 |
| 5,710,248 A | 1/1998 | Grose | 530/327 |
| 5,728,562 A | 3/1998 | Shigyo | 435/191 |
| 5,800,979 A | 9/1998 | Kolhouse | 435/4 |
| 5,827,645 A | 10/1998 | Sundrehagen | 435/4 |
| 5,834,184 A | 11/1998 | Harada et al. | 435/6 |
| 5,854,023 A * | 12/1998 | Hillman et al. | 435/69.1 |

(Continued)

FOREIGN PATENT DOCUMENTS

DE 197 57 571 6/1999

(Continued)

OTHER PUBLICATIONS

Bork, Genome Research, 10:398-400, 2000.*

(Continued)

*Primary Examiner*—Rebecca E. Prouty
*Assistant Examiner*—Iqbal Chowdhury
(74) *Attorney, Agent, or Firm*—Morrison & Foerster LLP

(57) ABSTRACT

The present invention relates to compositions and methods for assaying homocysteine (Hcy) and thus related moieties, e.g., S-adenosylhomocysteine (SAH) or adenosine. More particularly, assay methods that employ, mutant SAH hydrolase having binding affinity for Hcy, SAH or adenosine but has attenuated catalytic activity, are provided. The modified enzymes and fusion proteins containing the modified enzymes are also provided.

20 Claims, 5 Drawing Sheets

U.S. PATENT DOCUMENTS

| | | | | |
|---|---|---|---|---|
| 5,855,881 | A | 1/1999 | Loike et al. | 424/94.2 |
| 5,879,921 | A | 3/1999 | Cherry et al. | 435/190 |
| 5,885,767 | A | 3/1999 | Rozzell, Jr. | 435/4 |
| 5,891,704 | A | 4/1999 | Yuying | 435/232 |
| 5,908,924 | A | 6/1999 | Burdette et al. | 536/23.2 |
| 5,958,717 | A | 9/1999 | Sundrehagen | 435/18 |
| 6,376,210 | B1 | 4/2002 | Yuan | 435/18 |
| 6,395,256 | B1 | 5/2002 | Osswald et al. | 424/1.69 |

FOREIGN PATENT DOCUMENTS

| | | |
|---|---|---|
| WO | WO 86/03840 | 7/1986 |
| WO | WO 88/08137 | 10/1988 |
| WO | WO 93/15220 | 8/1993 |
| WO | WO 98/20156 | 5/1998 |
| WO | WO 99/34210 | 7/1999 |
| WO | WO 01/02600 | 1/2001 |

OTHER PUBLICATIONS

Seffernick et al., J. Bacteriol. 183(8):2405-2410, 2001.*
Witkowski et al., Biochemistry 38:11643-11650, 1999.*
Yuan et al., Chemical Modification and Site-directed Mutagenesis of Cysteine Residues in Human Placental S-Adenosylhomocysteine hydrolase. J. Biol. Chem.271(45):28009-28016, 1996.*
GenBank Accession No. CAH70965, created on Dec. 1, 2001.*
GenBank Accession No. CAH70966, created on Feb. 1, 2005.*
GenBank Accession No. Q96HN2, created on Feb. 28, 2003.*
Amaratunga, et al. (1996). Biochemistry 35(7):2453-2463.
Araki, et al. (1987). J. Chromatog. 422:43-52.
Adlt-Richie et al., (1994) FASEB Journal 7:A1412.
Ault-Richie, et al. (1994). J. Biol Chem 269:31472-31478.
Bahnson, et al. (1997). Proc. Natl. Acad Sci USA 94(24):12797-12802.
Ballal, et al. (1997). Cleveland Clinic Journal of Medicine 64(10):543-549.
Bartel et al. (1996). Nature Genet 12:72-77.
Basran, et al. (1997). Protein Eng. 10(7):815-826.
Bastin et al. (1996). Mol Biochem Parasitology 77:235-239.
Batra et al. (1993). Molecular Immunol 30;379-386.
Ballal, et al. (1997) Cleveland Journal of Medicine 64(10):543-549.
Bendixen et al. (1994). Nucl Acids Res 22:1778-1779.
Benoist, et al. (1981). Nature 290:304-310.
Benton, W. and Davis, R. (1977). Science 196:180.
Boers, G.H.J. (1997). J Inher Metab Dis 20:301-306.
Bognar, et al. (1987). J Biol Chem 262(25):12337-12343.
Boushey, et al. (1995). JAMA 274:1049-1057.
Brinster, et al. (1982). Nature 296:39-42.
Broach, et al., (1995) Nature 284:14-16.
Buchko, et al. (1999). Biochim Biophys Res Commun 254(1):109-113.
Bunin B. et al. (1994). Proc Natl Acad Sci USA 91:4708-4712.
Burbaum, et al., (1997) Curr. Opin. Chem. Biol. 1:72-78.
Burd and Dreyfuss. (1994). EMBO J 13:1197.
Burd and Dreyfuss. (1994). Science 265:615-621.
Campagna, et al. (1998). J Diary Sci 81(12):3139-3148.
Carreras, et al. (1992). Biochemistry 31(26):6038-6044.
Chen and Katz (1998). Bio Techniques 25(1):22-24.
Chen C., et al. (1994). J Am Chem Soc 116:2661-2662.
Chittenden T. et al. (1991). Cell 65:1073-1082.
Chu, et al. (1996). Ann NY Acad Sci 804:781-786.
Churcher M et al. (1993). J Mol Biol 230:90-110.
Clarke et al. (1991). New Eng J Med 324:1149-1155.
Colas et al. (1996). Nature 380:548-550.
Colby, et al. (1998). Biochemistry 37(26):9295-9304.
Corbin, et al. (1994). Appl Environ Microbiol 60(12):4239-4244.
Cordingley, et al. (1990). J Biol Chem 265:9062.
Cornell and Riscoe. (1998). Biochim Biophys Acta 1396(1):8-14.
Costi, et al. (1996). Biochemistry 35:3944-3949.
Coulter-Karis and Hershfield. (1989). Ann Hum Genet 53(2):169-175.
Creedon, et al., (1994) J. Biol. Chem. 269(23):16364-70.

Cumber et al. (1992). Bioconjugate Chem 3:397-401.
Cwirla et al. (1990). Proc Natl Acad Sci, USA 87:6378-6382.
DeBoer, et al. (1983). Proc. Natl. Acad Sci USA 80:21-25.
Diaz-Arrastia, et al. (1998). Arch Neurol55:1407-1408.
Dicker, et al. (1990). J Biol Chem 265(14):8317-8321.
DiPersio, et al. (1990). J Biol Chem 265(28):16801-16806.
Dixon, et al. (1996). Structure 4(11):1263-1275.
Ducloux, et al. (1998). Nephrol Dial Transplantl 13:2890-2893.
Ehrig et al. (1991). Biochemistry 30(4):1062-1068.
Estoyak et al. (1995). Mol Cell Biol 15:5820-5829.
Fattom et al. (1992). Infection & Immun 60:584-589.
Fernandes, P.B., J. (1997) Biomol. Screening 2:1.
Fikrig, et al. (1990). Science 250:553.
Finer-Moore, et al. (1996). Biochemistry 35(16):5125-5136.
Finer-Moore, et al. (1998). J Mol Biol 276(1):113-129.
Finley, Brent et al, (1994).Proc Natl Acad Sci, USA 91:12980-12984.
Flint, et al., (1997) Proc. Natl. Acad. Sci. 94:1680-1685.
Foody, et al. (1998). Clinical Reviews 8:203-210.
Frederick, et al. (1990). J Biol Chem 265(7):3793-3802.
Garrow. (1996). J Biol Chem 271(37):22831-22838.
Germino et al. (1984). Proc Natl Acad Sci, USA 81:4692.
Gilbert, et al. (1980). Scientific American 242:74-94.
Goldmatcher et al. (1992). Bioconj Chem 3:104-107.
Goyette, et al. (1998). Mamm Genome 9(8):652-656.
Graves, et al. (1992). Biochemistry 31:15-21.
Grunstein and Hogness. (1975). Proc. Natl. Acad Sci USA 72:3961.
Habig, et al (1974). J Biol Chem 249:7130.
Hazum et al. (1981). In Pept., Proc Eur Pept Symp, 16th, Brunfeldt, K (Ed), pp. 105-110.
Henderson, et al., (1992) Mol. Biochem. Parasitol. 53(1-2):169-83.
Hershfield, (1989) Ann. Hum. Genet. 53(2):169-175.
Hinderliter, et al. (1998). Biochim Biophys Acta 1448(2):227-235.
Hori, et al. (1996). Cancer Res 56(9):2116-2122.
Hornberger, et al. (1998). American J of Public Health 88:61-67.
Houghten et al. (1991). Nature 354:84-86.
Hu, et al., (1999) Biochemistry 38(26):8323-33.
Hutchison, et al. (1978). J Biol Chem 253:6551.
Ikuta, et al. (1985). Proc. Natl. Acad Sci USA 82(9):2703-2707.
Ito, et al. (1976). J Biochem (Tokyo) 80)6):1327-1334.
Jacobsen, et al. (1998). Clin Chem 44:2238-2239.
Janzen, et al., (1996) Lab Robotics Automation 8:261-265.
Kaelin, et al (1991). Cell 64:521-532.
Kane, et al. (1996). Anal Biochem 233(2):197-204.
Kaneda, et al. (1990). J Biol Chem 265(33):20277-20284.
Kang, et al. (1997). Virus Res 49(2):147-154.
Kedishvili, et al. (1995). J Biol Chem 279(8):3625-3630.
Kery, et al. (1999). Biochemistry 38(9):2716-2724.
Kim, et al. (1974). Proc. Natl. Acad Sci USA 71(2):4821-4825.
Kolodziej and Young. (1991). Methods Enzymol 194:508-519.
Kolonin and Finley, Jr. (1998). Proc Natl Acad Sci, USA 95(24):14266-14271.
Koranyi, et al. (1992). Diabetes 41(7):807-811.
Kozak. (1991). J Biol Chem 266:19867-19870.
Kunst, et al. (1997). Nature 390(6657):249-256.
Kuo, et al. (1981). J Immunol Methods 43(1):35-47.
Ladurner et al. (1997). J Mol Biol 273:330-337.
Lai, et al. (1997). Mol Cell Biol 17(5):2413-2424.
Lal and Sachs, et al. (1995). Plant Physiol 108(3):1295-1296.
Lam et al. (1991). Nature 354:82-84.
Lee, et al. (1990). J Biol Chem 265(31):19082-19090.
Lester et al. (1996).J Biol Chem 271:9460-9465.
Lieberman et al. (1994). Genes & Dev 8:995-1006.
Lowenadler, et al. (1987). Gene 58:87-97.
Lucas, et al. (1998). J Immunol 161(7):3776-3780.
Lue et al. (1987). Proc Natl Acad Sci, USA 84:8839-8843.
Lundstrom et al. (1990). Biotechnology and Bioengineering 36:1056.
Maeji et al. (1992). J Immunol Met 146:83-90.
Magner, et al. (1981). Proc. Natl. Acad Sci USA 78:1441-1445.
Mansoor, et al. (1992). Anal Biochem 200:218-229.
Maru, et al. (1996). J Biol Chem 271:15353.
Maxam ans Gibert. (1980). Meth Enzymol 65:499-560.

McTigue, et al. (1995). *J Mol Biol* 246:21.
Millian and Garrow. (1998). *Arch Biochem Biophys* 356(1):93-98.
Moghadasian, et al. (1997). *Arch Intern Med* 157:2299-2307.
Muerre, et al. (1989). *Cell* 46:777-783.
Nagai and Thogersen. (1987). *Methods Enzymol* 153:461.
Nagelkerken et al. (1997). *Electrophoresis* 18:2684-2698.
Nilsson, et al. (1985). *EMBO J* 4:1075.
Olah et al. (1994). *Biochem* 33:12800-12806.
Perry, et al. (1974). In: *Hertable disorders of amino acid metabolism*. New York, John Wiley & Sons, pp. 419-451.
Powers, et al (1989). *Biotechnol Bioeng* 33:173.
Pu et al. (1992). *Nucl Acids Res* 20:771-775.
Reason, et al. (1999). *Infection and Immunity* 67(2):994-997.
Refsum, et al. (1985). *Clin Chem* 31:624-628.
Refsum, et al. (1998). *Ann Rev Medicine* 49:31-62.
Reith, et al. (1989). *Proc Natl Acad Sci, USA* 86:4200-4204.
Rudiger et al. (1997). *Bio Techniques* 23(1):96-97.
Saksela and Raivio. (1996). *Biochem J* 315(1):235-239.
Sanger, et al. (1997). *Proc. Natl. Acad Sci USA* 74:5463.
Schiffer, et al. (1995). *Biochemistry* 34(50):16279-16287.
Scott, et al. (1995). In: Homocysteine metabolism: from basic science to clinical medicine, Kluwer Academic Publishers, Boston, pp. 133-136.
SenGupta et al. (1996). *Proc Natl Acad Sci, USA* 93:8496-8501.
Senter, et al. (1985). *Photochem Photobiol* 42:231-237.
Shapira et al. (1983). *Gene* 25:71-82.
Sharma, et al. (1989). *Biochem Biophys Res Commun* 164(2):631-637.
Shilo and Weinberg. (1981). *Proc. Natl. Acad Sci USA* 78:6789-6792.
Smith and Johnson. (1988). *Gene* 7:31-40.
Smith, et al (1992). *Methods: A Companion to Methods in Enz* 4:73-78.
St Johnson, et al. (1992). *Proc Natl Acad Sci, USA* 89:10979-10983.
Stabler, et al. (1988). *J Clin Invest* 81:466-474.
Stagljar et al. (1996). *Bio Techniques* 21:430-432.
Steadman, et al. (1998). *Biochemistry* 37:7089-7095.
Stehouwer, et al. (1999). *Kidney International* 55:308-314.
Stein, et al. (1998). *Arch Intern Med* 158:1301-1306.
Strauss, et al. (1981). *Gene* 13: 75-87.
Strop, et al. (1997). *Protein Sci* 6(12):2504-2511.
Sucholeiki, (1994). *Tetrahedron Lett* 35:7307.
Taylor, et al. (1985). *Nucleic Acids Res* 13:8765-8785.
The, et al. (1989). *Mol Endocrinol* 3(8):1310-1312.
Tolbert and Lameh. (1998). *J Neurochem* 70:113-119.
Toye, et al (1990). *Infecion andt Immunity* 58:3909.

Tseng and Verma. (1996). *Gene* 169:287-288.
Tullius, et al. (1987). *Methods Enzymol* 155:537-558.
Turner, et al. (1998). *Nature Structural Biology* 5:369-376.
Ueland, et al. (1989). *J Lab Clin Med* 114:473-501.
Ueland, et al. (1992). Atherosclerotic Cardiovascular Disease, Hemostasis and Endothelial Function. New York, Marcel Dokker, pp. 183-236.
Ueland, et al. (1993). *Clin Chem* 39:1764-1779.
Vener T. et al. (1996). *BioTechniques* 21:255-259.
Villa-Kamaroff, et al. (1978). *Proc. Natl. Acad Sci USA* 75:3727-3731.
Wagner et al., (1981) Nucleotide Sequence of the thymidine kinase gene of herpes simplex virus type 1, Proc. Natl. Acad. Sci. USA 78:1441-1445.
Wang et al. (1996). *Gene* 169(1):53-58.
Wang et al. (1996). *Genes & Dev* 10:3028-3040.
Watson, et al. (1987). Molecular Biology of the Gene, 4th Edition, The Benjacmin/Cummings Pub. Co., p. 224.
Welhoner et al. (1992). *J Biol Chem* 266:4309-4314.
Williams, et al. (1998). *Biochemistry* 37(20):7096-7102.
Wu, et al. (1989). *Proc. Natl. Acad Sci USA* 86(23):9412-9416.
Xie et al. (1998). *Endocrinology* 139(11):4563-4567.
Xu, et al. (1988). *Genomics* 2(3):209-214.
Yamamoto, et al. (1980). *Cell* 22:787-797.
Yin et al., (2000) "Mechanism-based S-Adenosylhomocystein Hydrolase Inhibitors in the Search for Broad-Spectrum Antiviral Agents" Chapter 2 *In Biomedical Chemistry: Applying Chemical Principles to the Understanding and Treatment of Diseases* (Ed. Torrence) John Wiley & Sons, Inc.
Yuan, et al (1993). *J Biol Chem* 268:17030-17037.
Yuan, et al (1996). *J Biol Chem* 271:28009-28016.
Yue, et al. (1999). *Biochemistry* 38(14):4277-4286.
Zapp et al. (1989). *Nature* 342:714.
IUPAC-IUB Commission of Biochemical Nomenclature, (1972). *Biochem* 11(9):1726.
Glover, D.M., Table of Contents, DNA Cloning: A Practical Approach, IRL Press, Ltd., Oxford, Washington, D.C. vol. 1-2, 1994.
Hu et al., Biochem. (2001) 40:15143-15152.
International Search Report, mailed on Nov. 5, 2003, for PCT patent application No. PCT/US03/00866, filed on Jan. 10, 2003, 7 pages.
Komoto et al., J. Biol. Chem. (2000) 275(41):32147-32156.
Porter et al., J. Biol. Chem. (1992) 267(5):3205-3213.
Takata et al., J. of Biol. Chem. (2002) 277(25):22670-22676.

* cited by examiner

# METHODS FOR ASSAYING HOMOCYSTEINE

The present application is a continuation-in-part of U.S. patent application Ser. No. 09/457,205, filed Dec. 6, 1999, now abandoned, which is a continuation-in-part of U.S. patent application Ser. No. 09/347,878, filed Jul. 6, 1999, (now U.S. Pat. No. 6,376,210). The present application also claims priority benefit of U.S. Provisional Patent Application Ser. No. 60/301,895, filed Jun. 29, 2001. The disclosure of the above-referenced applications is incorporated by reference herein in their entirety.

TECHNICAL FIELD

The present invention relates to compositions and methods for assaying homocysteine (Hcy) and its related moieties, e.g., S-adenosylhomocysteine (SAH) or adenosine. More particularly, assay methods that employ, mutant SAH hydrolase having binding affinity for Hcy, SAH or adenosine but has attenuated catalytic activity, are provided. The modified enzymes and fusion proteins containing the modified enzymes are also provided.

BACKGROUND ART

Homocysteine (Hcy) is a thiol-containing amino acid formed from methionine during S-adenosylmethionine-dependent transmethylation reactions. Intracellular Hcy is remethylated to methionine, or is irreversibly catabolized in a series of reactions to form cysteine. Intracellular Hcy is exported into extracellular fluids such as blood and urine, and circulates mostly in oxidized form, and mainly bound to plasma protein (Refsum, et al., *Annu. Rev. Medicine*, 49:31–62 (1998)). The amount of Hcy in plasma and urine reflects the balance between Hcy production and utilization. This balance may be perturbed by clinical states characterized by genetic disorders of enzymes involved in Hcy transsulfuration and remethylation (e.g., cystathionine β-synthase and $N^{5,10}$-methylenetetrahydrofolate reductase or dietary deficiency of vitamins (e.g., vitamin $B_6$, $B_{12}$ and folate) involved in Hcy metabolism (Baual, et al., *Cleveland Clinic Journal of Medicine*, 64:543–549 (1997)). In addition, plasma Hcy levels may also be perturbed by some medications such as anti-folate drugs (e.g., methotrexate) used for treatments of cancer or arthritis (Foody, et al., *Clinician Reviews*, 8:203–210 (1998)).

Severe cases of homocysteinemia are caused by homozygous defects in genes encoding for enzymes involved in Hcy metabolisms. In such cases, a defect in an enzyme involved in either Hcy remethylation or transsulfuration leads to as much as 50-fold elevations of Hcy in the blood and urine. The classic form of such a disorder, congenital homocysteinemia (Hcyemia), is caused by homozygous defects in the gene encoding cystathionine β-synthase (CBS). These individuals suffer from thromboembolic complications at an early age, which result in stroke, myocardial infarction, renovascular hypertension, intermittent claudication, mesenteric ischemic, and pulmonary embolism. Such patients may also exhibit mental retardation and other abnormalities resembling ectopia lentis and skeletal deformities (Perry T., *Homocysteine: Selected aspects* in Nyham W. L. ed. *Heritable disorders of amino acid metabolism*. New York, John Wiley & Sons, pp. 419–451 (1974)). It is also known that elevated Hcy levels in pregnant women is related to birth defects of children with neurotube closures (Scott, et al., "*The etiology of neural tube defects*" in Graham, I., Refsum, H., Rosenberg, I. H., and Ureland P. M. ed. "*Homocysteine metabolism: from basic science to clinical medicine*" Kluwer Academic Publishers, Boston, pp. 133–136 (1995)). Thus, the diagnostic utility of Hcy determinations has been well documented in these clinical conditions.

It has been demonstrated that even mild or moderately elevated levels of Hcy also increase the risk of atherosclerosis of the coronary, cerebral and peripheral arteries and cardiovascular disease (Boushey, et al., JAMA, 274:1049–1057 (1995)). The prevalence of Hcyemia was shown to be 42%, 28%, and 30% among patients with cerebral vascular disease, peripheral vascular disease and cardiovascular disease, respectively (Moghadasian, et al., *Arch. Intern. Med.*, 157:2299–2307 (1997)). A meta-analysis of 27 clinical studies calculated that each increase of 5 µM in Hcy level increases the risk for coronary artery disease by 60% in men and by 80% in women, which is equivalent to an increase of 20 mg/dl$^{-1}$ (0.5 mmol/dl$^{-1}$) in plasma cholesterol, suggesting that Hcy, as a risk factor, is as strong as cholesterol in the general population. Results from these clinical studies concluded that hyperhomocysteinemia is an emerging new independent risk factor for cardiovascular disease, and may be accountable for half of all cardiovascular patients who do not have any of the established cardiovascular risk factors (e.g., hypertension, hypercholesterolemia, cigarette smoking, diabetes mellitus, marked obesity and physical inactivity).

Mild homocysteinemia is mainly caused by heterozygosity of enzyme defects. A common polymorphism in the gene for methylenetetrahydrofolate reductase appears to influence the sensitivity of homocysteine levels to folic acid deficiency (Boers, et al., *J. Inher. Metab. Dis.*, 20:301–306 (1997)). Moreover, plasma homocysteine levels are also significantly increased in heart and renal transplant patients (Ueland, et al., *J. Lab. Clin. Med.*, 114:473–501 (1989)), Alzheimer patients(Jacobsen, et al., *Clin. Chem.*, 44:2238–2239 (1998)), as well as in patients of non-insulin-dependent diabetes mellitus (Ducloux, et al., *Nephrol. Dial. Transplantl*, 13:2890–2893 (1998)). The accumulating evidence linking elevated homocysteine with cardiovascular disease has prompted the initiation of double-blind, randomized and placebo controlled multicenter clinical trials to demonstrate the efficacy of lowering plasma Hcy in preventing or halting the progress of vascular disease (Diaz-Arrastia, et al., *Arch. Neurol.*, 55:1407–1408 (1998)). Determination of plasma homocysteine levels should be a common clinical practice.

As a risk factor for cardiovascular disease, the determination of total plasma Hcy levels (reduced, oxidized and protein-bound) has been recommended in clinical setting (Hornberger, et al., *American J. of Public Health*, 88:61–67 (1998)). Since 1982, several methods for determining total plasma Hcy have been described (Mansoor, et al., *Anal. BioChem.*, 200:218–229 (1992); Steir, et al., *Arch. Intern. Med.* 158:1301–1306 (1998); Ueland, et al., *Clin. Chem.*, 39:1764–1779 ( ) 1993); and Ueland, et al., "*Plasma homocysteine and cardiovascular disease*" in Francis, R. B. Jr. eds. *Atherosclerotic Cardiovascular Disease, Hemostasis, and Endothelial Function*. New York, Marcel Dokker, pp. 183–236 (1992); see, also, Ueland, et al., "*Plasma homocysteine and cardiovascular disease*" in Francis, R. B. Jr. eds. *Atherosclerotic Cardiovascular Disease, Hemostasis, and Endothelial Function*. New York, Marcel Dokker, pp. 183–236 (1992)). The assay of total Hcy in plasma or serum is complicated by the fact that 70% of plasma Hcy is protein-bound and 20–30% exists as free symmetric or mostly asymmetric mixed disulfides. Free reduced Hcy exists in only trace amounts (Stehouwer, et al., *Kidney International*, 55308–314 (1999)).

Most of the methods require sophisticated chromatographic techniques such as HPLC, capillary gas chromatography, or mass spectrometry (GC/MS) to directly or indirectly (e.g., enzymatic conversion of Hcy to SAH (S-adenosylhomocysteine) by SAH hydrolase followed by HPLC or TLC separation) measure Hcy. Radioenzymatic conversion of Hcy to radiolabeled SAH by SAH hydrolase prior to TLC separation has also been used. In these assays, chromatographic separation, which is often time-consuming and cumbersome to perform, is a common key step of these methods. More particularly, these methods require highly specialized and sophisticated equipment and well-trained analytic specialists. The use of such equipment is generally not well-accepted in routine clinical laboratory practice.

Immunoassays for Hcy that use a monoclonal antibody against SAH (Araki, et al., J Chromatog., 422:43–52 (1987)) are also known. These assays are based upon conversion of Hcy to SAH, which is then detected by a monoclonal antibody. Monoclonal antibody against albumin-bound Hcy has been developed for determination of albumin-bound Hcy (Stabler, et al., *J. Clin. Invest.*, 81:466–474 (1988)), which is the major fraction of total plasma Hcy. Other immunological protocols are also available (see, e.g., U.S. Pat. Nos. 5,631,127, 5,827,645, 5,958,717, 6,063,581 and 5,885,767). Though immunoassays avoid a time-consuming chromatographic separation step and are amenable to automation, production of monoclonal antibody is expensive, somewhat unpredictable, and often requires secondary or even tertiary antibodies for detection.

It is an object herein to provide assays for quantifying and/or detecting homocysteine in body fluids and body tissues.

DISCLOSURE OF THE INVENTION

Assays that employ mutant SAH hydrolase having binding affinity for Hcy, SAH or adenosine but has attenuated catalytic activity are provided. These methods are designated substrate trapping methods; and the modified SAH hydrolases, are designated as "substrate trapping SAH hydrolases." The substrate trapping SAH hydrolases and methods for preparing them are also provided. The assays can be used for prognostic, diagnostic, drug screening or treatment monitoring purposes.

The assays readily can be automated. In addition, the assays can be adapted for use in point of care systems and in home test kits. For example, blood test point of care systems can be adapted for measuring homocysteine levels using the mutant SAH hydrolases provided herein. Home test kits may also be adapted for use with the methods and mutant SAH hydrolases provided herein.

In one aspect, the present invention is directed to a method for assaying homocysteine (Hcy), S-adenosylhomocysteine (SAH) or adenosine in a sample, which method comprises: a) contacting a sample containing or suspected of containing Hcy, SAH or adenosine with a mutant SAH hydrolase, wherein said mutant SAH hydrolase has binding affinity for Hcy, SAH or adenosine but has attenuated catalytic activity, and said binding affinity and/or said attenuated catalytic activity of said SAH hydrolase is caused by a mutation in said mutant SAH hydrolase's catalytic site, its binding site for NAD$^+$, NADH, Hcy, SAH or adenosine, or a combination thereof; and b) detecting binding between Hcy, SAH or adenosine with said mutant SAH hydrolase, whereby the presence or amount of Hcy, SAH or adenosine in said sample is assessed.

Any suitable mutant SAH hydrolases can be used in the present methods. In one example, the mutant SAH hydrolase used in the method has a mutation in an amino acid residue that is directly involved in the SAH hydrolase's catalytic activity, its binding with NAD$^+$, NADH, Hcy, SAH or adenosine. In another example, the mutant SAH hydrolase used in the method has a mutation in an amino acid residue that is adjacent to an amino acid residue that is directly involved in the SAH hydrolase's catalytic activity, its binding with NAD$^+$, NADH, Hcy, SAH or adenosine.

The mutant SAH hydrolase can have enhanced binding affinity for Hcy, SAH or adenosine than a wild type SAH hydrolase from which said mutant SAH hydrolase is derived. Preferably, the mutant SAH hydrolase has at least 10, 20, 30, 40, 50, 60, 70, 80, 90 or 100 fold higher binding affinity for Hcy, SAH or adenosine than a wild type SAH hydrolase from which said mutant SAH hydrolase is derived.

The mutant SAH hydrolase can be derived from any suitable sources. For example, the mutant SAH hydrolase can be derived from a mammalian SAH hydrolase, e.g., derived from a human SAH hydrolase.

In a specific embodiment, the mutant SAH hydrolase used in the method comprises the amino acid sequence set forth in SEQ ID NO:1 and comprises a mutation such as R38E, C53 S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A or Y432F, or a combination thereof.

Prior to the contact between the sample and the mutant SAH hydrolase, oxidized or conjugated Hcy in the sample can be converted into reduced Hcy. Similarly, prior to the contact between the sample and the mutant SAH hydrolase, the Hcy in the sample can be converted into SAH. Preferably, oxidized or conjugated Hcy in the sample is converted into reduced Hcy and then the reduced Hcy is converted into SAH.

Hcy in the sample can be converted into SAH by any suitable method, e.g., by a wild-type SAH hydrolase and access adenosine. Preferably, the access adenosine in the sample is removed by adenosine deaminase while the wild-type SAH hydrolase is inhibited. Any suitable SAH hydrolase inhibitors can be used, e.g., neplanocin A or aristeromycin.

The present method can further comprise a step of removing the reducing agent used to convert oxidized or conjugated Hcy into reduced Hcy prior to or concurrently with contacting the sample with the mutant SAH hydrolase. The reducing agent can be removed by any suitable methods such as chromatography. Exemplary chromatography includes column, paper, thin layer and batch chromatography. Preferably, the reducing agent is removed by batch chromatography. The removal of the reducing agent can have certain benefits such as increasing assay sensitivity. The degree of the removal is affected by a number of factors including the reducing agent used, the removal methods used and the objective of the removal. Although the reducing agent may be substantially removed, it is often not necessary to do so; for a 10–50 percent reduction of the reducing agent can bring significant benefits to the assay.

An indicator dye can be used in the present method for various reasons, e.g., for the ease of monitoring sample and reagent addition and transfer. The present method can further comprise a step of removing the indicator dye prior to or concurrently with contacting the sample with the mutant SAH hydrolase. The indicator dye can be removed by any suitable methods such as chromatography. Exemplary chromatography includes column, paper, thin layer and batch chromatography. Preferably, the indicator dye is removed by batch chromatography. The degree of the removal is affected by a number of factors including the indicator dye used, the removal methods used and the objective of the removal.

Although the reducing agent may be substantially removed, it is often not necessary to do so; for a 10–70 percent reduction of the indicator dye can bring significant benefits to the assay.

In a specific embodiment, the reducing agent and the indicator dye are removed by the same method, e.g., chromatography. Preferably, the reducing agent and the indicator dye are removed by a batch chromatography.

The present method can be conducted in any suitable format, e.g., in a competitive or sandwich format, in solution or on a solid support. In a specific embodiment, the SAH is contacted with the mutant SAH hydrolase in the presence of a labeled SAH or a derivative or an analogue thereof, thereby the amount of the mutant SAH hydrolase bound to the labeled SAH inversely relates to the amount of SAH in the sample. Any suitable labels can be used such as chemical, radioactive, enzymatic, fluorescent or luminescent label. Preferably, the labeled SAH or a derivative or an analogue thereof is fluorescently, enzymatically or proteinaceously labeled. For example, the fluorescently labeled SAH can be fluorecin-SAH conjugate or Rocamin-SAH conjugate, said fluorecin or Rocamin being linked to said SAH or a derivative or an analogue thereof by a linker of 1–15 carbon atom length; the enzymatically labeled SAH derivative can be Glucose-6-phosphate dehydrogenase (G-6-PDH-SAH) conjugate, alkaline phosphatase-SAH conjugate, or malate dehydrolase-SAH conjugate, said G-6-PDH, alkaline phosphatase or malate dehydrolase being linked to said SAH or a derivative or an analogue thereof by a linker of 1–15 carbon atom length; and the proteinaceously labeled SAH derivative can be bovine albumin-SAH conjugate, said bovine albumin being linked to said SAH or a derivative or an analogue thereof by a linker of 1–15 carbon atom length.

In another specific embodiment, the mutant SAH hydrolase is a labeled mutant SAH hydrolase. Any suitable labels can be used such as chemical, radioactive, enzymatic, fluorescent or luminescent label. Preferably, the labeled mutant SAH hydrolase is a fluorescently, enzymatically, biotin or streptavidin labeled mutant SAH hydrolase. For example, the biotin labeled mutant SAH hydrolase is detected by a streptavidin labeled enzyme; the streptavidin labeled enzyme is a streptavidin labeled horse radish phosphatase (HRP).

The labeled SAH or a derivative or an analogue thereof, or the labeled mutant SAH hydrolase can be immobilized on a surface suitable for conducting an assay for Hcy or its related moieties. For example, the bovine albumin-SAH conjugate can be immobilized.

In a specific assay format, the fluorescently labeled SAH or a derivative or an analogue thereof is directly contacted by the mutant SAH hydrolase, and the resulting change of fluorescent polarization is measured for assessing Hcy, SAH or adenosine. In another specific assay format, the enzymatically labeled SAH or a derivative or an analogue thereof is directly contacted by the mutant SAH hydrolase, and the resulting change of enzyme activity is measured for assessing Hcy, SAH or adenosine.

The present method can be used to assay any sample, e.g., a body fluid or a biological tissue. Exemplary body fluids include urine, blood, plasma, serum, saliva, semen, stool, sputum, cerebral spinal fluid, tears, mucus and amniotic fluid. Preferably, the body fluid to be assayed is blood. The blood sample can be assayed directly or be treated before assaying. For example, the blood sample can be further separated into a plasma or serum fraction.

The present method can be used alone, or can be used in combination with other related assays. For example, the present method can further comprise a step of detecting cholesterol and/or folic acid in the sample, whether sequentially or simultaneously.

In another aspect, the present invention is directed to a combination, which combination comprises: a) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and b) reagents for detecting binding between Hcy, SAH or adenosine and said SAH hydrolase. The combination can further comprise a reagent for detecting cholesterol and/or folic acid.

A kit comprising the above combination is also provided. The kit can further comprise instructions for assaying Hcy, SAH or adenosine in a sample.

In still another aspect, the present invention is directed to an article of manufacture, which article of manufacture comprises: a) packaging material; b) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and c) a label indicating that the mutant SAH hydrolase and the means for use in assaying Hcy, SAH or adenosine in a sample.

In yet another aspect, the present invention is directed to an isolated nucleic acid fragment, which isolated nucleic acid fragment comprises a sequence of nucleotides encoding a mutant SAH hydrolase, wherein said mutant SAH hydrolase comprises the amino acid sequence set forth in SEQ ID NO:1 or a nucleotide sequence set forth in SEQ ID NO:2 and comprises one or more of the following mutations: R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, 1240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F.

The isolated nucleic acid fragment can be in any suitable forms, e.g., DNA, RNA, PNA, etc., or a combination thereof. A plasmid comprising the above isolated nucleic acid fragment is also provided. A cell comprising the above plasmid is also provided. Any suitable cells can be used. For example, the cell can be a bacterial cell, a yeast cell, a fungal cell, a plant cell, an insect cell or an animal cell. A method for producing a mutant SAH hydrolase is also provided, which method comprises growing the above cell under conditions whereby the mutant SAH hydrolase is expressed by the cell, and recovering the expressed mutant SAH hydrolase.

In yet another aspect, the present invention is directed to a substantially purified mutant SAH hydrolase, wherein said mutant SAH hydrolase comprises the amino acid sequence set forth in SEQ ID NO:1 and comprises one or more of the following mutations: R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, 1240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F.

In yet another aspect, the present invention is directed to a conjugate, which conjugate comprises: a) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and b) a facilitating agent linked to the mutant SAH hydrolase directly or via a linker, wherein the agent facilitates: i) affinity isolation or purification of a conjugate; ii) attachment of a conjugate to a surface; or iii) detection of a conjugate. The conjugate can be a fusion protein. Alternatively, the mutant SAH hydrolase and the facilitating agent can be linked by other means.

MODES OF CARRYING OUT THE INVENTION

Figure 1:
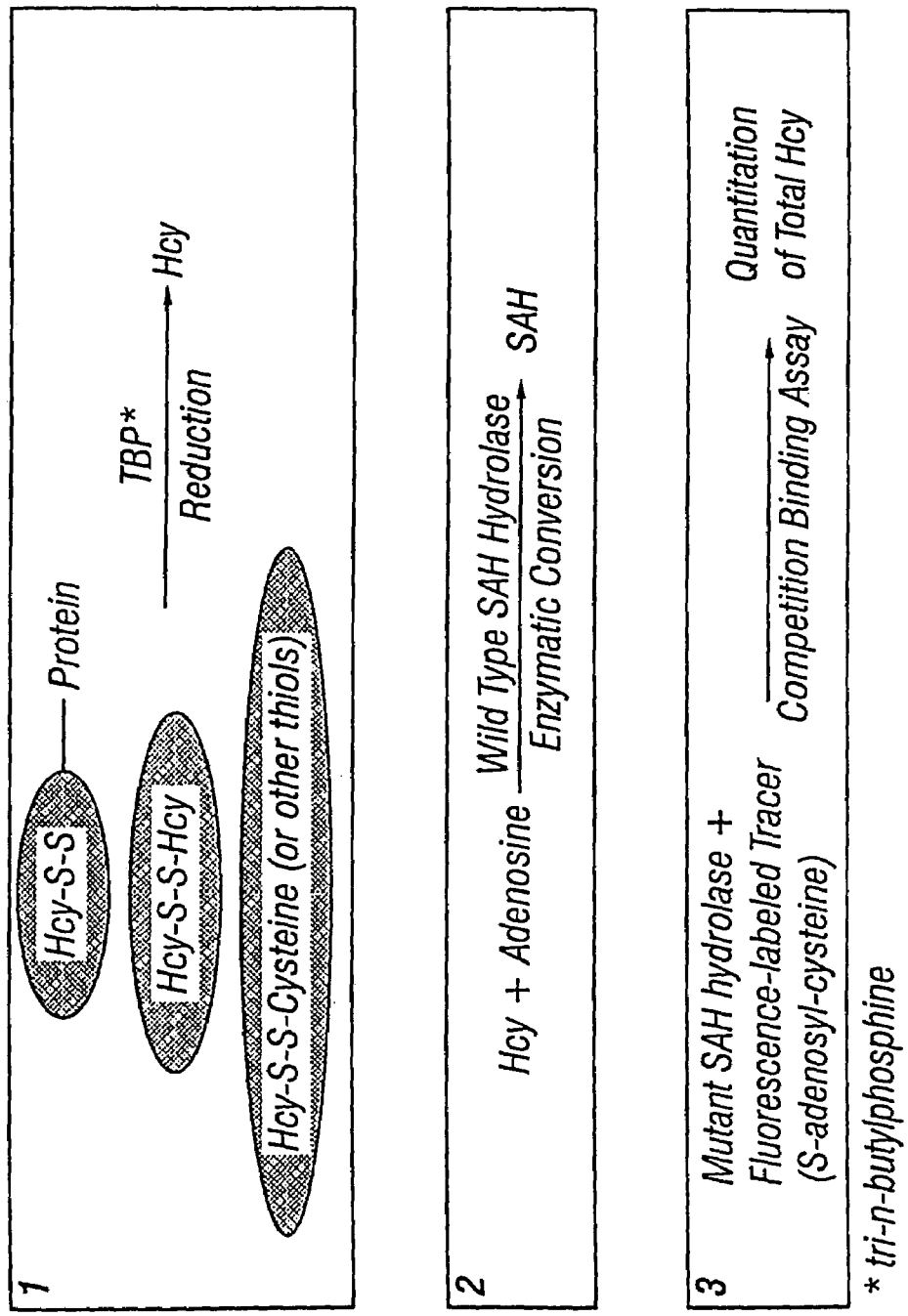
FIG. 1 depicts Hcy assay using wild type and mutant SAH hydrolase.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "homocysteine (Hcy)" refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through disulfide bond.

As used herein, "SAH hydrolase" refers to an ubiquitous eukaryotic enzyme, which is also found in some prokaryotes, which catalyzes hydrolysis of SAH to adenosine (Ado) and Hcy. SAH hydrolase also catalyzes the formation of SAH from Ado and Hcy. The co-enzyme of SAH hydrolase is $NAD^+/NADH$. SAH hydrolase may have several catalytic activities. In the hydrolytic direction, the first step involves oxidation of the 3'-hydroxyl group of SAH (3'-oxidative activity) by enzyme-bound $NAD^+$ ($E-NAD^+$), followed by β-elimination of L-Hcy to give 3'-keto-4',5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein, "mutant SAH hydrolase, wherein said mutant SAH hydrolase has binding affinity for Hcy, SAH or adenosine but has attenuated catalytic activity" refers to a mutant form of SAH hydrolase that retains sufficient binding affinity for Hcy, SAH or adenosine to be detected in the process or method, particularly assay, of interest. Typically this is at least about 10%, preferably at least about 50% binding affinity for Hcy, SAH or adenosine, compared to its wildtype counterpart SAH hydrolase. Preferably, such mutant SAH hydrolase retains 60%, 70%, 80%, 90%, 100% binding affinity for Hcy, SAH or adenosine compared to its wildtype counterpart Hcy, SAH or adenosine, or has a higher binding affinity than its wildtype counterpart Hcy, SAH or adenosine. Such mutant Hcy, SAH or adenosine can be herein referred to as a "substrate trapping Hcy, SAH or adenosine," i.e., a molecule that specifically binds to Hcy, SAH or adenosine, but does not catalyze conversion therebetween.

As used herein, a conjugate refers to the compounds provided herein that include one or more mutant analyte-binding enzymes, e.g., mutant SAH hydrolase, and one or more facilitating agents. These conjugates include those produced by recombinant means as fusion proteins, those produced by chemical means, such as by chemical coupling, through, for example, coupling to sulfhydryl groups, and those produced by any other method whereby at least one mutant analyte-binding enzyme is linked, directly or indirectly via linker(s) to a facilitating agent.

As used herein, a facilitating agent is any moiety, such as a protein or effective portion thereof, that promotes or facilitates, for example, preferably:

i) affinity isolation or purification of the conjugate;

ii) attachment of the conjugate to a surface; or iii) detection of the conjugate or complexes containing the conjugate.

As used herein the term "assessing" is intended to include quantitative and qualitative determination in the sense of obtaining an absolute value for the amount or concentration of the analyte, e.g., a homocysteine co-substrate, present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, "attenuated catalytic activity" refers to a mutant SAH hydrolase that retains sufficiently reduced catalytic activity to be useful in the present method. The precise reduction in catalytic activity for use in the assays can be empirically determined for each assay. Typically, the enzyme will retain less than about 50% of one of its catalytic activities or less than 50% of its overall catalytic activities compared to its wildtype counterpart. Preferably, a mutant SAH hydrolase retains less than 40%, 30%, 20%, 10%, 1%, 0.1%, or 0.01% of one of its catalytic activities or its overall catalytic activities compared to its wildtype counterpart. More preferably, a mutant SAH hydrolase lacks detectable level of one of its catalytic activities or its overall catalytic activities compared to its wildtype counterpart. In instances in which catalytic activity is retained and/or a further reduction thereof is desired, the contacting step can be effected in the presence of a catalysis inhibitor. Such inhibitors, include, but are not limited to, heavy metals, chelators or other agents that bind to a co-factor required for catalysis, but not for binding, and other such agents.

As used herein, "SAH hydrolase catalysis inhibitor" refers to an agent that inhibits one or all of SAH hydrolase catalytic activities, e.g., 3'-oxidative activity, 5'-hydrolytic activity, or 3'-reduction activity, while not affecting SAH hydrolase's binding affinity for Hcy and/or SAH.

As used herein, "adenosine deaminase" refers to an enzyme that catalyzes the deamination of adenosine to form inosine. It is intended to encompass adenosine deaminase with conservative amino acid substitutions that do not substantially alter its activity.

As used herein, "folate species" refers to folate or folic acid, which is chemically N-[4-[[2-amino-1,4-dihydro-4-oxo-6-pteridinyl)methyl]amino]benzxoyl]-L-glutamic acid, or a derivative thereof. Examples of folate derivatives include, but are not limited to, dihydrofolate, tetrahydrofolate, 5,-methyl-tetrahydrofolate and 5,10-methylene tetrahydrofolate.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "substantially pure" means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, "antibody" includes antibody fragments, such as Fab fragments, which are composed of a light chain and the variable region of a heavy chain.

As used herein, "production by recombinant means" refers to production methods that use recombinant nucleic acid methods that rely on well known methods of molecular biology for expressing proteins encoded by cloned nucleic acids.

As used herein, "complementary" when referring to two nucleic acid molecules, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: "stringency of hybridization" in determining percentage mismatch is as follows:

1) high stringency: 0.1×SSPE, 0.1% SDS, 65° C.;

2) medium stringency: 0.2×SSPE, 0.1% SDS, 50° C. (also referred to as moderate stringency); and 3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, a "composition" refers to any mixture of two or more products or compounds. It may be a solution, a suspension, liquid, powder, a paste, aqueous, non-aqueous or any combination thereof.

As used herein, a "combination" refers to any association between two or among more items.

As used herein, "fluid" refers to any composition that can flow. Fluids thus encompass compositions that are in the form of semi-solids, pastes, solutions, aqueous mixtures, gels, lotions, creams and other such compositions.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266: 19867–19870 (1991)) can be inserted immediately 5' of the start codon and may enhance expression. The desirability of (or need for) such modification may be empirically determined.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

As used herein, "protein binding sequence" refers to a protein or peptide sequence that is capable of specific binding to other protein or peptide sequences generally, to a set of protein or peptide sequences or to a particular protein or peptide sequence.

As used herein, "epitope tag" refers to a short stretch of amino acid residues corresponding to an epitope to facilitate subsequent biochemical and immunological analysis of the "epitope tagged" protein or peptide. "Epitope tagging" is achieved by appending the sequence of the "epitope tag" to the protein-encoding sequence in an appropriate expression vector. "Epitope tagged" proteins can be affinity purified using highly specific antibodies raised against the tags.

As used herein, "Protein A or Protein G" refers to proteins that can bind to Fc region of most IgG isotypes. Protein A or Protein G are typically found in the cell wall of some strains of *staphylococci*. It is intended to encompass Protein A or Protein G with conservative amino acid substitutions that do not substantially alter its activity.

As used herein, "nucleotide binding sequence" refers to a protein or peptide sequence that is capable of specific binding to nucleotide sequences generally, to a set of nucleotide sequences or to a particular nucleotide sequence.

As used herein, "lipid binding sequence" refers to a protein or peptide sequence that is capable of specific binding to lipids generally, to a set of lipids or to a particular lipid.

As used herein, "polysaccharide binding sequence" refers to a protein or peptide sequence that is capable of specific binding to polysaccharides generally, to a set of polysaccharides or to a particular polysaccharide.

As used herein, "metal binding sequence" refers to a protein or peptide sequence that is capable of specific binding to metal ions generally, to a set of metal ions or to a particular metal ion.

As used herein, "alkaline phosphatases" refers to a family of functionally related enzymes named after the tissues in which they predominately appear. Alkaline phosphatases carry out hydrolase/transferase reactions on phosphate-containing substrates at a high pH optimum. It is intended to encompass alkaline phosphatases with conservative amino acid substitutions that do not substantially alter its activity.

As used herein, "glutathione S-transferase" refers to a ubiquitous family of enzymes with dual substrate specificities that perform important biochemical functions of xenobiotic biotransformation and detoxification, drug metabolism, and protection of tissues against peroxidative damage. The basic reaction catalyzed by glutathione S-transferase is the conjugation of an electrophile with reduced glutathione (GSH) and results in either activation or deactivation/detoxification of the chemical. It is intended to encompass a glutathione S-transferase with conservative amino acid substitutions that do not substantially alter its activity.

As used herein, high-throughput screening (HTS) refers to processes that test a large number of samples, such as samples of diverse chemical structures against disease targets to identify "hits" (see, e.g., Broach, et al., High throughput screening for drug discovery, *Nature,* 384:14–16 (1996); Janzen, et al., High throughput screening as a discovery tool in the pharmaceutical industry, *Lab Robotics Automation:* 8261–265 (1996); Fernandes, P. B., Letter from the society president, *J. Biomol. Screening,* 2:1 (1997); Burbaum, et al., New technologies for high-throughput screening, *Curr. Opin. Chem. Biol.,* 1:72–78 (1997)]. HTS operations are highly automated and computerized to handle sample preparation, assay procedures and the subsequent processing of large volumes of data.

As used herein, "disease or disorder" refers to a pathological condition in an organism resulting from, e.g., infection or genetic defect, and characterized by identifiable symptoms.

B. METHODS FOR ASSAYING HCY, SAH OR ADENOSINE

In one aspect, the present invention is directed to a method for assaying homocysteine (Hcy), S-adenosylhomocysteine (SAH) or adenosine in a sample, which method comprises: a) contacting a sample containing or suspected of containing Hcy, SAH or adenosine with a mutant SAH hydrolase, wherein said mutant SAH hydrolase has binding affinity for Hcy, SAH or adenosine but has attenuated catalytic activity, and said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and b) detecting binding between Hcy, SAH or adenosine with said mutant SAH hydrolase, whereby the presence or amount of Hcy, SAH or adenosine in said sample is assessed.

Nucleic Acids Encoding SAH Hydrolase

Nucleic acids encoding SAH hydrolase can be obtained by methods known in the art. Additional nucleic acid molecules encoding such enzymes are known and the molecules or sequences thereof are publicly available. If the molecules are available they can be used; alternatively the known sequences can be used to obtain clones from selected or desired sources. For example, the nucleic acid sequences of SAH hydrolases can be used in isolating nucleic acids encoding SAH hydrolases from natural sources. Alternatively, nucleic acids encoding SAH hydrolases can be obtained by chemical synthesis according to the known sequences.

In one embodiment, the nucleic acid molecules containing sequences of nucleotides with the following GenBank accession Nos. can be used in obtaining nucleic acid encoding SAH hydrolase: AF129871 (*Gossypium hirsutum*); AQ003753 (*Cryptosporidium parvum*); AF105295 (*Alexandrium fundyense*); AA955402 (*Rattus norvegicus*); AA900229 (*Rattus norvegicus*); AA874914 (*Rattus norvegicus*); AA695679 (*Drosophila melanogaster* ovary); AA803942 (*Drosophila melanogaster* ovary; AI187655 (*Manduca sexta* male antennae); U40872 (*Trichomonas vaginalis*); AJ007835 (*Xenopus Laevis*); AF080546 (*Anopheles gambiae*); AI069796 (*T. cruzi* epimastigote); Z97059 (*Arabidopsis thaliana*); AF059581 (*Arabidopsis thaliana*); U82761 (*Homo sapiens*); AA754430 (*Oryza sativa*); D49804 (*Nicotiana tabacum*); D45204 (*Nicotiana tabacum*); X95636 (*D. melanogaster*); T18277 (endosperm Zea mays); R75259 (Mouse brain); Z26881 (*C. roseus*); X12523 (*D. discoideum*); X64391 (*Streptomyces fradiae*); W21772 (Maize Leaf); AH003443 (*Rattus norvegicus*); U14963 (*Rattus norvegicus*); U14962 (*Rattus norvegicus*); U14961 (*Rattus norvegicus*); U14960 (*Rattus norvegicus*); U14959 (*Rattus norvegicus*); U14937 (*Rattus norvegicus*); U14988 (*Rattus norvegicus*); U14987 (*Rattus norvegicus*); U14986 (*Rattus norvegicus*); U14985 (*Rattus norvegicus*); U14984 (*Rattus norvegicus*); U14983 (*Rattus norvegicus*); U14982 (*Rattus norvegicus*); U14981 (*Rattus norvegicus*);

U14980 (*Rattus norvegicus*); U14979 (*Rattus norvegicus*); U14978 (*Rattus norvegicus*); U14977 (*Rattus norvegicus*); U14976 (*Rattus norvegicus*); U14975 (*Rattus norvegicus*); L32836 (*Mus musculus*); L35559 (*Xenopus laevis*); Z19779 (Human foetal Adrenals tissue); L23836 (*Rhodobacter capsulatus*); M15185 (Rat); L11872 (*Triticum aestivum*); M19937 (Slime mold (*D. discoideum*); M80630 (*Rhodobacter capsulatus*). Preferably, the nucleic acid molecules containing nucleotide sequences with the GenBank accession Nos. M61831–61832 can be used in obtaining nucleic acid encoding SAH hydrolase (SEQ ID No.1; see also Coulter-Karis and Hershfield, *Ann. Hum. Genet.*, 53(2): 169–175 (1989)). Also preferably, the nucleic acid molecule containing the sequence of nucleotides or encoding the amino acids set forth in SEQ ID No. 3 can be used (see also U.S. Pat. No. 5,854,023).

Selecting and Producing Hcy-Binding Enzymes

Once nucleic acids encoding SAH hydrolases are obtained, these nucleic acids can be mutagenized and screened and/or selected for mutant SAH hydrolase having binding affinity for Hcy, SAH or adenosine but having attenuated catalytic activity. Insertion, deletion, or point mutation(s) can be introduced into nucleic acids encoding SAH hydrolases according to methods known to those of skill in the art. Information regarding the structural-functional relationship of the SAH hydrolases can be used in the mutagenesis and selection of mutant SAH hydrolase having binding affinity for Hcy, SAH or adenosine but having attenuated catalytic activity.

In one example, the mutant SAH hydrolase used in the method has a mutation in an amino acid residue that is directly involved in the SAH hydrolase's catalytic activity, its binding with NAD$^+$, NADH, Hcy, SAH or adenosine. In another example, the mutant SAH hydrolase used in the method has a mutation in an amino acid residue that is adjacent to an amino acid residue that is directly involved in the SAH hydrolase's catalytic activity, its binding with NAD$^+$, NADH, Hcy, SAH or adenosine. Information on the SAH hydrolase's catalytic domain, various binding domains including the NAD binding domain and conserved amino acid residues are generally known and can be used in the designing of a suitable mutant SAH hydrolase (See e.g., Turner et al., *Nat. Struct. Biol.*, 5(5):369–76 (1998) entitled "Structure determination of selenomethionyl S-adenosylhomocysteine hydrolase using data at a single wavelength;" Yin et al., *Biomedical Chemistry: Applying Chemical Principles to the Understading and Treatetment of Diesease* (Ed. Torrence), Chapter 2, Mechanism-based S-adenosylhomocysteine hydrolase inhibitors in the saerch for broad-spectrum antiviral agents), John Wiley & Sons, Inc. (2000); Hu et al., *Biochemistry*, 38(26):8323–33 (1999) entitled "Crystal structure of S-adenosylhomocysteine hydrolase from rat liver;" Creedon et al., *J. Biol. Chem.*, 269(23): 16364–70 (1994) entitled "*Plasmodium falciparum* S-adenosylhomocysteine hydrolase. cDNA identification, predicted protein sequence, and expression in *Escherichia coli*.;" and Henderson et al., *Mol. Biochem. Parasitol.*, 53(1-2): 169–83 (1992) entitled "Cloning of the gene encoding *Leishmania donovani* S-adenosylhomocysteine hydrolase, a potential target for antiparasitic chemotherapy."

Once a mutant SAH hydrolase with desired properties, i.e., substantially retaining binding affinity for Hcy, SAH or adenosine but having attenuated catalytic activity, is identified, such mutant SAH hydrolase can be produced by any methods known in the art including recombinant expression, chemical synthesis or a combination thereof. Preferably, the mutant SAH hydrolase is obtained by recombinant expression.

Mutant SAH Hydrolase and Nucleic Acids Encoding the Mutant SAH Hydrolase

SAH hydrolase from mammalian sources are homotetramer of approximate molecular weight of 180–190 KD. The enzyme contains 4 molecules of tightly-bound NAD$^+$ as a co-enzyme. The catalytic mechanism of the enzyme in the hydrolytic direction includes two consecutive reactions, i.e., the 3'-oxidation of the substrate to 3'-keto in concomitant with the reduction of the enzyme-bound NAD$^+$ to NADH, and followed by the 5'-hydrolysis to release the reaction products Hcy and Ado (Refsum, et al., *Clin. Chem.*, 31:624–628 (1985)). The C-terminal regions of all known SAH hydrolase are extremely conserved and contain essential amino acid residues to the enzyme catalysis. The crystal structure of human SAH hydrolase in complex with a substrate analog inhibitor was recently determined. This x-ray structure of SAH hydrolase indicates that at least twenty amino acid residues are directly or indirectly interacting with the substrate analog inhibitor and co-enzyme NAD$^+$. Mutations of those amino acid residues that are involved directly or indirectly in the substrate binding and catalysis can readily be made by site-directed mutagenesis, and the sequence of the resulting mutant enzyme can be confirmed by comparing the mutant SAH hydrolase DNA sequence with the sequence of the wild type enzyme to ensure no other mutations are introduced to the specific mutant enzyme.

Provided herein is a substantially purified mutant SAH hydrolase that substantially retains its binding affinity or has enhanced binding affinity for Hcy, SAH or adenosine but has attenuated catalytic activity.

In one specific embodiment, the attenuated catalytic activity of the mutant SAH hydrolase is caused by mutation(s) in the mutant SAH hydrolase's binding site for NAD$^+$, or mutation(s) in the mutant SAH hydrolase's catalytic site or a combination thereof.

In another specific embodiment, the mutant SAH hydrolase has attenuated 5'-hydrolytic activity but substantially retains its 3'-oxidative activity.

In still another specific embodiment, the mutant SAH hydrolase irreversibly binds SAH.

In yet another specific embodiment, the mutant SAH hydrolase has a Km for SAH that is about or less than 10.0 µM. Preferably, the mutant SAH hydrolase has a Km for SAH that is about 1.0 µM or less than 1.0 µM.

In yet another specific embodiment, the mutant SAH hydrolase has a Kcat for SAH that is about or less than 0.1 $S^{-1}$.

In yet another specific embodiment, the mutant SAH hydrolase has one or more insertion, deletion, or point mutation(s). Preferably, the mutant SAH hydrolase is derived from the sequence of amino acids set forth in SEQ ID NO:1 or encoded by the sequence of nucleotides set forth in SEQ ID NO:2 but has one or more of the following mutations: R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F, and deletion of Tyr 432 (Δ432). Also more preferably, the mutant SAH hydrolase is a derived sequence of amino acids set forth in SEQ ID NO:1 or encoded by the sequence of nucleotides set forth in SEQ ID NO:2 and has a combination of Arg 431 to Ala (R431A) and Lys 426 to Arg (K426R) mutations. The nucleic acid molecules contemplated also include those that have conservative amino acid changes, and include those that hybridize along their full length to the coding portion of the sequence of nucleotides set forth in SEQ ID NO:2, under medium stringency, or preferably high stringency, such that the encoded protein retains ability to bind to the selected analyte without substantial conversion of the analyte.

Also provided herein is an isolated nucleic acid fragment, either DNA or RNA, that includes a sequence of nucleotides encoding a mutant S-adenosylhomocysteine (SAH) hydrolase, the mutant SAH hydrolase substantially retains its binding affinity or has enhanced binding affinity for homocysteine Hcy, SAH or adenosine but has attenuated catalytic activity.

In one specific embodiment, the isolated nucleic acid fragment encodes a mutant SAH hydrolase wherein the attenuated catalytic activity is caused by mutation(s) in the mutant SAH hydrolase's binding site for NAD$^+$, or mutation(s) in the mutant SAH hydrolase's catalytic site or a combination thereof.

In another specific embodiment, the isolated nucleic acid fragment encodes a mutant SAH hydrolase wherein the mutant SAH hydrolase has attenuated 5'-hydrolytic activity but substantially retains its 3'-oxidative activity.

In still another specific embodiment, the isolated nucleic acid fragment encodes a mutant SAH hydrolase wherein the mutant SAH hydrolase irreversibly binds SAH.

In yet another specific embodiment, the isolated nucleic acid fragment encodes a mutant SAH hydrolase wherein the mutant SAH hydrolase has a Km for SAH that is about or less than 10.0 µM. Preferably, the isolated nucleic acid fragment encodes a mutant SAH hydrolase wherein the mutant SAH hydrolase has a Km for SAH that is about 1.0 µM or less than 1.0 µM.

In yet another specific embodiment, the isolated nucleic acid fragment encodes a mutant SAH hydrolase wherein the mutant SAH hydrolase has a Kcat for SAH that is about or less than 0.1 S$^{-1}$.

In yet another specific embodiment, the isolated nucleic acid fragment encodes a mutant SAH hydrolase wherein the mutant SAH hydrolase has one or more insertion, deletion, or point mutation(s). Preferably, the isolated nucleic acid fragment encodes a mutant SAH hydrolase wherein the mutant SAH hydrolase is derived from a sequence of nucleotides set forth in SEQ ID NO:1 and has one or more mutation selected from R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F, and deletion of Tyr 432 (Δ432). Also more preferably, the isolated nucleic acid fragment encodes a mutant SAH hydrolase wherein the mutant SAH hydrolase is derived from a sequence of nucleotides set forth in SEQ ID NO:1 and has a combination of Arg 431 to Ala (R431A) and Lys 426 to Arg (K426R) mutations.

Further provided is a plasmid, including the nucleic acid fragment encoding the above mutant SAH hydrolases. Preferably, the plasmid is an expression vector including a sequence of nucleotides encoding: a) a promoter region; and b) a mutant S-adenosylhomocysteine (SAH) hydrolase, the mutant SAH hydrolase substantially retains its binding affinity or has enhanced binding affinity for Hcy, SAH or adenosine but has attenuated catalytic activity. The sequence of nucleotides encoding the mutant SAH hydrolase is operatively linked to the promoter, whereby the mutant SAH hydrolase is expressed. More preferably, the plasmid also includes a selectable marker.

Further provided is a recombinant host cell containing the above plasmid. The recombinant host cell can be any suitable host cell, including, but not limited to, a bacterial cell, a yeast cell, a fungal cell, a plant cell, an insect cell or an animal cell.

Also provided are methods for producing a mutant SAH hydrolase. The recombinant host cells can be grown or cultured under conditions whereby the mutant SAH hydrolase is expressed by the cell. The expressed mutant SAH hydrolase can then be isolated or recovered.

Additional mutant SAH hydrolase that substantially retains its binding affinity or has enhanced binding affinity for Hcy, SAH or adenosine, but has attenuated catalytic activity can be produced according to the procedures known to the those of skill in the art. The above-described mutant SAH hydrolases and additional mutant SAH hydrolase that substantially retain binding affinity or have enhanced binding affinity for Hcy, SAH or adenosine but have attenuated catalytic activity can be used for assaying Hcy in a sample.

Hcy Assays Using Mutant SAH Hydrolase

Figure 2:
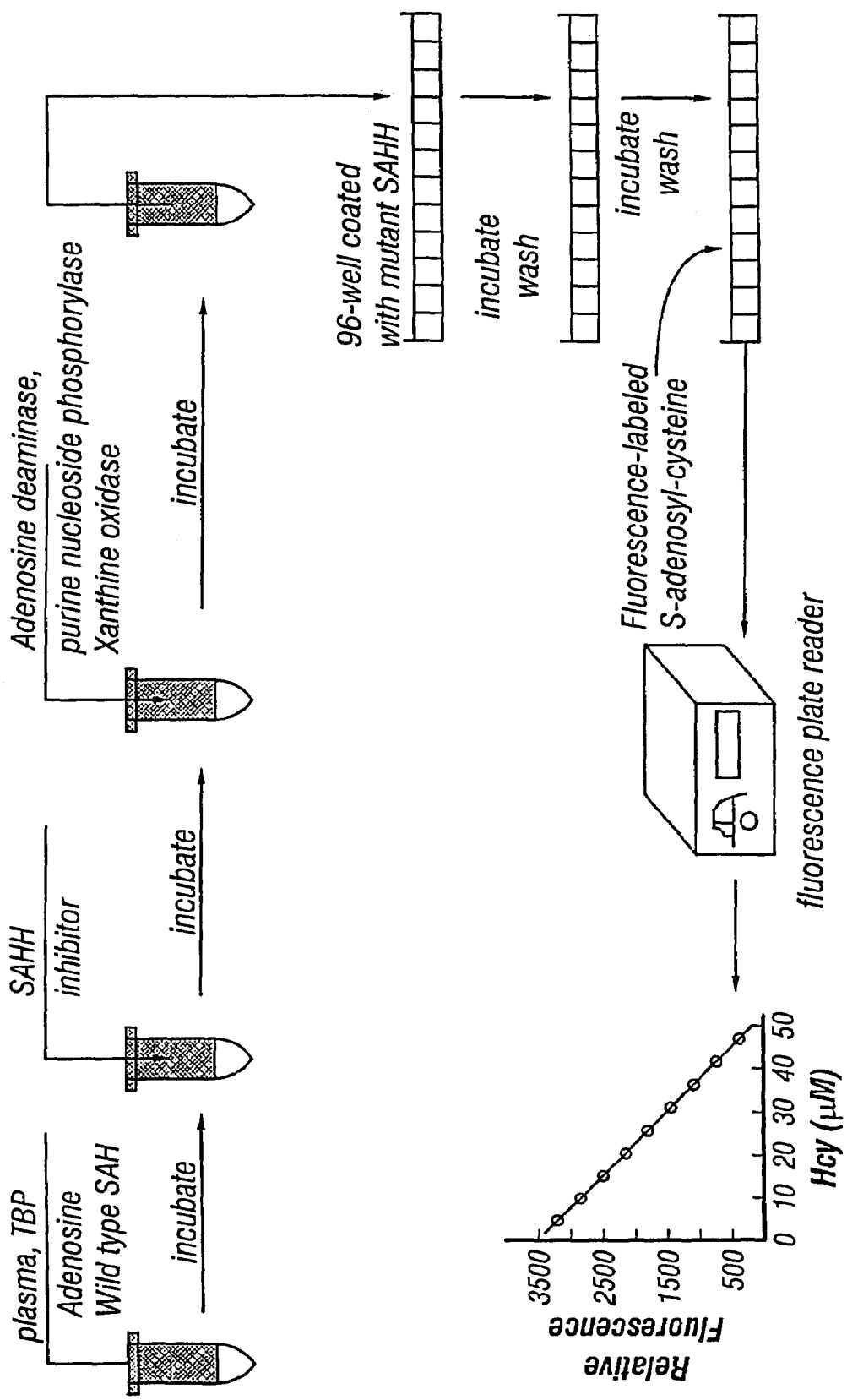
FIG. 2 depicts total plasma Hcy assay procedure with wild type and mutant SAH hydrolase.

In one specific embodiment, the mutant Hcy-binding enzyme used in the Hcy assay is a mutant SAH hydrolase, the mutant SAH hydrolase substantially retains its binding affinity or has enhanced binding affinity for Hcy, SAH or adenosine but has attenuated catalytic activity. This assay, illustrated in detail in the EXAMPLES, is depicted in FIG. 1. In this Figure, the homocysteine-containing analyte is reduced to produce Hcy, which, is quantified or detected by binding it to a mutant (substrate trapping) SAH hydrolase; the Hcy is then converted to SAH by reaction with adenosine in the presence of wild type SAH hydrolase. As exemplified in the Figure, instead of using a monoclonal antibody to effect quantitation (see, e.g., U.S. Pat. No. 5,885,767 and U.S. Pat. No. 5,631,127). Quantitation is effected using a fluorescence-labeled tracer S-adenosylcysteine in a competition binding format in which the mutant SAH is used to trap the substrate. Any suitable quantitation assay with any suitable label can be used in the substrate trapping method. FIG. 2 depicts an exemplary assay performed in a 96 well format; and FIG. 3 exemplifies preparation of labeling of adenosyl-cysteine with a fluorescent moiety.

In one preferred embodiment, the attenuated catalytic activity in the mutant SAH hydrolase is caused by mutation(s) in the mutant SAH hydrolase's binding site for NAD$^+$, or mutation(s) in the mutant SAH hydrolase's catalytic site or a combination thereof.

In another preferred embodiment, the mutant SAH hydrolase has attenuated 5'-hydrolytic activity but substantially retains its 3'-oxidative activity.

In another preferred embodiment, the mutant SAH hydrolase irreversibly binds SAH.

In still another preferred embodiment, the mutant SAH hydrolase has a Km for SAH that is about or less than 10.0 µM. More preferably, the mutant SAH hydrolase has a Km for SAH that is about 1.0 µM or less than 1.0 µM.

In yet another preferred embodiment, the mutant SAH hydrolase has a Kcat for SAH that is about or less than 0.1 S$^{-1}$.

In yet another preferred embodiment, the mutant SAH hydrolase has one or more insertion, deletion, or point mutation(s). More preferably, the mutant SAH hydrolase is derived from the sequence of amino acids set forth in SEQ ID NO:1 or encoded by the sequence of nucleotides set forth in SEQ ID No. 2 and has one or more of the following mutations: R38E, C53S, L54G, T57G, T57S, E59D, N80G, S83G, Y100T, K121A, D131E, D134E, E155G, T157G, T158Y, T159Y, N181D, N181A, D190A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388G, H398A, K401R, K401D, T407S, L409G, S420T, P424A, F425S, P427A, D428G, H429A, Y430T, R431K, R431G, Y432S, Y432A, Y432F, and deletion of Tyr 432 (Δ432). Also more preferably, the mutant SAH hydrolase is derived from a sequence of amino acids set forth in SEQ ID NO:2 and has a combination of Arg 431 to Ala (R431A) and Lys 426 to Arg (K426R) mutations.

In yet another preferred embodiment, prior to the contact between the sample and the mutant SAH hydrolase, oxidized Hcy in the sample is converted into reduced Hcy. More preferably, the oxidized Hcy in the sample is converted into reduced Hcy by a reducing agent such as tri-n-butylphosphine (TBP), β-ME, DTT, dithioerythritol, thioglycolic acid, glutathione, tris(2-carboxyethyl)phosphine, sodium cyanoborohydride, $NaBH_4$, $KBH_4$ and free metals.

In yet another preferred embodiment, prior to the contact between the sample and the mutant SAH hydrolase, the Hcy in the sample is converted into SAH. More preferably, the Hcy in the sample is converted into SAH by a wild-type SAH hydrolase. Also more preferably, the SAH is contacted with the mutant SAH hydrolase in the presence of a SAH hydrolase catalysis inhibitor such as neplanocin A or thimersol.

In yet another preferred embodiment, prior to the contact between the SAH and the mutant SAH hydrolase, free adenosine is removed or degraded. More preferably, the free adenosine is degraded by combined effect of adenosine deaminase, purine nucleoside phosphorylase and xanthine oxidase.

Any adenosine deaminase can be used. Preferably, the adenosine deaminase encoded by the nucleic acids having the following GenBank accession Nos. can be used: AF051275 (*Caenorhabditis elegans*); AI573492 (mouse mammary gland); AI462267 (mouse mammary gland); AI429519 (mouse embryo); AI429513 (mouse embryo); AI326688 (Mus musculus); AI324114 (mouse placenta); AI322477 (mouse placenta); AI152550 (mouse uterus); U76422 (Human, see also Lai, et al., *Mol. Cell. Biol.*, 17(5):2413–24 (1997)); U76421 (Human); U76420 (Human); AI120695 (mouse mammary gland); AI049175 (Mus musculus); U73107 (Mus musculus); AF052506 (Mus musculus); AA871919 (Barstead bowel, Mus musculus); AA871917 (Barstead bowel, Mus musculus); AA871865 (Barstead bowel); AA871752 (Barstead bowel); AA871702 (Barstead bowel); AA871324 (Barstead bowel); AA871189 (Barstead bowel); AA869711 (Mus musculus); AA869187 (Mus musculus); AA869184 (Mus musculus); AA869176 (Mus musculus); AA869120 (Mus musculus); U75503 (Homo sapiens); AA646698 (mouse mammary gland); AA646681 (mouse mammary gland); AA427106 (mouse mammary gland); D50624 (*Streptomyces virginiae*); AA389303 (mouse embryo); AA389067 (mouse embryo); U88065 (*Xenopus laevis*); AA124740 (Mus musculus); U74586 (*Rattus norvegicus*); AA036487 (mouse placenta); AA035873 (mouse placenta); AA030290 (mouse placenta); AA023505 (mouse placenta); AA023331 (mouse placenta); AA111514 (mouse embryo); AA111327 (mouse embryo); AA110493 (mouse embryo); U73185 (Mus musculus); AA107590 (mouse embryo); AA102891 (mouse embryo); AA097525 (mouse embryo); AA096642 (mouse embryo); AA087094 (mouse embryo); AA060462 (mouse); U10439 (Human); M13792 (Human); U18942 (*Rattus norvegicus*); K02567 (Human); M10319 (Mouse); M59033 (*E. coli* adenosine). Preferably, the adenosine deaminase encoded by the nucleic acids having the following GenBank accession No. can be used: U76422 (Human, see also Lai, et al., *Mol. Cell. Biol.*, 17(5):2413–24 (1997)).

Any purine nucleoside phosphorylase can be used. Preferably, the purine nucleoside phosphorylase encoded by the nucleic acids having the following GenBank accession Nos. can be used: U88529 (*E. coli*); U24438 (*E. coli*, see also Cornell and Riscoe, *Biochim. Biophys. Acta,* 1396(1):8–14 (1998)); U83703 (*H. pylori*); and M30469 (*E. coli*).

Any xanthine oxidase can be used. Preferably, the xanthine oxidase encoded by the nucleic acids having the following GenBank accession Nos. can be used: AF080548 (*Sinorhizobium meliloti*); and U39487 (Human, see also Saksela and Raivio, *Biochem. J,* 315(1):235–9 (1996)).

In yet another preferred embodiment, the sample containing or suspected of containing SAH is contacted with the mutant SAH hydrolase in the presence of a labeled SAH or a derivative or an analog thereof, whereby the amount of the labeled SAH bound to the mutant SAH hydrolase inversely relates to amount of the SAH in the sample. The SAH, or the derivative or analog thereof, can be labeled by methods known in the art, e.g., to become radioactive, enzymatic, fluorescent, luminescent (including chemo- or bio-luminescent) labeled. More preferably, the labeled SAH derivative or analog is a fluorescence labeled adenosyl-cysteine.

In yet another preferred embodiment, the sample containing or suspected of containing SAH is contacted with a labeled mutant SAH hydrolase. The mutant SAH hydrolase can be labeled by methods known in the art, e.g., to become radioactive, enzymatic, fluorescent, luminescent (including chemo- or bio-luminescent) labeled. More preferably, the mutant SAH hydrolase is fluorescently labeled. For example, a mutant SAH hydrolase derived from an SAH hydrolase having sequence of amino acids encoded by the sequence of nucleotides set forth in SEQ ID NO:2 is used and the mutant SAH hydrolase is fluorescently labeled at residue Cys421.

The present method can be used alone, or can be used in combination with other related assays. For example, the present method can further comprise a step of detecting cholesterol and/or folic acid in the sample, whether sequentially or simultaneously. Any suitable methods for assaying cholesterol and/or folic acid can be used. For example, the cholesterol and/or folic acid assays disclosed in WO 01/02600 can be used.

C. COMBINATIONS, KITS AND ARTICLES OF MANUFACTURE

In another aspect, the present invention is directed to a combination, which combination comprises: a) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and b) reagents for detecting binding between Hcy, SAH or adenosine and said SAH hydrolase. The combination can further comprise a reagent for detecting cholesterol and/or folic acid.

A kit comprising the above the combination is also provided. The kit can further comprise instructions for assaying Hcy, SAH or adenosine in a sample.

In still another aspect, the present invention is directed to an article of manufacture, which article of manufacture comprises: a) packaging material; b) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and c) a label indicating that the mutant SAH hydrolase and the means for use in assaying Hcy in a sample.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

D. CONJUGATES

In yet another aspect, the present invention is directed to a conjugate, which conjugate comprises: a) a mutant SAH hydrolase that has binding affinity for Hcy, SAH or adenosine but has attenuated catalytic activity, wherein said binding affinity and/or said attenuated catalytic activity of said SAH hydrolase is caused by a mutation in said mutant SAH hydrolase's catalytic site, its binding site for $NAD^+$, NADH, Hcy, SAH or adenosine, or a combination thereof; and b) a facilitating agent linked to the mutant SAH hydrolase directly or via a linker, wherein the agent facilitates: i) affinity isolation or purification of a conjugate; ii) attachment of a conjugate to a surface; or iii) detection of a conjugate. The conjugate can be a fusion protein. Alternatively, the mutant SAH hydrolase and the facilitating agent can be linked by other means.

The conjugates can be produced by chemical conjugation, such as via thiol linkages, but are preferably produced by recombinant means as fusion proteins. In the fusion protein, the peptide or fragment thereof is linked to either the N-terminus or C-terminus of the mutant enzyme. In chemical conjugates the peptide or fragment thereof may be linked anywhere that conjugation can be effected, and there may be a plurality of such peptides or fragments linked to a single mutant enzyme or to a plurality thereof.

Conjugation can be effected by any method known to those of skill in the art. As described below, conjugation can be effected by chemical means, through covalent, ionic or any other suitable linkage. For example, the reagents and methods for conjugation as disclosed in WO 01/02600 can be used.

In some embodiments, the conjugate is a fusion protein, which prior to the contact between the sample and the fusion protein, is isolated or purified. More preferably, the fusion protein is isolated or purified through affinity binding between the protein or peptide fragment of the fusion protein and an affinity binding moiety. Any kind of affinity interaction can be used for isolating or purifying the fusion protein. The affinity interactions, such as those described herein, but not limited to, are protein/protein, protein/nucleotide, protein/lipid, protein/polysaccharide, or protein/metal interactions.

In other embodiments, prior to the contact between the sample and the conjugate, such as a fusion protein, the conjugate is attached to a surface. More preferably, the conjugate is attached to the surface through affinity binding between the facilitating agent of conjugate and an affinity binding moiety on the surface. Any kind of affinity interaction can be used for attaching the conjugate, including the protein/protein, protein/nucleotide, protein/lipid, protein/polysaccharide, or protein/metal interactions.

E. EXAMPLES

The following examples are included for illustrative purposes only and are not intended to limit the scope of the invention.

Example 1

Preparation of Mutant SAH Hydrolase-Encoding Nucleic Acid

Human placental SAH hydrolase gene (SEQ ID No. 1) was subcloned into an expression vector pKK223-3 (Pharmacia Biotech, Piscataway, N.J.) at the EcoR I site. pKK223-3 contains the strong tac promoter upstream from the multiple cloning site and the strong rrnB ribosomal terminator downstream for control of protein expression. The SAH hydrolase gene-containing expression vector was transferred into an *E. coli* strain JM109 (Invitrogen, Carlsbad, Calif.). Site-directed mutagenesis of SAH hydrolase was conducted in two ways: 1) single-strand DNA-based M13 method; and 2) double-strand DNA-based PCR method.

Single-Strand DNA-Based Mutagenesis

Single-strand DNA-based mutagenesis was conducted based on the method described by Taylor, et al., *Nucleic Acids Res.*, 13:8765–8785 (1985), which exploits the inability of NciI to cleave a thio-containing DNA strand. Sculptor™ invitro mutagenesis system RPN1526 (Amersham Life science, UK) was used. The pKK223-3 vector containing the wild type gene of SAH hydrolase was prepared using the method of alkaline lysis followed by plasmid purification using Promega's DNA purification kit (Wizard plus Minipreps, Promega, Madison Wis.). The purified plasmid was digested with EcoR I (Stratagene, La Jolla, Calif.) at 37° C. for 2 hours to obtain the EcoR I fragment by agarose gel electrophoresis followed by DNA purification using Promega DNA purification kit. The purified EcoR I fragment was subcloned into M13 mp19 DNA (Pharmacia Biotech, Piscataway, N.J.) by T4 DNA ligase (Pharmacia Biotech Piscataway, N.J.). The ligation was conducted in One-phor-All buffer (10 mM tris-Ac, pH 7.5, 10 mM Mg(Ac)2, 50 mM KAc; Pharmacia LKB Biotechnology AB, Uppsala, Sweden) at 4° C. overnight. The ligation product was transferred into TG1 cells (Stratagene, La Jolla, Calif.) by incubation of 10 μl of the M13 with 90 μl of competent TG 1 cells at 0° C. for 30 min. and 42° C. for 75 sec. After being chilled to 0° C. for 2 min, 500 μl of 2XYT media was added to the cells and incubated for 10 min. at 37° C. Two hundred μl of growing nontransformed TG1 cells were mixed with the transformed TG1 cells, and to which 2.5 ml of soft agarose LB (42° C.) was added. The cell mixture was immediately poured onto preheated LB agar plates (40° C.), and incubated at 37° C. overnight. Phage clones were picked up for examination of the insertion of SAH hydrolase gene and the orientation through DNA sequencing and restriction enzyme analysis. The selected phage clone was used for preparation of single strand DNA template.

The M13 phage containing the SAH hydrolase gene were incubated with TG1 cells in 3 ml of 2×YT media overnight. One drop of the overnight culture was mixed with growing TG1 cells (in log phase) in 30 ml of 2XYT media. Cells were incubated for 8 hours with shaking. After centrifugation, the supernatant was collected for single-strand template DNA purification. The purification was conducted according to the manufacture's procedure provided by Amersham Life Science.

Design of Primers for Point Mutation

Oligonucleotides (15–30 bases) were synthesized by CruaChem (Sterling, Va.). The sequence of the oligonucleotides were designed to be complementary to the sequence in the region covering both sides of the mutation site. For example, to mutate lys 426 to glu 426, the oligonucleotides used as primer contained the following sequence:

GGCCCCTTCGAGCCGGATCACTACCGC (SEQ ID NO:4) where GAG codes for glu instead of original (wild type) AAG which codes for lys.

The selection of mutation sites was based on x-ray structure of the substrate binding site and coenzyme binding site of human SAH hydrolase (Turner, et al., *Nature Structural Biology*, 5:369–376 (1998)). Amino acid residues such as Thr 157, Asp 131, Hys 301, Lys 186, Asn 191, Glu 156, Asp 190, Phe 362, Phe 302, Asn 181, His 353, Glu 59, Ser 83, His 55, Leu 54, Cys 79, His 301, Arg 343, Asp 303, Leu 344, Asn 80, Asn 346, Asp 107 and entire C-terminal residues can be the mutagenesis targets (see Table 2 for particular mutations generated). The coenzyme binding domain contains residues from Tyr193-Asn346.

The oligonucleotides were dissolved in water to a concentration of 5 ng/μl. The oligonucleotide solution was then phosphorylated at the 5'-end using polynucleotide kinase. The phosphorylation reaction mixture contained the following materials: 2.5 μl of oligonucleotides (5 ng/μl), 3 μl of one-phor-all 10×kinase buffer (Pharmacia Biotech), 21.5 μl of water, 2 μl of 10 mM ATP, and 1 μl of polynucleotide kinase (100,000 U/ml) (Pharmacia Biotech). The reaction mixture was incubated at 37° C. for 30 min. followed by heating at 70° C. for 10 min. to inactivate the enzyme.

TABLE 1

Oligonucleotides used for site-directed mutagenesis of human SAH hydrolases

| | | SEQ ID No. | Fo/Re |
|---|---|---|---|
| K186A | GACTTCGTCACCGCCAGCAAGTTTGGG | 5 | Fo |
| K186A | CCCAAACTTGCTGGCGGTGACGAAGTC | 6 | Re |
| F302S | AACATTGGACACTCTGACGTGGAGATC | 7 | Fo |
| F302S | GATCTCCACGTCAGAGTGTCCAATGTT | 8 | Re |

TABLE 1-continued

Oligonucleotides used for site-directed mutagenesis of human SAH hydrolases

| | | SEQ ID No. | Fo/Re |
|---|---|---|---|
| H301D | TGTAACATTGGAGACTTTGACGTGGAG | 9 | Fo |
| H301D | CTCCACGTCAAAGTCTCCAATGTTACA | 10 | Re |
| H353S | TGTGCCATGGGCTCCCCCAGCTTCGTG | 11 | Fo |
| H353S | CACGAAGCTGGGGGAGCCCATGGCACA | 12 | Re |
| R343A | CTGGCCGAGGGTGCGCTGGTCAACCTG | 13 | Fo |
| R343A | CAGGTTGACCAGCGCACCCTCGGCCAG | 14 | Re |
| D190A | AAGAGCAAGTTTGCCAACCTCTATGGC | 15 | Fo |
| D190A | GCCATAGAGGTTGGCAAACTTGCTCTT | 16 | Re |
| F82A | AGCTGCAACATCGCCTCCACCCAGGAC | 17 | Fo |
| F82A | GTCCTGGGTGGAGGCGATGTTGCAGCT | 18 | Re |
| N181D | GCCATCAATGTGGACGACTCCGTCACC | 19 | Fo |
| N181D | GGTGACGGAGTCGTCGACATTGATGGC | 20 | Re |
| R431A | CCGGATCACTACGCCTACTGAGAATTC | 21 | Fo |
| R431A | GAATTCTCAGTAGGCGTAGTGATCCGG | 22 | Re |
| K426R | GATGGCCCCTTCCGCCCGGATCACTAC | 23 | Fo |
| K426R | GTAGTGATCCGGGCGGAAGCCATCACA | 24 | Re |
| C195S | AACCTCTATGGCTCCCGGGAGTCCCTC | 25 | Fo |
| C195S | GAGGGACTCCCGGGAGCCATAGAGGTT | 26 | Re |
| Δ432 | GATCACTACCGCTGATGAGAATTCGAG | 27 | Fo |
| Δ432 | CTCGAATTCTCATCAGCGGTAGTGATC | 28 | Re |

The mutagenized codon is underlined, and the nucleotides changed are in boldface type.
Fo: forward oligonucleotide
Ro: backward oligonucleotide

TABLE 2

Additional oligonucleotides used for site-directed mutagenesis of human SAH hydrolases

| Mutant | Sequence | SEQ ID No. | Fo/Re |
|---|---|---|---|
| Glu156Ala | GGCATCTCTGAGGCGACCACGACTGGG | 29 | Fo |
| Glu156Ala | CCCAGTCGTGGTCGCCTCAGAGATGCC | 30 | Re |
| Glu156Asp | GGCATCTCTGAGGACACCACGACTGGG | 31 | Fo |
| Glu156Asp | CCCAGTCGTGGTGTCCTCAGAGATGCC | 32 | Re |
| Asp131Lys | CTCAACATGATTCTGGACAAGGGGGGCGACCTCACC | 33 | Fo |
| Asp131Lys | GGTGAGGTCGCCCCCCTTGTCCAGAATCATGTTGAG | 34 | Re |
| Asp131Asn | CTCAACATGATTCTGGACAACGGGGGCGACCTCACC | 35 | Fo |
| Asp131Asn | GGTGAGGTCGCCCCCGTTGTCCAGAATCATGTTGAG | 36 | Re |
| Lys186Ala | GACTCCGTCACCGCGAGCAAGTTTGAC | 37 | Fo |
| Lys186Ala | GTCAAACTTGCTCGCGGTGACGGAGTC | 38 | Re |
| Lys186Asp | GACTCCGTCACCGACAGCAAGTTTGAC | 39 | Fo |
| Lys186Asp | GTCAAACTTGCTGTCGGTGACGGAGTC | 40 | Re |
| His55Pro | GCTGGCTGCCTGCCCATGACCGTGGAGACG | 41 | Fo |
| His55Pro | CGTCTCCACGGTCATGGGCAGGCAGCCAGC | 42 | Re |
| Arg343Ala | CTGCTGGCCGAGGGTGCGCTGGTCAACCTG | 43 | Fo |
| Arg343Ala | CAGGTTGACCAGCGCACCCTCGGCCAGCAG | 44 | Re |
| Asp303Glu | GTGTGTAACATTGGACACTTTGAGGTGGAGATCGATGTC | 45 | Fo |
| Asp303Glu | GACATCGATCTCCACCTCAAAGTGTCCAATGTTACACAC | 46 | Re |
| Phe302Ile | GTGTGTAACATTGGACACATTGACGTGGAGATC | 47 | Fo |
| Phe302Ile | GATCTCCACGTCAATGTGTCCAATGTTACACAC | 48 | Re |
| Leu344Gly | GCCGAGGGTCGGGGGGTCAACCTGGGTTGTGCC | 49 | Fo |
| Leu344Gly | GGCACAACCCAGGTTGACCCCCCGACCCTCGGC | 50 | Re |

TABLE 2-continued

Additional oligonucleotides used for site-directed mutagenesis of human SAH hydrolases

| Mutant | Sequence | SEQ ID No. | Fo/Re |
|---|---|---|---|
| Phe82Ser | CAGTGGTCCAGCTGCAACATCTCCTCCACCCAGGAC | 51 | Fo |
| Phe82Ser | GTCCTGGGTGGAGGAGATGTTGCAGCTGGACCACTG | 52 | Re |
| Thr159Ser | GAGGAGACCACGTCCGGGGTCCACAACCTC | 53 | Fo |
| Thr159Ser | GAGGTTGTGGACCCCGGACGTGGTCTCCTC | 54 | Re |
| Asn346Gly | GGTCGGCTGGTCGGCCTGGGTTGTGCC | 55 | Fo |
| Asn346Gly | GGCACAACCCAGGCCGACCAGCCGACC | 56 | Re |
| Asn346Asp | GGTCGGCTGGTCGACCTGGGTTGTGCC | 57 | Fo |
| Asn346Asp | GGCACAACCCAGGTCGACCAGCCGACC | 58 | Re |
| Cys79Ala | GTGCAGTGGTCCAGCGCCAACATCTTCTCCACC | 59 | Ro |
| Cys79Ala | GGTGGAGAAGATGTTGGCGCTGGACCACTGCAC | 60 | Re |
| Cys79Gly | GTGCAGTGGTCCAGCGGCAACATCTTCTCCACC | 61 | Fo |
| Cys79Gly | GGTGGAGAAGATGTTGCCGCTGGACCACTGCAC | 62 | Re |
| His301Ala | GTGTGTAACATTGGAGCCTTTGACGTGGAG | 63 | Fo |
| His301Ala | CTCCACGTCAAAGGCTCCAATGTTACACAC | 64 | Re |
| Asp303Ala | GTGTGTAACATTGGACACTTTGCCGTGGAGATCGATGTC | 65 | Fo |
| Asp303Ala | GACATCGATCTCCACGGCAAAGTGTCCAATGTTACACAC | 66 | Re |
| Thr158Tyr | ATCTCTGAGGAGACCTATACTGGGGTCCACAAC | 67 | Fo |
| Thr158Tyr | GTTGTGGACCCCAGTATAGGTCTCCTCAGAGAT | 68 | Re |
| Thr159Tyr | ATCTCTGAGGAGACCACGTATGGGGTCCACAAC | 69 | Fo |
| Thr159Tyr | GTTGTGGACCCCATACGTGGTCTCCTCAGAGAT | 70 | Re |

Fo: forward oligonucleotide
Ro: backward oligonucleotide.

TABLE 3

Additional oligonucleotides used for site-directed mutagenesis of human SAH hydrolases

| Mutant | Sequence | SEQ ID No. | Fo/Re |
|---|---|---|---|
| L347F | GGTCGGCTGGTCAACTTTGGTTGTGCCATG | 71 | Fo |
| L347F | CATGGCACAACCAAAGTTGACCAGCCGACC | 72 | Re |
| R38E | ATGCGTATGCGGGAGGAATACTCGGCCTCC | 73 | Fo |
| R38E | GGAGGCCGAGTATTCCTCCCGCATACGCAT | 74 | Re |
| C53S | GCCCGCATCGCTGGCTCTCTGCACATGACC | 75 | Fo |
| C53S | GGTCATGTGCAGAGAGCCAGCGATGCGGGC | 76 | Re |
| T57G | GGCTGCCTGCACATGGGGGTGGAGACGGCC | 77 | Fo |
| T57G | GGCCGTCTCCACCCCCATGTGCAGGCAGCC | 78 | Re |
| E59D | CTGCACATGACCGTGGATACGGCCGTCCTC | 79 | Fo |
| E59D | GAGGACGGCCGTATCCACGGTCATGTGCAG | 80 | Re |
| T57S | GGCTGCCTGCACATGTCTGTGGAGACGGCC | 81 | Fo |
| T57S | GGCCGTCTCCACAGACATGTGCAGGCAGCC | 82 | Re |
| L347Y | GGTCGGCTGGTCAACTATGGTTGTGCCATG | 83 | Fo |
| L347Y | CATGGCACAACCATAGTTGACCAGCCGACC | 84 | Re |
| L347I | GGTCGGCTGGTCAACATTGGTTGTGCCATG | 85 | Fo |
| L347I | CATGGCACAACCAATGTTGACCAGCCGACC | 86 | Re |
| S83G | TGCAACATCTTCGGTACCCAGGACCATGCG | 87 | Fo |
| S83G | TGCAACATCTTCGGTACCCAGGACCATGCG | 88 | Re |
| L54G | GCCCGCATCGCTGGCTGCGGTCACATGACC | 89 | Fo |
| L54G | GGTCATGTGACCGCAGCCAGCGATGCGGGC | 90 | Re |
| Y100T | GGCATTCCGGTGACTGCCTGGAAGGGCGAA | 91 | Fo |
| Y100T | TTCGCCCTTCCAGGCAGTCACCGGAATGCC | 92 | Re |
| K121A | ACCCTGTACTTCGCTGACGGGCCCCTCAAC | 93 | Fo |
| K121A | GTTGAGGGGCCCGTCAGCGAAGTACAGGGT | 94 | Re |
| N191A | AGCAAGTTTGACGCTCTCTATGGCTGCCGG | 95 | Fo |
| N191A | CCGGCAGCCATAGAGAGCGTCAAACTTGCT | 96 | Re |
| M351A | CTGGGTTGTGCCGCTGGCCACCCCAGCTTC | 97 | Fo |
| M351A | GAAGCTGGGGTGGCCAGCGGCACAACCCAG | 98 | Re |
| H353R | CTGGGTTGTGCCATGGGCCGTCCCAGCTTC | 99 | Fo |
| H353R | GAAGCTGGGACGGCCCATGGCACAACCCAG | 100 | Re |
| F362S | TTCGTGATGAGTAACTCCAGTACCAACCTG | 101 | Fo |
| F362S | CTGGTTGGTACTGGAGTTACTCATCACGAA | 102 | Re |
| D131E | ATGATTCTGGACGAAGGGGGCGACCTCACC | 103 | Fo |
| D131E | GGTGAGGTCGCCCCCTTCGTCCAGAATCAT | 104 | Re |
| T157G | ATCTCTGAGGAGGGTACGACTGGGGTCCAC | 105 | Fo |
| T157G | GTGGACCCCAGTCGTACCCTCCTCAGAGAT | 106 | Re |
| N80G | TGGTCCAGCTGCGGTATCTTCTCCACCCAG | 107 | Fo |
| N80G | CTGGGTGGAGAAGATACCGCAGCTGGACCA | 108 | Re |
| D134E | ATGATTCTGGACGACGGGGGCGAACTCACC | 109 | Fo |
| D134E | GGTGAGTTCGCCCCCGTCGTCCAGAATCAT | 110 | Re |
| E155G | ATCTCTGGTGAGACCACGACTGGGGTCCAC | 111 | Fo |
| E155G | GTGGACCCCAGTCGTGGTCTCACCAGAGAT | 112 | Re |
| N181A | GCCATCAATGTCGCTGACTCCGTCACCAAG | 113 | Fo |
| N181A | CTTGGTGACGGAGTCAGCGACATTGATGGC | 114 | Re |
| L214A | ATGATTGCCGGCGCTGTAGCGGTGGTAGCA | 115 | Fo |
| L214A | TGCTACCACCGCTACAGCGCCGGCAATCAT | 116 | Re |
| Y221S | GTGGTAGCAGGCTCTGGTGATGTGGGCAAG | 117 | Fo |
| Y221S | CTTGCCCACATCACCAGAGCCTGCTACCAC | 118 | Re |
| K226A | GGTGATGTGGGCGCTGGCTGTGCCCAGGCC | 119 | Fo |
| K226A | GGCCTGGGCACAGCCAGCGCCCACATCACC | 120 | Re |
| F235S | GCCCTGCCGGGTTCTGGAGCCCGCGGTCATC | 121 | Fo |
| F235S | GATGACCGCGGGCTCCAGAACCCCGCAGGGC | 122 | Re |
| I240L | GGAGCCGCGTCCTTATCACCGAGATTGAC | 123 | Fo |
| I240L | GTCAATCTCGGTGATAAGGACGCGGGCTCC | 124 | Re |
| N248A | ATTGACCCCATCGCTGCACTGCAGGCTGCC | 125 | Fo |
| N248A | GGCAGCCTGCAGTGCAGCGATGGGGTCAAT | 126 | Re |
| D263G | GTGACCACCATGGGTGAGGCCTGTCAGGAG | 127 | Fo |
| D263G | CTCCTGACAGGCCTCACCCATGGTGGTCAC | 128 | Re |
| G269D | GAGGCCTGTCAGGAGGATAACATCTTTGTC | 129 | Fo |
| G269D | GACAAAGATGTTATCCTCCTGACAGGCCTC | 130 | Re |
| R285D | GACATCATCCTTGGCGATCACTTTGAGCAG | 131 | Fo |
| R285D | CTGCTCAAAGTGATCGCCAAGGATGATGTC | 132 | Re |
| D292G | CAGATGAAGGGTGATGCCATTGTGTGTAAC | 133 | Fo |
| D292G | GTTACACACAATGGCATCACCCTTCATCTG | 134 | Re |
| H301T | AACATTGGAACTTTTGACGTGGAGATCGAT | 135 | Fo |
| H301T | ATCGATCTCCACGTCAAAAGTTCCAATGTT | 136 | Re |
| K309R | GAGATCGATGTCAGATGGCTCAACGAGAAC | 137 | Fo |
| K309R | GTTCTCGTTGAGCCATCTGACATCGATCTC | 138 | Re |
| K322G | GTGAACATCGGTCCGCAGGTGGACCGGTAT | 139 | Fo |
| K322G | ATACCGGTCCACCTGCGGACCGATGTTCAC | 140 | Re |
| R329A | GACCGGTATGCTTTGAAGAATGGGCGCCGC | 141 | Fo |
| R329A | GCGGCGCCCATTCTTCAAAGCATACCGGTC | 142 | Re |
| S361G | ATGAGTAACGTTTCACCAACCAGGTGATG | 143 | Fo |
| S361G | CATCACCTGGTTGGTGAAACGTTACTCAT | 144 | Re |

TABLE 3-continued

Additional oligonucleotides used for site-directed mutagenesis of human SAH hydrolases

| Mutant | Sequence | SEQ ID No. | Fo/Re |
|---|---|---|---|
| Y379S | CATCCAGACAAGTCTCCCGTTGGGGTTCAT | 145 | Fo |
| Y379S | ATGAACCCCAACGGGAGACTTGTCTGGATG | 146 | Re |
| L386A | GGGGTTCATTTCGCTCCCAAGAAGCTGGAT | 147 | Fo |
| L386A | ATCCAGCTTCTTGGGAGCGAAATGAACCCC | 148 | Re |
| K388G | CATTTCCTGCCCGGTAAGCTGGATGAGGCA | 149 | Fo |
| K388G | TGCCTCATCCAGCTTACCGGGCAGGAAATG | 150 | Re |
| H398A | GCAGTGGCTGAAGCCGCTCTGGGCAAGCTG | 151 | Fo |
| H398A | CAGCTTGCCCAGAGCGGCTTCAGCCACTGC | 152 | Re |
| K401R | CACCTGGGCCGTCTGAATGTGAAGTTGACC | 153 | Fo |
| K401R | GGTCAACTTCACATTCAGACGGCCCAGGTG | 154 | Re |
| K401D | CACCTGGGCGATCTGAATGTGAAGTTGACC | 155 | Fo |
| K401D | GGTCAACTTCACATTCAGATCGCCCAGGTG | 156 | Re |
| T407S | AATGTGAAGTTGTCTAAGCTAACTGAGAAG | 157 | Fo |
| T407S | CTTCTCAGTTAGCTTAGACAACTTCACATT | 158 | Re |
| L409G | GTGAAGTTGACCAAGGGTACTGAGAAGCAA | 159 | Fo |
| L409G | TTGCTTCTCAGTACCCTTGGTCAACTTCAC | 160 | Re |
| S420T | TACCTGGGCATGACTTGTGATGGCCCCTTC | 161 | Fo |
| S420T | GAAGGGGCCATCACAAGTCATGCCCAGGTA | 162 | Re |
| P424A | TCCTGTGATGGCGCTTTCAAGCCGGATCAC | 163 | Fo |
| P424A | GTGATCCGGCTTGAAAGCGCCATCACAGGA | 164 | Re |
| F425S | TGTGATGGCCCCTCTAAGCCGGATCACTAC | 165 | Fo |
| F425S | GTAGTGATCCGGCTTAGAGGGGCCATCACA | 166 | Re |
| D428G | TGTGATGGCCCCTTCAAGCCGGGTCACTAC | 167 | Fo |
| D428G | GTAGTGACCCGGCTTGAAGGGGCCATCACA | 168 | Re |
| P427A | TGTGATGGCCCCTTCAAGGCTGATCACTAC | 169 | Fo |
| P427A | GTAGTGATCAGCCTTGAAGGGGCCATCACA | 170 | Re |
| H429A | TGTGATGGCCCCTTCAAGCCGGATGCTTAC | 171 | Fo |
| H429A | GTAAGCATCCGGCTTGAAGGGGCCATCACA | 172 | Re |
| Y430T | GGCCCCTTCAAGCCGGATCACACTCGCTAC | 173 | Fo |
| Y430T | GTAGCGAGTGTGATCCGGCTTGAAGGGGCC | 174 | Re |
| R431K | GGCCCCTTCAAGCCGGATCACTACAAATAC | 175 | Fo |
| R431K | GTATTTGTAGTGATCCGGCTTGAAGGGGCC | 176 | Re |
| R431G | GGCCCCTTCAAGCCGGATCACTACGGTTAC | 177 | Fo |
| R431G | GTAACCGTAGTGATCCGGCTTGAAGGGGCC | 178 | Re |
| Y432S | CCCTTCAAGCCGGATCACTACCGCTCTTGA | 179 | Fo |
| Y432S | TCAAGAGCGGTAGTGATCCGGCTTGAAGGG | 180 | Re |
| Y432A | CCCTTCAAGCCGGATCACTACCGCGCTTGA | 181 | Fo |
| Y432A | TCAAGCGCGGTAGTGATCCGGCTTGAAGGG | 182 | Re |
| Y432F | CCCTTCAAGCCGGATCACTACCGCTTTTGA | 183 | Fo |
| Y432F | TCAAAAGCGGTAGTGATCCGGCTTGAAGGG | 184 | Re |

Fo: forward oligonucleotide
Re: backward oligonucleotide

The 5'-phosphorylated oligonucleotides DNA was annealed with single-stranded DNA (M13 phage containing wild type human SAH hydrolase gene, 1 µg/l) in a ratio of oligonucleotide: template of 2:1 in annealing buffer. The annealing reaction was performed by incubating the annealing mixture at 70° C. for 3 min. followed by 30 min. at 37° C. or followed by transferring the micro centrifuge tube to a 55° C. beaker and then allowed to cool to room temperature. To the annealing mixture (17 µl), 19 µl of dNTP A (α-S) mix, 1.5 µl of T7 DNA polymerase (0.8 units), and 2.5 µl of T4 DNA ligase (92.5 units), and 6 µl of water were added. After 10 min. at room temperature and 30 min. at 37° C., the reaction was stopped by heat inactivation at 70° C. for 15 min. To the reaction mixture was added T5 exonuclease (2000 units) and exonuclease buffer to remove single-strand non-mutant DNA at 37° C. for 30 min. followed by 15 min. of heat inactivation at 70° C. NciI (5 units) was added to the reaction mixture to nicking the non-mutant strand by incubating NciI at 37° C. for 90 min. The non-mutant strand was digested by adding 160 units of Exonuclease III and incubating at 37° C. for 30 min. followed by heat inactivation. To repolymerize the gaped DNA, dNTP mix B and 3.5 units of DNA polymerase 1 and 2.5 units of T4 DNA ligase were added to the reaction mixture, and incubated at 37° C. for 1 h.

The M13 plasmid containing the mutated SAH hydrolase gene was then transferred into competent TG 1 host cells by heat shock method or an electroporation method. Ten µl of the mutant M13 plasmid was added to 90 µl of water and mixed with competent TG1 cells in ice for 40 min. The TG1 cells were shocked by incubation at 42° C. for 45 sec. and immediately at 0° C. for 5 min. The transferred TG1 cells were allowed to return to room temperature, and mixed with 200 µl of growing non-transferred TG1 cells (served as lawn cells). Three ml of molten Htop agar was added and mixed followed by immediately pouring the cells onto a L plate. The plate was incubated in 37° C. for overnight. Phage plaques formed were picked by sterile tooth pick and swirling in a tube containing 3 ml of 2XYT medium. After overnight culture, cells were collected by centrifugation, and the double-strand M13 plasmid from the cells was purified by using Promega DNA purification kit (Wizard plus Minipreps).

The supernatant from centrifugation was used to purify single-strand M13 DNA. The mutation was confirmed by DNA sequencing of the single-strand M13 DNA using Sequenase Version 2.0 (Unites States Biochemical). The double-strand M13 DNA containing correct mutation sequence was selected, and digested with EcoR I. The EcoR I fragment containing the mutant SAH hydrolase gene was purified by agarose electrophoresis followed by gene cleaning using Qlaquick Gel Extraction kit (Qiagen, Valencia, Calif.). The purified EcoR I fragment was subcloned into pKK223-3 expression vector using T4 ligase. Two µl of EcoR 1 treated and 5'-dephosphorylated pKK223-3 vector backbone was incubated with 10 µl of the purified mutant insert DNA in a backbone to insert ratio of 2:1. The ligation reaction was carried out in One-phore-All buffer containing 0.01 M ATP at 16C overnight. The ligated vector containing mutant SAH hydrolase gene was transferred into competent E. Coli JM109 cells by heat shock method. The transformed cells were selected against 100 µl/ml ampicillin. Ampicillin-resistant clones were picked and grown in 10 ml of 2×YT medium containing 35 µl/ml ampicillin for 2 hours at 37° C. and then induced with 1 mM isopropyl-1-thio-β-D-galactopyranoside (IPTG) and grown overnight at 37° C. The cells were harvested by centrifugation, and suspended in 0.8 ml of 50 mM Tri-HCl, pH 7.5, containing 2 mM EDTA. Cells were lysed by rapid freezing and thawing. After centrifugation at 13,500 rpm for 1 hour at 4° C., the supernatant was collected for SDS-PAGE analysis for over-expression of SAH hydrolase mutant protein. A heavy protein band at molecular size of 47,000 Da indicates the overexpression of mutant SAH hydrolase protein.

PCR-Based Mutagenesis Method

PCR-based mutagenesis was performed using the ExSite PCR-based Site-Directed Mutagenesis Kit (Stratagene, La Jolla, Calif.). The ExSite method uses increased template concentration and <10 PCR cycles. The resulting mixture of template DNA, newly synthesized DNA and hybrid parental/newly synthesized DNA is treated with Dpn I and Pfu DNA polymerase. Dpn I digests the in vivo methylated parental template and hybrid DNA, and Pfu DNA polymerase polishes the ends to create a blunt-ended PCR product. The end-polished PCR product is then intramolecularly ligated together and transformed into E. coli cells. The detailed experimental procedure is described as follows:

To a microcentrifuge tube were added 0.5 pmol of template DNA, 2.5 µl of 10×mutagenesis buffers, 1 µl of 25 mM dNTP mix, 15 pmol of each primer, and ddH$_2$O to a final volume of 24 µl. To the reaction mixture was then added 1 µl of ExSite DNA polymerase blend (5 U/µl). The reaction solution was overlayed with 20 µl of mineral oil and thermal cycle the DNA using 7012 amplification cycles. The cycling parameters are listed in Table 10.

TABLE 3

Mutagenesis Cycling Parameters

| Segment | Cycles | Temperature | Time |
|---|---|---|---|
| 1 | 1 | 94° C. | 4 min. |
|  |  | 50° C. | 2 min. |
|  |  | 72° C. | 2 min. |
| 2 | 8 | 94° C. | 1 min. |
|  |  | 56° C. | 2 min. |
|  |  | 72° C. | 1 min. |
|  |  | 72° C. | 5 min. |
| 3 |  | 72° C. | 5 min. |

Following amplification, the reaction tube was placed on ice for 2 min. to cool the reaction to <37° C. To the reaction tube were added 1 µl of the Dpn I restriction enzyme (10 U/µl) and 0.5 µl of cloned Pfu DNA polymerase (2.5 U/µl) followed by incubation at 37° C. for 30 min. The reaction was stopped by heating at 72° C. for 30 min. For ligating the product, to the reaction tube were added 100 µl of ddH$_2$O, 10 µl of 10×mutagenesis buffer, and 5 µl of 10 mM rATP. Transfer 10 µl of the above reaction mixture to a new micocentrifuge tube and add 1 µl of T4 DNA ligase (4 U/µl). The ligation was incubated at 37° C. for 1 hour. 2 µl of the ligated DNA was added to 80 µl of Epicurian Coli XL1-Blue supercompetent cells on ice and incubated for 30 min. followed by 45 seconds at 42defendant and 2 min. on ice. The transformed cells were immediately plated on LB-ampicillin agar plates which had been spread with 20 µl of 10% X-gal prepared in DMF and 20 µl of 100 M IPTG in H$_2$O. The plate was incubated overnight at 37° C. The blue colonies were selected as colonies containing the mutagenized plasmid. The selected colonies were further confirmed by DNA sequencing. Protein overexpression and substrate trapping screening were performed as described above.

Double-strand pKK223-3 containing human SAH hydrolase (wild type) was purified from 50 ml of *E. coli* JM109 culture using Promega DNA purification kit (Wizard plus Minipreps). The purified plasmid was annealed with PCR primers containing the desired mutation sequence.

Deletion and insertion mutations were also performed according to the manufacture's protocol using ExSite PCR-based Site-directed Mutagenesis Kit. Double mutations or combinations of mutation and deletion or insertion were carried out using mutated or deleted DNA as template for secondary mutation or deletion using either M13-based mutagenesis or PCR-based mutagenesis methods.

Identification of Substrate Trapping SAH Hydrolase

The cell-free extracts from colonies that inducibly overexpressed mutant SAH hydrolase proteins were chromatographed on a monoQ column (HR5/5) equipped with FPLC system. Proteins were eluted with a linear gradient of NaCl from 0 to 1 M in 10 mM sodium phosphate buffer, pH 7.0 over 35 min. The major protein peak that eluted at the same or close retention time as that of the wild type SAH hydrolase was collected. An aliquot collected mutant SAH hydrolase (1–10 µg) was incubated with [$^3$H]SAH (10 mCi/mmole, 200 µM) and 30 µM of 5,5'-dithiobis (2-nitrobenzoic acid) (DTNB) at room temperature for 5–30 min.

The reaction solution was filtered through a membrane of molecular weight cut-off at 30,000 by centrifugation. The filtrate was measured at 412 nm for Hcy formation (enzyme activity) and the [$^3$H] radioactivity on the membrane was measured by scintillation counting after membrane washing with 1 ml of 50 mM phosphate buffer, pH 7.0.

The mutant hydrolases that show high radioactivity on the membrane and low O.D. at 412 nm of the filtrate relative to the wild type enzyme were selected as candidates for further characterization including determination of Km or Kd and binding energy (AG). Mutant SAH hydrolases with Km value lower than 10 µM toward SAH and kcat value lower than 0.1 per second were overexpressed in larger quantity (1–2 L of *E. coli* culture) and the enzyme proteins were purified to homogenous as judged by single band on SDA-PAGE.

Example 2

Large Scale Overexpression and Purification of Wild Type and Mutant Forms of SAH Hydrolases Purification The cell-free extract of IPTG-induced *E. Coli* JM109 (containing SAH hydrolase gene in pKK223-3 vector) culture was mixed with powder DEAE-cellulose (Sigma, St. Louis, Mo.) equilibrated with 0.1 M sodium phosphate buffer, pH 7.2 containing 1 mM EDTA (buffer A). The cell-free extract and DEAC-cellulose mixture was placed in a funnel and filtrated under vacuum. After washing with 3 volumes of buffer A, the filtrate was precipitated by solid ammonium sulfate (30–60%). The precipitated protein was collected by centrifugation at 13000 rpm, and resuspended in 50 mM sodium phosphate buffer, pH 7.2, containing 1 mM EDTA. The protein was chromatographed through a Sephacryl S-300 size exclusion column (2.5×100 cm) (Pharmacial Biotech, Piscataway, N.J.) followed by a DEAE-Sepharose ion exchange column (2.5×30 cm) eluted by a linear NaCl gradient. The major protein peak from DEAE-Sepharose was examined by SDS-PAGE. In most of the times, this purification procedure gave a single protein band on SDS-PAGE. Sometime, minor bands were observed on SDS-PAGE. In this case, rechromatography on DEAE-Sepharose column was performed to obtain pure protein. SAH hydrolase activity or [$^3$H]SAH binding affinity was also measured to confirm the protein peak.

Storage of the Purified SAH Hydrolase

The purified wild type and mutant SAH hydrolases were dialyzed against 5 mM sodium phosphate buffer, pH 7.0 for 6 hours at 4° C. The protein was then frozen in liquid nitrogen and lyophilized under vacuum. The lyophilized protein was stored at –70° C. The protein was stable for at least 2 years. The purified protein can also be stored in liquid containing 20% of glycerol at –20° C. For wild type enzyme, addition of 5 mole excess of adenosine (Ado) to the 20% glycerol solution stabilizes the enzyme activity even better.

Assays for Enzyme Activity

The assay of SAH hydrolase activity in the hydrolytic direction was performed as described in Yuan, et al., *J. Biol. Chem.*, 271:28008–28016, 1996). The assay measures the hydrolysis of SAH into Ado and Hcy. The reaction product Hcy was derivatized by thiol specific reagent DTNB for colometric determination at 412 nm. The assay for SAH hydrolase in the synthetic direction was measured by the formation of SAH from substrate Ado and Hcy using HPLC(see, Yuan, et al., *J. Biol. Chem.*, 268:17030–17037 (1993).

One unit of the enzyme activity was defined as the amount of enzyme that can hydrolyze or synthesize 1 μ mole of SAH/min/mg.

Assay for Binding Affinity (Kd)

Figure 5:
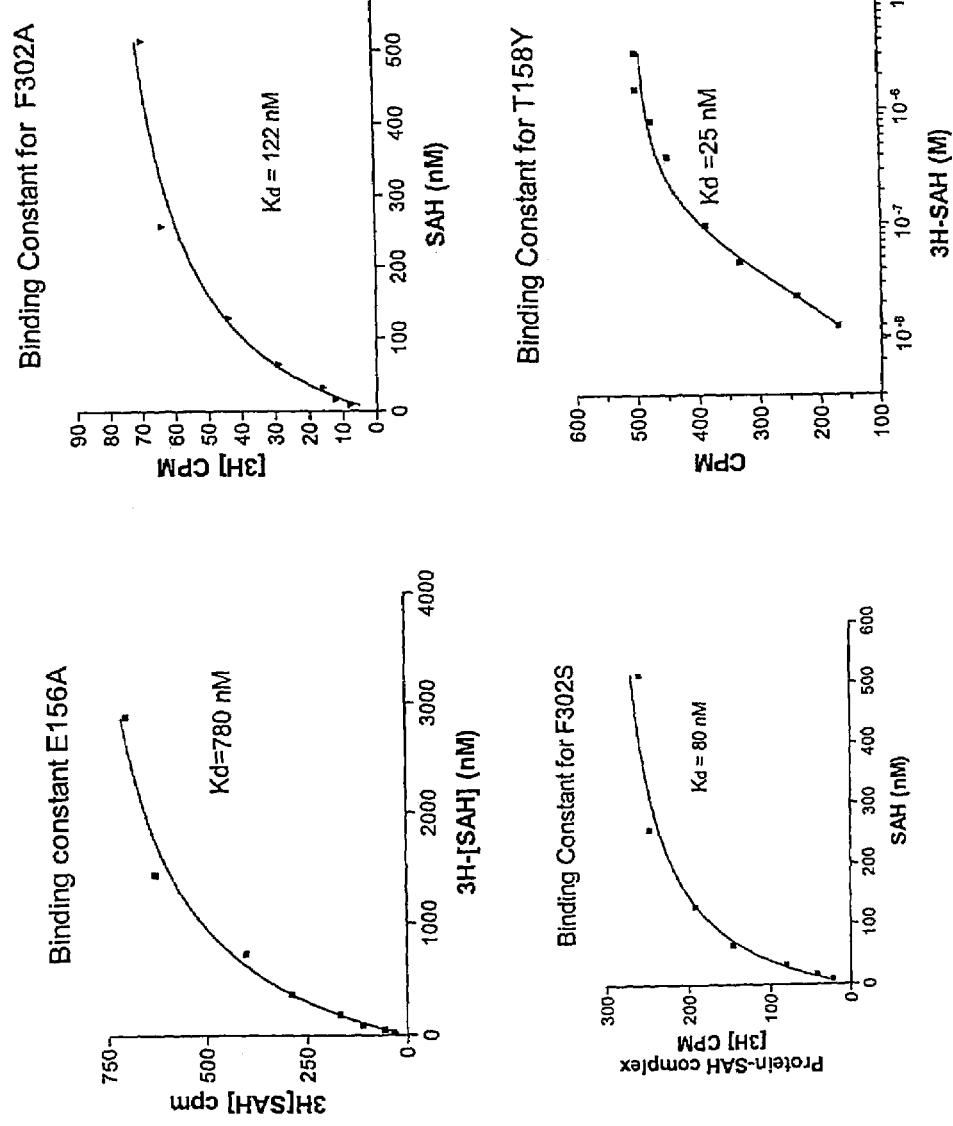
FIG. 5 shows Kd values for various SAH hydrolase mutants.

For mutant enzyme that completely lacks activity, the binding constant (Kd) values were determined by an equilibrium dialysis technique using [$^3$H] SAH and Spectrum 5-cell Equilibrium Dialyzer) (Spectrum, Houston, Tex.). The membrane disc used had molecular cut-off of 25,000. Kd values for several exemplary SAH hydrolase mutant enzymes are shown in FIG. 5.

Example 3

Preparation of Reagents

Preparation of Fluorophore-Labeled Ado and SAH Analogs

Method 1

Ado-5'-carboxylic acid (Sigma, St. Louis, Mo.) was derivatized with 9-(hydroxylmethyl)anthracene (HMA) (Fluka, Buchs, Switzerland). To 10 mg of Ado-5'-carboxylic acid dissolved in 100 ml of chloroform (10 min sonication) was added 50 mg 1-hydroxybenzotriazole (HOBT) (Janssen Chimica, Beerse, Belgium). After evaporation to dryness under nitrogen, 300 mg of N-ethyl-N'-(3-dimethylaminopropyl)carbodiimide hydrochloride in 300 ml chloroform and 5 ml of triethylamine were added. The resulting solution was kept at 0° C. for 30 min. To the above reaction mixture was added 200 mg HMA in 100 ml of chloroform. The mixture was allowed to stand at room temperature for 10 min. and then evaporated to dryness under a stream of nitrogen. The residue obtained was dissolved in 10 ml of HPLC mobile phase (methanol-water mixture, 90:10, w/w). One ml of the above solution was injected into a semi-preparative column (Econosphere, C18, 7×300 mm, Alltech, Dearfield, Ill.). The column was eluted with an isocratic method. The flow rate was 2 ml/min. The peaks were monitored at UV260 nm and fluorescence at Ex-365 nm, Em-415 nm. The peaks with UV and fluorescence absorbance were collected as HMA-labeled Ado-5'-ester.

Method 2

Ado-5'caroboxylic acid and 4-bromomethyl-7-methoxycoumarin (Br-Mmc) (Sigma, St. Louis, Mo.) were dissolved in ethyl acetate in a molar ratio of 1:3. The reaction volume was 25 ml. After addition of 2 g of finely powdered $K_2CO_3$ the solution was refluxed for 1 hour using a ml-reluxer. After cooling, the reaction solution was injected into a C18 column (Econosphere, C18, 7×300 mm, Alltech, Deerfield, Ill.) for HPLC separation. The elution was monitored by UV (260 nm) and fluorescence (Em 328 nm and Ex390 nm). The elution was performed in a linear gradient of methanol:water from 20 to 100% over 30 min. The flow rate was 2 ml/min.

Method 3

Figure 3:
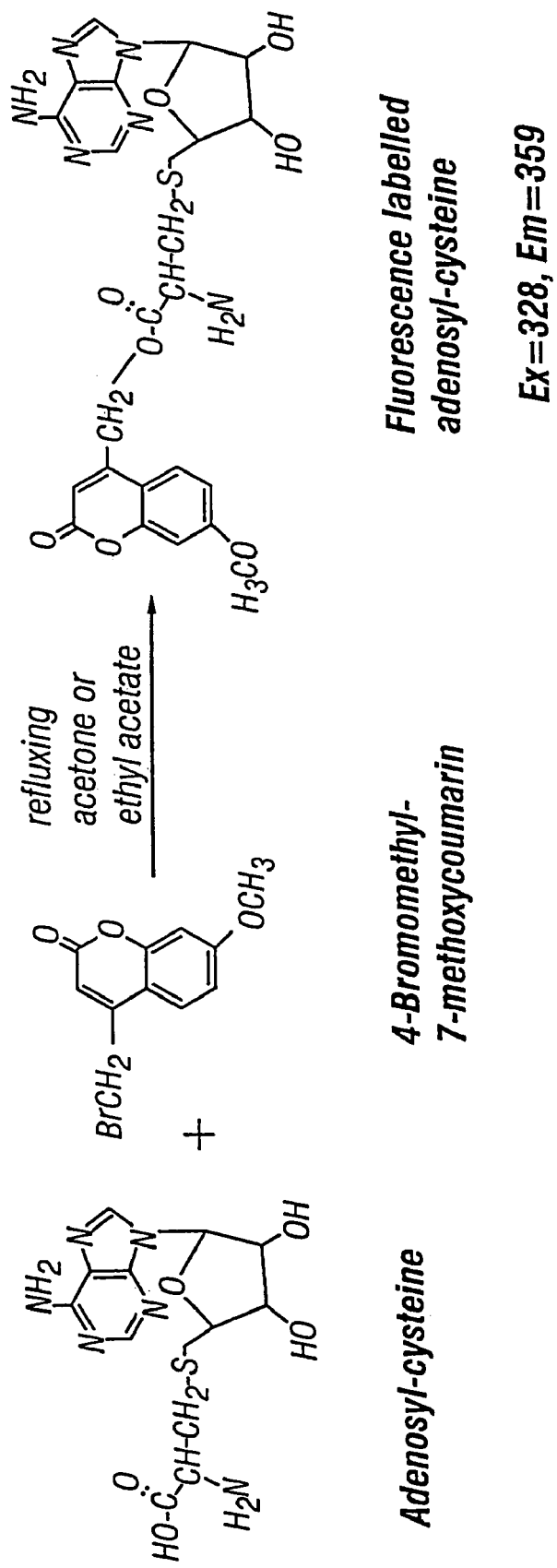
FIG. 3 depicts design and synthesis of fluorescence labeled tracer.
Figure 4:
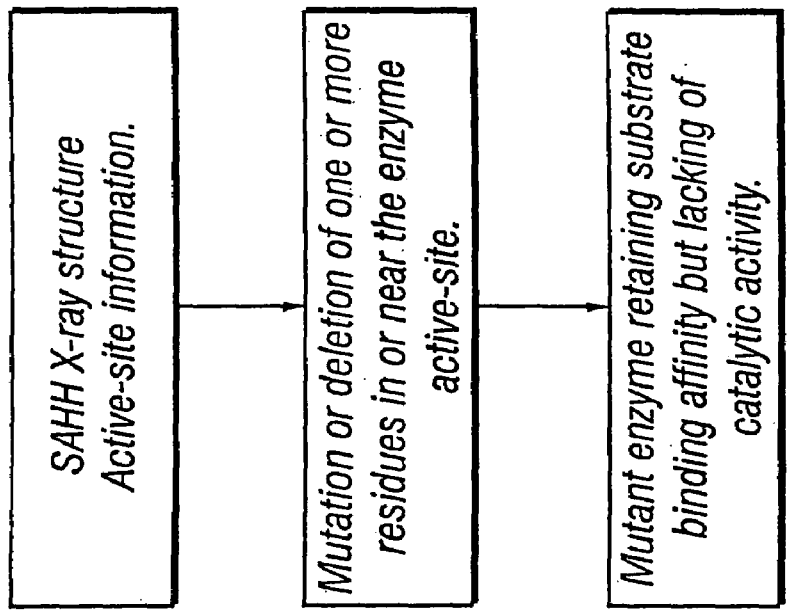
FIG. 4 depicts selection of mutant SAH hydrolase that lacks catalytic activity but retains substrate binding affinity.
Figure 4:
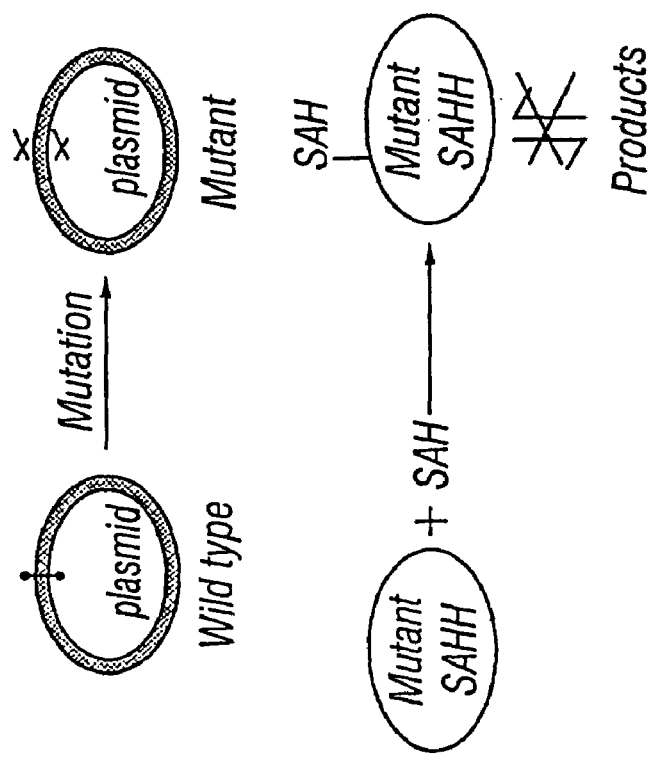

This method is depicted in FIG. 3. Adenosyl-L-cysteine (Ado-Cys) and 4-Bromomethyl-7-methoxycoumarin (Br-Mmc) were dissolved in ethyl acetate in a molar ration of 1:3. The final volume was 25 ml (ca, 1 mg Ado-Cys). After addition of 200 mg of finely powdered $K_2CO_3$, the solution was refluxed for 1 hour using a ml-refluxer at 80° C. After cooling, the reaction solution was injected into a C18 column (Econosphere, C18, 7×300 mm, Alltech, Dearfield, Ill.) for separation using HPLC. The fluorescently labeled Ado-Cys was eluted by a linear gradient of methanol; water from 20 to 100% in 30 min. The flow rate was 2 ml/min.

Method 4

Ado-Cys was dissolved in carbonate buffer, pH 9.0 in 1 mM concentration. Fluorescein isotiocyanate (FITC) (PcPierce, Rockford, Ill.) was dissolved in DMSO in 5 mM concentration, and diluted to 1 mM with carbonate buffer, pH 9.0. Equal volumes of Ado-Cys and FITC in carbonate buffer were mixed and incubated in room temperature for 1 hour. The Ado-Cys-FITC conjugate was then isolated by HPLC using a C18 column (Econsphere, C18, Alltech, Deerfield, Ill.). The elution was monitored at UV 260 nm and fluorescence at Ex484 nm and Em520 nm. The mobile phases were water and methanol in a linear gradient from 0 to 80% of methanol in 35 min.

Coating Mutant SAH Hydrolase on Microtiter Well (96 Well Plate)

Mutant SAH hydrolase (F302S) was coated on flat-bottomed 96 well plate (Dynex Technologies, Chantilly, Va.). 200 μl of 20 μg/ml of F302S mutant hydrolase in 50 mM sodium phosphate buffer, pH 7.6. was added to each well. After incubation at 4° C. overnight, the plate was emptied by inversion. After blocking with 0.5% BSA, the plate was then washed three times with 10 mM PBS containing 0.1 NaCl and 0.05% of Tween 20. After inversion and tapping, the plate was stored at 4° C. before use.

Preparation of Standard Samples and Chemical Reagents

1. Construction of a Standard Hcy Curve

Human albumin (Fraction V powder, Sigma) was dissolved in PBS in a protein concentration equal to that of human plasma. To 10 ml of the albumin was added 4 ml of 1% tri-n-butylphosphine (TBP). The mixture was incubated at room temperature for 15 min. followed by gel filtration through a size exclusion column (Sephacryl-S100, 2×90 cm). The albumin protein concentration was normalized to human plasma concentration using protein concentrator (Bio-Rad). The protein concentration was determined by Bradford reagent (Bio-Rad). A series of known concentration of L-homocysteine and L-homocystine were spiked into the TBP-treated human albumin in a final concentrations ranging from 0 to 50 μM. After incubation at 37° C. for 1 hour, the L-homocysteine spiked albumin and L-homocystine albumin were aliquoted in 70 μl/tube as standard samples, and stored at −20° C. before use.

2. Wild Type SAH Hydrolase Solution

The wild type SAH hydrolase (20 mU/50 μl) was dissolved in 50 mM phosphate buffer, Ph 7.2, containing 1 mM EDTA, 0.25 mM Ado and 1 mg/ml of BSA.

3. Tri-n-Butylphosphine (TBP) Solution

Tri-n-butylphoshine (Sigma) was dissolved in dimethylformamide (DMF) to 1% concentration.

4. Fluorophore-Labeled Ado-Cys Solution

Br-Mmc-labeled Ado-Cys or FITC-labeled Ado-Cys was dissolved in 50 mM phosphate buffer, pH 7.2, in a concentration of 0.5 mM.

5. SAH Hydrolase Inhibitor Solution

Neplanocin A (natural product), an inhibitor of SAH hydrolase, and a substrate of adenosine deaminase, was dissolved in 50 mM phosphate buffer, pH 7.2. The inhibitor solution (50 μM) was used in an enzyme to inhibitor ratio of 1:1.5.

6. Multi-Enzyme Solution

Adenosine (0.2 U/μl), nucleoside phosphorylase (0.2 U/l) and xanthine oxidase (0.2 U/μl) were dissolved in 50 mM potassium phosphate buffer, pH 7.2. All the enzymes were from Sigma.

7. Washing Solution

The plate washing solution contains of 10 mM PBS, pH 7.2, 0.1 M NaCl, and 0.05% Tween 20.

Example 4

Assays of Hcy Using the Mutant SAH Enzyme

Plasma Hcy Assay Procedure 1

Step 1. Conversion of Hcy to SAH

To 50 μl of plasma sample in microcentrifuge tube or in uncoated 96-well plate was added 20 μl of 1% TBP and 50 μl of the wild type SAH hydrolase solution. After incubation at 25° C. for 15 min, 20 μl of the enzyme inhibitor solution was added to the reaction mixture, and incubated for 10 min. to inactivate SAH hydrolase.

Step 2. Removal of Remaining Ado and Enzyme Inhibitor

To the solution in Step 1 was added 30 μl of the multi-enzyme solution, and incubated for 15 min at room temperature.

Step 3. Trapping the Formed SAH Onto the Mutant SAH Hydrolase

150 μl solution in Step 2 was transferred to a microtiter well pre-coated with mutant SAH hydrolase. After 30 min. incubation at room temperature, the solution was emptied by inversion.

Step 4. Washing

The plate from Step 3 was washed three times with the washing solution followed by inversion and tapping.

Step 5. Binding of Fluorophore-Labeled Ado-Cys to the Mutant Enzyme

100 μl of the fluorophore-labeled Ado-Cys or fluorophore-labeled Ado-5' ester was added to the microtiter well in Step 4. After 20 min. incubation at room temperature, the plate was washed three times with the washing solution.

Step 6. Detection of the Mutant SAH Hydrolase-Bound Fluorophore-Labeled Ado-Cys

To the microtiter well from Step 5, 200 μl of 50 mM phosphate buffer, pH 7.2, was added, and the plate was read for fluorescence using a plate reader (Molecular Devices, fmax). The plasma Hcy concentration was calculated from the standard curve constructed under the same conditions.

Alternative Hcy Assay

Alternatively, the Hcy assay can also be performed by pre-coating SAH on microtiter well, and using fluorophore-labeled mutant SAH hydrolase for competition binding assay. The details are described as follows:

1. Pre-Coating SAH on Microtiter Well

SAH was conjugated to polylysine by activating the carboxylic group of SAH with $PCl_3$ at 50° C. The SAH-polylysine conjugate was purified by HPLC, and dissolved in 0.1 M carbonate buffer, pH 9.6. 300 μl of 100 μg/ml SAH-polylysine solution was added to each well, and incubated at 37° C. for 6 hours. The plate was then washed three times with washing solution containing 10 mM PBS, 0.1 M NaCl and 0.05% Tween 20. After inversion and tapping, the plate was stored at 4° C. before use.

2. Fluorophore-Labeled Mutant SAH Hydrolase

Mutant SAH hydrolase (e.g., F302S) was specifically fluorescence labels on Cys421, an non-essential cysteine residue which is located on the surface of the protein that is not involved in substrate binding and catalysis. Cys421 residue is readily accessible by thiol reactive molecules, and can be modified without effecting the binding affinity of the enzyme. Thiol specific reactive probes such as 7-diethylamino-3(4'-maleimidylphenyl)-4-methylcoumarin (CPM) can specifically label protein thiols. Mutant SAH hydrolase (F302S) (0.5 mg/ml) in 50 mM phosphate buffer, pH 7.2, was incubated with 2 mM of adenine to protect other thiols in the substrate binding site, followed by addition of CPM to final concentration of 50 μM. The reaction mixture was incubated at room temperature for 30 min. followed by gel filtration on a size exclusion column (Sephacryl S-300, 4.5 mm×60 cm) to remove adenine and excess CPM. The CPM-labeled F302S mutant SAH hydrolase (2 mg/ml) was kept in 50 mM phosphate buffer containing 20% glycerol at −20° C. The comparison of Km (SAH) and Kcat (SAH) for wild type and mutant F302S is shown below in Table 11.

TABLE 4

Comparison of kinetic constants between mutant and wild type SAH hydrolases

| Enzyme | Km (SAH) | Kcat (SAH) |
|---|---|---|
| wild type | 7.9 μM | 3.8 $S^{-1}$ |
| F302S | 1.0 μM | 0.1 $S^{-1}$ |

Plasma Hcy Assay Procedure 2

Step 1. Conversion of Hcy to SAH

To 50 μl of plasma sample in microcentrifuge tube or in uncoated 96-well plate was added 20 μl of 1% TBP and 50 μl of the wild type SAH hydrolase solution. After incubation at 25° C. for 15 min, 20 μl of the enzyme inhibitor solution was added to the reaction mixture, and incubated for 10 min. to inactivate SAH hydrolase.

Step 2. Removal of Remaining Ado and Enzyme Inhibitor

To the solution in Step 1 was added 30 μl of the multi-enzyme solution, and incubated for 15 min. at room temperature.

Step 3. Competition Binding of SAH to the Mutant SAH Hydrolase

One hundred μl of the solution from Step 2 was transferred to a microtiter well pre-coated with polylysine-SAH conjugate to which 150 μl of the fluorophore-labeled mutant SAH hydrolase was added. After incubation at room temperature for 30 min., the plate was inverted and tapped followed by three times of washing with the washing solution.

Step 4. Detection of the Fluorophore-Labeled Mutant SAH Hydrolase Bound to the Microtiter Well To the plate from Step 3 was added 200 μl of 10 nM PBS, and the plate was read by a plate reader (Molecular Devices, fmax) at Ex390 nm and Em460 nm. The plasma concentration of Hcy was calculated from the standard curve constructed under the same conditions with the standard samples.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The nucleotide sequence (SEQ ID NO:185) having GenBank accession number L32836 (Mus musculus) is:

```
   1 ccagcatgtc tgataaactg ccctacaaag tcgcggacat cggactggcc gcctggggac
  61 ggaaggctct ggatatagct gagaatgaga tgccaggatt gatgcgcatg cgggagatgt
 121 actcagcctc caagccactg aagggtgctc gcattgctgg ctgcctgcac atgaccgtgg
 181 agactgctgt tctcattgag actctcgtgg ccctgggtgc tgaggtgcgg tggtccagct
 241 gcaacatctt ctctactcag gaccatgcag cggctgccat tgccaaggct ggcattccag
 301 tgtttgcctg aagggcgag acagatgagg agtacctgtg gtgcattgag cagacgctgc
 361 acttcaagga cggacccctc aacatgattc tggatgatgg tggtgacctt actaacctca
 421 tccacaccaa atacccacag cttctgtcag gcatccgagg tatctctgag gagaccacga
 481 ctggggtcca aacctctac aagatgatgt ccaatgggat actgaacgtg cctgccatca
 541 atgtcaacga ttctgtcacc aagagcaagt ttgacaacct ctatggctgc cgggagtccc
 601 tcatagatgg catcaaacgg gccacagatg tgatgattgc gggcaaggtg gcggtggtgg
 661 caggctatgg tgatgtgggc aagggctgtg cccaggccct gaggggtttt ggggcccgag
 721 tcatcatcac cgagatcgac cccatcaatg cactgcaagc tgccatggag ggctatgagg
 781 taaccactat ggacgaagcc tgtaaggagg gcaacatctt tgtcaccacc acaggctgtg
 841 tggatatcat ccttggccgg cactttgagc agatgaagga tgacgccatt gtctgtaaca
 901 ttggacactt cgatgtggag attgatgtga agtggctcaa tgagaacgcg gtggagaaag
 961 tgaacatcaa gccccaggtg gaccgctact ggctaaagaa tgggcgccgc atcatcttgc
1021 tggctgaagg ccgtctggtc aacctgggtt gtgccatggg acaccccagc ttcgtgatga
1081 gcaactcctt cacaaaccag gtgatggcac agattgagct gtggaccac ccagataaat
1141 accctgttgg ggttcacttc ctgcctaaga agctggatga ggcggtggct gaagcccacc
1201 tgggcaagct gaatgtgaag ctgaccaagc tgactgagaa gcaagcccag tacctgggca
1261 tgcccatcaa cggccccttc aagcctgatc actaccgcta ctgagagctg ggctgtcct
1321 tcaccttcca gctgccatcc aagttccggg cccacctctc gtccccaaga gccaatgtca
1381 ccaactttgt ggttagtttg cctgtgttct gatccgtccc ccgccccca tcctcactgt
1441 ggctggtcac tccgtctttg gcctctgctg caccoctcat actgttccat atgtggcatc
1501 gagaacagag agaggtacct ggtaggcatc cacagggac atgatctcag aagtcttgga
1561 agtcctgagg ctggatgttg ctagtgatgg tcacaagcca tgcaccttat cattgatacc
1621 ctcacttggt ctttagatct gtgtgcctgg tttgcagatc cattggtttc tcagtccagg
1681 acccaagaac gagctccacc aaagagcagg aaccctggaa gtttgaaggc ccccgagagc
1741 tgggccttt tactgttggg cagtctctta aacctcatga tactgagttg gtactttttt
1801 tggtccctat ttcacaaggg ttcaggatag attaaccaag aaaggacaag tgacagactg
1861 aaagggctg gaaacaaga ggaaaggcct gtcactgtat agttgatggt tcctgtcaca
1921 agcccaggtc acaaacagat taatttgttt tataatgttt atatgctatt tagaatgtta
1981 acaaaggaag gtggataaaa tacagtttct actgcctaaa gaattttggc tctattaaaa
2041 tgtaagtgtg tggctgg
```

The nucleotide sequence (SEQ ID NO:186) having GenBank accession number M15185 (Rat) is:

```
   1 ctcactctag cggacttcgc cagcatggct gataaactgc cctacaaagt cgcggacatt
  61 ggactggctg cctggggacg gaaggccctg gacatagctg agaacgagat gccaggtttg
 121 atgcgcatgc gggagatgta ctcagcctcc aagccactga agggcgctcg cattgctggc
 181 tgcctgcaca tgactgtgga gactgctgtc ctcattgaga ctctcgtggc cctgggtgct
 241 gaggtgcggt ggtccagctg caacatcttc tccactcagg accatgcagc ggctgccatt
 301 gccaaggctg cattccagt gtttgcctgg aagggagaga cggatgaaga gtacctgtgg
 361 tgcattgagc agacgttgca cttcaaggac ggacccctca acatgattct ggatgatggc
 421 ggtgacctta ctaacctcat ccacaccaaa cacccacagc ttctgtcagg catccgaggt
 481 atctctgagg agaccacgac tggcgtccac aacctctaca agatgatggc caatgggata
 541 ctgaaggtgc ctgccatcaa cgtcaacgat tctgtcacca agagcaagtt tgacaacctc
 601 tatggctgcc gggagtccct catagatggc atcaaacggg caacagatgt gatgattgcg
 661 ggcaaggtgg cagtggtagc aggctatggt gatgtgggca agggttgtgc ccaggccctg
 721 cggggtttcg ggcccgagt catcatcacc gagattgacc ccatcaatgc actgcaagct
 781 gccatggagg gctacgaggt aaccaccatg gacgaggcct gtaaggaggg caacatcttt
 841 gtgaccacca cgggctgtgt tgatatcatc cttggtcggc actttgaaca gatgaaggat
 901 gatgccattg tctgtaacat tggacacttc gacgtggaga ttgatgtgaa gtggctcaat
 961 gagaacgctg tggagaaggt gaacatcaag ccccaggtgg accgctactt gctaaagaat
1021 gggcaccgca tcatcttgct ggctgagggc cgtctggtca acctgggttg tgccatgggc
1081 caccccagct tcgtgatgag caactccttc acaaaccagg tgatggcaca gattgagctg
1141 tggacccacc cagacaaata ccccgtgggg gttcacttcc tgcctaagaa gctggatgag
1201 gcagtggctg aagcccacct gggcaagctg aacgtcaagc tgaccaagct gactgagaag
1261 caggctcagt acctgggcat gcccattaac ggcccttca agcctgatca ctaccgctac
1321 tgagagctgg gactgccctt caccttccag ctgccatcct tgttccaggc cctacctctc
1381 gttcccaaga gcaaatgtca ccaactttgc agttacttct ccggtgttct gctccctccc
1441 ccggccctca tccacactgt gactggtctt tctgtctttg gcttctgctg tacccctcat
1501 actgttccct atgtggcata gagaacagag aggtacctgg gaggcatcca cagggatct
1561 gagctcttgg aaggtctgag gctggatgtt gctggtggtc acaagcccat gcaccttact
1621 atccaaactc tcgcttggtc tttagatccg tgtgcttggt ttacagacca atggtttctc
1681 ggcccaggac ccaagaagga gctctaccat ggggaagga accactggag tttgaaggct
1741 cctgagagct tggcctttt actgttgggc tgtctcttaa acctcctaat actgagttgg
1801 ctactttgg tccctatttc acaagggtta ggacagatta accaagaaag gacaagtgac
1861 agagactgaa aggggctgga aaacaaata gggaaaggcc tgtcacctac ggtataattg
1921 atggttccta tcacaagcct ggatcacaaa cagattaatt tgttctatgt ttatatactg
1981 tttagaatgt taacacagga aggtggataa aatacagttt ctagtgcct
```

The nucleotide sequence (SEQ ID NO:187) having GenBank accession number M61831 (human) is:

```
   1 ctgaggccca gcccccttcg cccgtttcca tcacgagtgc cgccagcatg tctgacaaac
  61 tgccctacaa agtcgccgac atcggcctgg ctgcctgggg acgcaaggcc ctggacattg
 121 ctgagaacga gatgccgggc ctgatgcgta tgcgggagcg gtactcggcc tccaagccac
 181 tgaagggcgc ccgcatcgct ggctgcctgc acatgaccgt ggagacggcc gtcctcattg
 241 agaccctcgt caccctgggt gctgaggtgc agtggtccag ctgcaacatc ttctccaccc
 301 agaaccatgc ggcggctgcc attgccaagg ctggcattcc ggtgtatgcc tggaagggcg
 361 aaacggacga ggagtacctg tggtgcattg agcagaccct gtacttcaag gacgggcccc
 421 tcaacatgat tctggacgac gggggcgacc tcaccaacct catccacacc aagtacccgc
 481 agcttctgcc aggcatccga ggcatctctg aggagaccac gactgggtc cacaacctct
 541 acaagatgat ggccaatggg atcctcaagg tgcctgccat caatgtcaat gactccgtca
 601 ccaagagcaa gtttgacaac ctctatggct gccgggagtc cctcatagat ggcatcaagc
 661 gggccacaga tgtgatgatt gccggcaagg tagcggtggt agcaggctat ggtgatgtgg
 721 gcaagggctg tgcccaggcc ctgcgggggtt tcggagcccg cgtcatcatc accgagattg
 781 accccatcaa cgcactgcag gctgccatgg agggctatga ggtgaccacc atggatgagg
 841 cctgtcagga gggcaacatc tttgtcacca ccacaggctg tattgacatc atccttggcc
 901 ggtaggtgcc agatgggggg tcccggggag tgagggagga gggcagagtt gggacagctt
 961 tctgtccctg acaatctccc acggtcttgg gctgcctgac aggcactttg agcagatgaa
1021 ggatgatgcc attgtgtgta acattggaca ctttgacgtg gagatcgatg tcaagtggct
1081 caacgagaac gccgtggaga aggtgaacat caagccgcag gtggaccggt atcggttgaa
1141 gaatgggcgc cgcatcatcc tgctggccga gggtcggctg gtcaacctgg ttgtgccat
1201 gggccacccc agcttcgtga tgagtaactc cttcaccaac caggtgatgg cgcagatcga
1261 gctgtggacc catccagaca gtaccccgt tggggttcat ttcctgccca agaagctgga
1321 tgaggcagtg gctgaagccc acctgggcaa gctgaatgtg aagttgacca agctaactga
1381 gaagcaagcc cagtacctgg gcatgtcctg tgatggcccc ttcaagccgg atcactaccg
1441 ctactgagag ccaggtctgc gtttcaccct ccagctgctg tccttgccca ggccccacct
1501 ctcctcccta agagctaatg gcaccaactt tgtgattggt ttgtcagtgt ccccatcga
1561 ctctctgggg ctgatcactt agttttggc ctctgctgca gccgtcatac tgttccaaat
1621 gtggcagcgg gaacagagta ccctcttcaa gccccggtca tgatggaggt cccagccaca
1681 gggaaccatg agctcagtgg tcttggaaca gctcactaag tcagtccttc cttagcctgg
1741 aagtcagtag tggagtcaca aagcccatgt gttttgccat ctaggccttc acctggtctg
1801 tggacttata cctgtgtgct tggtttacag gtccagtggt tcttcagccc atgacagatg
1861 agaagggct atattgaagg gcaaagagga actgttgttt gaattttcct gagagcctgg
1921 cttagtgctg ggccttctct taaacctcat tacaatgagg ttagtacttt tagtccctgt
1981 tttacagggg ttagaataga ctgttaaggg gcaactgaga aagaacagag aagtgacagc
2041 tagggggttga gaggggccag aaaaacatga atgcaggcag atttcgtgaa atctgccacc
2101 actttataac cagatggttc ctttcacaac cctgggtcaa aagagaata atttggccta
2161 taatgttaaa agaaagcagg aagtgggta aataaaaatc ttggtgcctg g
```

The nucleotide sequence (SEQ ID NO:188) having GenBank accession number M61832 (human) is:

```
   1 ggcccagccc ccttcgcccg tttccatcac gagtgccgcc agcatgtctg acaaactgcc
  61 ctacaaagtc gccgacatcg gcctggctgc ctggggacgc aaggccctgg acattgctga
 121 gaacgagatg ccgggcctga tgcgtatgcg ggagcggtac tcggcctcca agccactgaa
 181 gggcgcccgc atcgctggct gcctgcacat gaccgtggag acggccgtcc tcattgagac
 241 cctcgtcacc ctgggtgctg aggtgcagtg gtccagctgc aacatcttct ccacccagga
 301 ccatgcggcg gctgccattg ccaaggctgg cattccggtg tatgcctgga agggcgaaac
 361 ggacgaggag tacctgtggt gcattgagca gaccctgtac ttcaaggacg gcccctcaa
 421 catgattctg gacgacgggg gcgacctcac caacctcatc cacaccaagt acccgcagct
 481 tctgccaggc atccgaggca tctctgagga gaccacgact ggggtccaca acctctacaa
 541 gatgatggcc aatgggatcc tcaaggtgcc tgccatcaat gtcaatgact ccgtcaccaa
 601 gagcaagttt gacaacctct atggctgccg ggagtccctc atagatggca tcaagcgggc
 661 cacagatgtg atgattgccg gcaaggtagc ggtggtagca ggctatggtg atgtgggcaa
 721 gggctgtgcc caggccctgc ggggtttcgg agcccgcgtc atcatcaccg agattgaccc
 781 catcaacgca ctgcaggctg ccatggaggg ctatgaggtg accaccatgg atgaggcctg
 841 tcaggagggc aacatctttg tcaccaccac aggctgtatt gacatcatcc ttggccggca
 901 ctttgagcag atgaaggatg atgccattgt gtgtaacatt ggacactttg acgtggagat
 961 cgatgtcaag tggctcaacg agaacgccgt ggagaaggtg aacatcaagc cgcaggtgga
1021 ccggtatcgg ttgaagaatg gcgccgcat catcctgctg gccgagggtc ggctggtcaa
1081 cctgggttgt gccatgggcc accccagctt cgtgatgagt aactccttca ccaaccaggt
1141 gatggcgcag atcgagctgt ggacccatcc agacaagtac cccgttgggg ttcatttcct
1201 gcccaagaag ctggatgagg cagtggctga agcccacctg ggcaagctga atgtgaagtt
1261 gaccaagcta actgagaagc aagcccagta cctgggcatg tcctgtgatg gccccttcaa
1321 gccggatcac taccgctact gagagccagg tctgcgtttc accctccagc tgctgtcctt
1381 gcccaggccc cacctctcct ccctaagagc taatggcacc aactttgtga ctggtttgtc
1441 agtgtccccc atcgactctc tggggctgat cacttagttt ttggcctctg ctgcagccgt
1501 catactgttc caaatgtggc agcgggaaca gagtaccctc ttcaagcccc ggtcatgatg
1561 gaggtcccag ccacagggaa ccatgagctc agtggtcttg aacagctcca ctaagtcagt
1621 ccttccttag cctggaagcc agtagtggag tcacaaagcc catgtgtttt gccatctagg
1681 ccttcacctg gtctgtggac ttatacctgt gtgcttggtt tacaggtcca gtggttcttc
1741 agcccatgac agatgagaag gggctatatt gaagggcaaa gaggaactgt tgtttgaatt
1801 ttcctgagag cctggcttag tgctgggcct tctcttaaac ctcattacaa tgaggttagt
1861 acttttagtc cctgttttac aggggttaga atagactgtt aagggcaac tgagaaagaa
1921 cagagaagtg acagctaggg gttgagaggg gccagaaaaa catgaatgca ggcagatttc
1981 gtgaaatctg ccaccacttt ataaccagat ggttcctttc acaaccctgg gtcaaaagaa
2041 gaataatttg gcctataatg ttaaaagaaa gcaggaaggt gggt
```

What is claimed is:

1. A method for assaying homocysteine (Hcy), S-adenosylhomocysteine (SAH) or adenosine in a sample, which method comprises:

a) contacting a sample containing or suspected of containing Hcy, SAH or adenosine with a mutant SAH hydrolase derived from a SAH hydrolase, wherein said SAH hydrolase is encoded by a nucleic acid comprising a nucleotide sequence selected from the group consisting of SEQ ID NO:185, SEQ ID NO:186, SEQ ID NO:187, and SEQ ID NO:188;

wherein said mutant SAH hydrolase has binding affinity for Hcy, SAH or adenosine but has attenuated catalytic activity, and wherein said binding affinity and/or said attenuated catalytic activity of said mutant SAH hydrolase is caused by a mutation in said mutant SAH hydrolase's catalytic site, its binding site for NAD$^+$, NADH, Hcy, SAH, adenosine, or a combination thereof; and wherein the mutant SAH hydrolase: i) has a mutation in an amino acid residue that participates in catalysis or that is directly interacting with NAD$^+$, NADH, Hcy, SAH or adenosine, or ii) has a mutation in an amino acid residue that is adjacent to an amino acid residue that participates in catalysis or that is directly interacting with NAD$^+$, NADH, Hcy, SAH or adenosine, wherein the mutation in said mutant SAH hydrolase corresponding one or more amino acid positions selected from the group consisting of 53, 54, 57, 59, 80, 83, 121, 131, 134, 155, 157, 158, 159, 181, 190, 191, 214, 221, 226, 235, 240, 248, 263, 269, 285, 292, 301, 309, 322, 347, 351, 353, 361, 362, 379, 386, 388, 398, 401, 407, 409, 424, 425, 426, 427, 428, 429, 430, 431, and 432 SEQ ID NO:1 in said and b) detecting binding between Hcy, SAH or adenosine with said mutant SAH hydrolase, whereby the presence or amount of Hcy, SAH or adenosine in said sample is assessed.

2. The method of claim 1, wherein the mutant SAH hydrolase has at least 50 fold higher binding affinity for Hcy, SAH or adenosine than a wild type SAH hydrolase from which said mutant SAH hydrolase is derived.

3. A method for assaying homocysteine (Hcy), S-adenosylhomocysteine (SAH) or adenosine in a sample, which method comprises:

a) contacting a sample containing or suspected of containing Hcy, SAH or adenosine with a mutant SAH hydrolase, wherein the mutant SAH hydrolase is derived from a human SAH hydrolase comprising the amino acid sequence set forth in SEQ ID NO:1, wherein said mutant SAH hydrolase has binding affinity for Hcy, SAH or adenosine but has attenuated catalytic activity, and wherein said binding affinity and/or said attenuated catalytic activity of said mutant SAH hydrolase is caused by a mutation in said mutant SAH hydrolase's catalytic site, its binding site for NAD$^+$, NADH, Hcy, SAH, adenosine, or a combination thereof; and wherein the mutant SAH hydrolase: i) has a mutation in an amino acid residue that participates in catalysis or that is directly interacting with NAD$^+$, NADH, Hcy, SAH or adenosine; or ii) has a mutation in an amino acid residue that is adjacent to an amino acid residue that participates in catalysis or that is directly interacting with NAD$^+$, NADH, Hcy, SAH or adenosine, wherein the mutation in said mutant SAH hydrolase is at one or more amino acid positions selected from the group consisting of 38, 53, 54, 57, 59, 80, 83, 100, 121, 131, 134, 155, 157, 158, 159, 181, 190, 191, 214, 221, 226, 235, 240, 248, 263, 269, 285, 292, 301, 309, 322, 329, 347, 351, 353, 361, 362, 379, 386, 388, 398, 401, 407, 409, 420, 424, 425, 426, 427, 428, 429, 430, 431, and 432 in SEQ ID NO:1; and b) detecting binding between Hcy, SAH or adenosine with said mutant SAH hydrolase, whereby the presence or amount of Hcy, SAH or adenosine in said sample is assessed.

4. The method of claim 3, wherein the mutant SAH hydrolase comprises the amino acid sequence set forth in SEQ ID NO:1 and comprises a mutation selected from the group consisting of R38E, C53S, L54G, T57G, T57S, E59D, N80G, S83G, Y100T, K121A, D131E, D134E, E155G, T157G, T158Y, T159Y, N181A, N191A, L214A, Y221S, K226A, F235S, I240L, N248A, D263G, G269D, R285D, D292G, H301T, K309R, K322G, R329A, L347F, L347Y, L347I, M351A, H353R, S361G, F362S, Y379S, L386A, K388A, H398A, K401R, K401D, T407S, L409G, S420T, P424A, F425S, P427A, D428G, H429A, Y430T, R431K, R431G, Y432S, Y432A, Y432F, and a combination thereof.

5. The method of claim 1, wherein prior to the contact between the sample and the mutant SAH hydrolase, oxidized or conjugated Hcy in the sample is converted into reduced Hcy by a reducing agent.

6. The method of claim 1, wherein prior to the contact between the sample and the mutant SAH hydrolase, the Hcy in the sample is converted into SAH.

7. The method of claim 5, further comprising a step of removing the reducing agent used to convert oxidized or conjugated Hcy into reduced Hcy prior to or concurrently with contacting the sample with the mutant SAH hydrolase, wherein the reducing agent is removed by chromatography.

8. The method of claim 1, wherein the sample is contacted with the mutant SAH hydrolase in the presence of a labeled SAH, thereby the amount of the labeled SAH, bound to the mutant SAH hydrolase inversely relates to the amount of SAH in the sample.

9. The method of claim 8, wherein the labeled SAH, is labeled with a fluorophore, an enzyme, or a protein.

10. The method of claim 1, wherein the mutant SAH hydrolase is a labeled mutant SAH hydrolase.

11. The method of claim 10, wherein the labeled mutant SAH is a fluorescently, enzymatically, biotin or streptavidin labeled mutant SAH hydrolase.

12. The method of claim 9, wherein the fluorophore labeled SAH, is directly contacted by the mutant SAH hydrolase, and the resulting change of fluorescent polarization is measured for assessing the presence or amount of Hcy, SAH or adenosine in the sample.

13. The method of claim 9, wherein the enzyme labeled SAH, is directly contacted by the mutant SAH hydrolase, and the resulting change of enzyme activity is measured for assessing the presence or amount of Hcy, SAH or adenosine in the sample.

14. The method of claim 1, wherein the mutant SAH hydrolase is immobilized.

15. The method of claim 1, wherein the sample is a body fluid or a biological tissue.

16. The method of claim 3, wherein the mutant SAH hydrolase has at least 50 fold higher binding affinity for Hcy, SAH or adenosine than a wild type SAH hydrolase from which said mutant SAH hydrolase is derived.

17. The method of claim 6, wherein the sample is contacted with the mutant SAH hydrolase in the presence of a labeled SAH, thereby the amount of the labeled SAH, bound to the mutant SAH hydrolase inversely relates to the amount of SAH in the sample.

18. The method of claim 17, wherein the labeled SAH, is labeled with a fluorophore, an enzyme, or a protein.

19. The method of claim 3, wherein the mutant SAH hydrolase is a labeled mutant SAH hydrolase.

20. The method of claim 3, wherein the mutant SAH hydrolase is immobilized.

* * * * *

SEQUENCE LISTING

<160> NUMBER OF SEQ ID NOS: 188

<210> SEQ ID NO 1
<211> LENGTH: 432
<212> TYPE: PRT
<213> ORGANISM: Homo sapiens

<400> SEQUENCE: 1

Met Ser Asp Lys Leu Pro Tyr Lys Val Ala Asp Ile Gly Leu Ala Ala
1               5                   10                  15

Trp Gly Arg Lys Ala Leu Asp Ile Ala Glu Asn Glu Met Pro Gly Leu
            20                  25                  30

Met Arg Met Arg Glu Arg Tyr Ser Ala Ser Lys Pro Leu Lys Gly Ala
        35                  40                  45

Arg Ile Ala Gly Cys Leu His Met Thr Val Glu Thr Ala Val Leu Ile
    50                  55                  60

Glu Thr Leu Val Thr Leu Gly Ala Glu Val Gln Trp Ser Ser Cys Asn
65                  70                  75                  80

Ile Phe Ser Thr Gln Asn His Ala Ala Ala Ile Ala Lys Ala Gly
                85                  90                  95

Ile Pro Val Tyr Ala Trp Lys Gly Glu Thr Asp Glu Glu Tyr Leu Trp
            100                 105                 110

Cys Ile Glu Gln Thr Leu Tyr Phe Lys Asp Gly Pro Leu Asn Met Ile
        115                 120                 125

Leu Asp Asp Gly Gly Asp Leu Thr Asn Leu Ile His Thr Lys Tyr Pro
    130                 135                 140

Gln Leu Leu Pro Gly Ile Arg Gly Ile Ser Glu Glu Thr Thr Thr Gly
145                 150                 155                 160

Val His Asn Leu Tyr Lys Met Met Ala Asn Gly Ile Leu Lys Val Pro
                165                 170                 175

Ala Ile Asn Val Asn Asp Ser Val Thr Lys Ser Lys Phe Asp Asn Leu
            180                 185                 190

Tyr Gly Cys Arg Glu Ser Leu Ile Asp Gly Ile Lys Arg Ala Thr Asp
        195                 200                 205

Val Met Ile Ala Gly Lys Val Ala Val Ala Gly Tyr Gly Asp Val
    210                 215                 220

Gly Lys Gly Cys Ala Gln Ala Leu Arg Gly Phe Gly Ala Arg Val Ile
225                 230                 235                 240

Ile Thr Glu Ile Asp Pro Ile Asn Ala Leu Gln Ala Ala Met Glu Gly
                245                 250                 255

Tyr Glu Val Thr Thr Met Asp Glu Ala Cys Gln Glu Gly Asn Ile Phe
            260                 265                 270

Val Thr Thr Thr Gly Cys Ile Asp Ile Ile Leu Gly Arg His Phe Glu
        275                 280                 285

Gln Met Lys Asp Asp Ala Ile Val Cys Asn Ile Gly His Phe Asp Val
    290                 295                 300

Glu Ile Asp Val Lys Trp Leu Asn Glu Asn Ala Val Glu Lys Val Asn
305                 310                 315                 320

Ile Lys Pro Gln Val Asp Arg Tyr Arg Leu Lys Asn Gly Arg Arg Ile
                325                 330                 335

Ile Leu Leu Ala Glu Gly Arg Leu Val Asn Leu Gly Cys Ala Met Gly
            340                 345                 350

His Pro Ser Phe Val Met Ser Asn Ser Phe Thr Asn Gln Val Met Ala

|     | 355 |     |     |     | 360 |     |     |     |     | 365 |     |
| --- | --- | --- | --- | --- | --- | --- | --- | --- | --- | --- | --- |

Gln Ile Glu Leu Trp Thr His Pro Asp Lys Tyr Pro Val Gly Val His
            370                 375                 380

Phe Leu Pro Lys Lys Leu Asp Glu Ala Val Ala Glu Ala His Leu Gly
385                 390                 395                 400

Lys Leu Asn Val Lys Leu Thr Lys Leu Thr Glu Lys Gln Ala Gln Tyr
                405                 410                 415

Leu Gly Met Ser Cys Asp Gly Pro Phe Lys Pro Asp His Tyr Arg Tyr
            420                 425                 430

<210> SEQ ID NO 2
<211> LENGTH: 2211
<212> TYPE: DNA
<213> ORGANISM: Homo sapiens

<400> SEQUENCE: 2

| | |
|---|---|
| ctgaggccca gcccccttcg cccgtttcca tcacgagtgc cgccagcatg tctgacaaac | 60 |
| tgccctacaa agtcgccgac atcggcctgg ctgcctgggg acgcaaggcc ctggacattg | 120 |
| ctgagaacga gatgccgggc ctgatgcgta tgcgggagcg gtactcggcc tccaagccac | 180 |
| tgaagggcgc ccgcatcgct ggctgcctgc acatgaccgt ggagacggcc gtcctcattg | 240 |
| agaccctcgt caccctgggt gctgaggtgc agtggtccag ctgcaacatc ttctccaccc | 300 |
| agaaccatgc ggcggctgcc attgccaagg ctggcattcc ggtgtatgcc tggaagggcg | 360 |
| aaacggacga ggagtacctg tggtgcattg agcagaccct gtacttcaag gacgggcccc | 420 |
| tcaacatgat tctggacgac gggggcgacc tcaccaacct catccacacc aagtacccgc | 480 |
| agcttctgcc aggcatccga ggcatctctg aggagaccac gactgggggtc acaaccctct | 540 |
| acaagatgat ggccaatggg atcctcaagg tgcctgccat caatgtcaat gactccgtca | 600 |
| ccaagagcaa gtttgacaac ctctatggct gccgggagtc cctcatagat ggcatcaagc | 660 |
| gggccacaga tgtgatgatt gccggcaagg tagcgtggt agcaggctat ggtgatgtgg | 720 |
| gcaagggctg tgcccaggcc tgcgggggtt tcggagcccg cgtcatcatc accgagattg | 780 |
| acccccatca cgcactgcag ctgccatgg agggctatga ggtgaccacc atggatgagg | 840 |
| cctgtcagga gggcaacatc tttgtcacca ccacaggctg tattgacatc atccttggcc | 900 |
| ggtaggtgcc agatgggggg tcccggggag tgagggagga gggcagagtt gggacagctt | 960 |
| tctgtccctg acaatctccc acggtcttgg gctgcctgac aggcactttg agcagatgaa | 1020 |
| ggatgatgcc attgtgtgta acattggaca ctttgacgtg gagatcgatg tcaagtggct | 1080 |
| caacgagaac gccgtggaga aggtgaacat caagccgcag gtggaccggt atcggttgaa | 1140 |
| gaatgggcgc cgcatcatcc tgctggccga gggtcggctg tcaacctgg ttgtgccat | 1200 |
| gggccacccc agcttcgtga tgagtaactc cttcaccaac caggtgatgg cgcagatcga | 1260 |
| gctgtgacc catccagaca agtacccgt tggggttcat ttcctgccca agaagctgga | 1320 |
| tgaggcagtg gctgaagccc acctgggcaa gctgaatgtg aagttgacca agctaactga | 1380 |
| gaagcaagcc cagtacctgg gcatgtcctg tgatggcccc ttcaagccgg atcactaccg | 1440 |
| ctactgagag ccaggtctgc gtttcaccct ccagctgctg tccttgccca ggccccacct | 1500 |
| ctcctcccta agagctaatg caccaacttt gtgattggt tgtcagtgt ccccatcga | 1560 |
| ctctctgggg ctgatcactt agttttggc ctctgctgca gccgtcatac tgttccaaat | 1620 |
| gtggcagcgg aaacagagta ccctcttcaa gccccggtca tgatggaggt cccagccaca | 1680 |
| gggaaccatg agctcagtgg tcttggaaca gctcactaag tcagtccttc cttagcctgg | 1740 |

```
aagtcagtag tggagtcaca aagcccatgt gttttgccat ctaggccttc acctggtctg    1800
tggacttata cctgtgtgct tggtttacag gtccagtggt tcttcagccc atgacagatg    1860
agaaggggct atattgaagg gcaaagagga actgttgttt gaattttcct gagagcctgg    1920
cttagtgctg ggccttctct taaacctcat acaatgagg ttagtacttt tagtccctgt     1980
tttacagggg ttagaataga ctgttaaggg caactgaga aagaacagag aagtgacagc     2040
taggggttga gaggggccag aaaaacatga atgcaggcag atttcgtgaa atctgccacc   2100
actttataac cagatggttc ctttcacaac cctgggtcaa aaagagaata atttggccta    2160
taatgttaaa agaaagcagg aaggtgggta aataaaaatc ttggtgcctg g              2211

<210> SEQ ID NO 3
<211> LENGTH: 2226
<212> TYPE: DNA
<213> ORGANISM: Homo sapiens
<220> FEATURE:
<221> NAME/KEY: misc_feature
<222> LOCATION: (1)...(2226)
<223> OTHER INFORMATION: n = A,T,C or G

<400> SEQUENCE: 3
gttgccagct tgcatctgcc atcatttgat gcccaccta cagagctgac agatgaccaa      60 gcaaatatc tgggactcaa caaaaatggg ccattcaaac ctaattatta cagatactaa    120
tggaccatac taccaaggac cagtccacct gaaccacaca ctctaaagaa atatttttta    180
agataacttt tattttcttc ttactccttt cctcttgatt ttttttcctat aatttcattc   240 ttgtttttc atctcattat ccaagttctg cagaccacac aggaacttgc ttcatggctc    300
tttagatgaa atagaagttc agggttcctc actctagtca ctaaagaagg attttactct  360
cccagcccag aaaggtgatt ctttctttac catttctggg gactttagtc ttaattaggt   420
accttattaa caggaaatgc taaggtacct tctctgtgga acaatctgca atgtctaaat   480
cgccttaaaa gagcccattt cttagctgct gaaatcagtg ctctttcact tcttcagaga   540
agcagggatg gtacctaccc ggcagtggg ttagatgtgg gtggtgcatg ttaatttccc    600
ttagaagttc caagccctgt ttcctgcgta aggtggtat gtccagttca gagatgtgta    660
taatgagcat ggcttgttaa gatcaggagg cccacttgga tttatagtat agcccttcct   720
ccactcccac cagacttgct cattttttcga gttttttaact agactacact ctattgagtt 780
taattttgtc ctctaggatt tatttctgtt gtccaaaaaa aaanaaaaag aaaagaaaaa  840
ttaaggagaa tttttggtgt taatgctgag gaattgcttg agtggttagt tgttaccaat   900
ttctcttttg aacctttgga gctaaggatg ctgagtctag agaaatgcta gtctcaagcc   960
ctgttaagtc cctctgtttc tagcccgtag ttcatagcat cagtgaactg gagccacaac  1020
agcaaattct atcagctgtg taccatacag cttgtgctga aggcgaattt cttgagccat  1080
tactcagtat aaagcactga gttctatctt taggatttat ctttaagagc aaatttctgg  1140
tcagctgtgc ttctgcaacc taaaatattt aaagggaggt aggtgtgggc aggaggagga  1200
atgataaatt gggccagggc aagaaaaatc tagcttcata taatttgtct gggactatac   1260
accctatata atgttagttt tacagaagta atatgacttt tgattgctac ataccacaaa  1320
gagtttatga actgagatca taaagggcaa ctgatgtgtg aagaaagtag tcagtacatc  1380
ctggctcatg ctctgaaaga atatccagag aggctctctc aaagatcagg gagatgtatt  1440
cccatgccat gcaccctgct tcccagcatt tctgcatggt caagtgagct ttatgctcat   1500
```

-continued

| gagctttaag tatataatta tccaggatttt taaatcctca acttgttcta gcttgtgatc | 1560 |
| cctcaaagtt gggtcatacg ttagtgctag atactagaaa ttttcactttt tccactgatc | 1620 |
| agagagacag acattaaaaa caaaaataga agaaaggaaa gctttcaccc tgcagcttct | 1680 |
| tagcagggaa caattgtctt gccaaaactt ttttcccttt tctctcccat tttcttttac | 1740 |
| ccaatcccttt cttactcctt gccagtgtga ccatgctttc ttctctgtag atgttaacag | 1800 |
| ttaaggccta ttttcctcgg gcacttaacc aaccaatcag aacaccacat ctgttagggg | 1860 |
| aggtaacctg gccaacagtg tatccatcac gttagccctg ctggagggaa gggacccaca | 1920 |
| ttcacctgcc ctctgacctg ccccttgatc ccatatctat taccgtgtcc ataggaataa | 1980 |
| taggtaaggg ctctgtctct gtcaagccat gtaacaaagg acactgttaa aaaaaaaaa | 2040 |
| aagtctggca tcagagggag catgtggaga gcaacttggg aagaacaagt tcattttgta | 2100 |
| ttgaatgatt tttaatgaat gcaatattaa tccttgcaga tgagcaataa tcattaaaat | 2160 |
| cgattaaaat grtaagrcct taaaaaaaaa aaanaaggnn gagaaggang gnnggggtg | 2220 |
| nngngg | 2226 |

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
ggccccttcg agccggatca ctaccgc                                        27

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 5
gacttcgtca ccgccagcaa gtttggg                                        27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 6
cccaaacttg ctggcggtga cgaagtc                                        27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 7
aacattggac actctgacgt ggagatc                                        27

<210> SEQ ID NO 8

```
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 8
gatctccacg tcagagtgtc caatgtt                                           27

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 9
tgtaacattg gagactttga cgtggag                                           27

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 10
ctccacgtca aagtctccaa tgttaca                                           27

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 11
tgtgccatgg gctcccccag cttcgtg                                           27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 12
cacgaagctg ggggagccca tggcaca                                           27

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 13
ctggccgagg gtgcgctggt caacctg                                           27

<210> SEQ ID NO 14
<211> LENGTH: 27
```

```
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 14
caggttgacc agcgcaccct cggccag                                              27

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 15
aagagcaagt ttgccaacct ctatggc                                              27

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 16
gccatagagg ttggcaaact tgctctt                                              27

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 17
agctgcaaca tcgcctccac ccaggac                                              27

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 18
gtcctgggtg gaggcgatgt tgcagct                                              27

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 19
gccatcaatg tcgacgactc cgtcacc                                              27

<210> SEQ ID NO 20
<211> LENGTH: 27
<212> TYPE: DNA
```

```
<213> ORGANISM: Artificial Sequence
<220> FEATURE:
<223> OTHER INFORMATION: Oligonucleotide used for site-directed
      mutagenesis of human SAH hydrolases

<400> SEQUENCE: 20
ggtgacggag tcgtcgacat tgatggc                                          27

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 21
ccggatcact acgcctactg agaattc                                          27

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 22
gaattctcag taggcgtagt gatccgg                                          27

<210> SEQ ID NO 23
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 23
gatggcccct tccgcccgga tcactac                                          27

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 24
gtagtgatcc gggcggaagc catcaca                                          27

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 25
aacctctatg gctcccggga gtccctc                                          27

<210> SEQ ID NO 26
<211> LENGTH: 27
<212> TYPE: DNA
<213> ORGANISM: Artificial Sequence
```

-continued

<220> FEATURE:
<223> OTHER INFORMATION: Oligonucleotide used for site-directed
      mutagenesis of human SAH hydrolases

<400> SEQUENCE: 26
gagggactcc cgggagccat agaggtt                                            27

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 27
gatcactacc gctgatgaga attcgag                                            27

<210> SEQ ID NO 28
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 28
ctcgaattct catcagcggt agtgatc                                            27

<210> SEQ ID NO 29
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 29
ggcatctctg aggcgaccac gactggg                                            27

<210> SEQ ID NO 30
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 30
cccagtcgtg gtcgcctcag agatgcc                                            27

<210> SEQ ID NO 31
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 31
ggcatctctg aggacaccac gactggg                                            27

<210> SEQ ID NO 32
<211> LENGTH: 27
<212> TYPE: DNA
<213> ORGANISM: Artificial Sequence
<220> FEATURE:

<223> OTHER INFORMATION: Oligonucleotide used for site-directed
      mutagenesis of human SAH hydrolases

<400> SEQUENCE: 32
cccagtcgtg gtgtcctcag agatgcc                                         27

<210> SEQ ID NO 33
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 33
ctcaacatga ttctggacaa ggggggcgac ctcacc                               36

<210> SEQ ID NO 34
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 34
ggtgaggtcg ccccccttgt ccagaatcat gttgag                               36

<210> SEQ ID NO 35
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 35
ctcaacatga ttctggacaa cggggggcgac ctcacc                              36

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 36
ggtgaggtcg cccccgttgt ccagaatcat gttgag                               36

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 37
gactccgtca ccgcgagcaa gtttgac                                         27

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide used for site-directed mutagenesis of human SAH hydrolases

<400> SEQUENCE: 38
gtcaaacttg ctcgcggtga cggagtc                                27

<210> SEQ ID NO 39
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 39
gactccgtca ccgacagcaa gtttgac                                27

<210> SEQ ID NO 40
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 40
gtcaaacttg ctgtcggtga cggagtc                                27

<210> SEQ ID NO 41
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 41
gctggctgcc tgcccatgac cgtggagacg                             30

<210> SEQ ID NO 42
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 42
cgtctccacg gtcatgggca ggcagccagc                             30

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 43
ctgctggccg agggtgcgct ggtcaacctg                             30

<210> SEQ ID NO 44
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

```
<400> SEQUENCE: 44
caggttgacc agcgcaccct cggccagcag                                          30

<210> SEQ ID NO 45
<211> LENGTH: 39
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 45
gtgtgtaaca ttggacactt tgaggtggag atcgatgtc                                39

<210> SEQ ID NO 46
<211> LENGTH: 39
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 46
gacatcgatc tccacctcaa agtgtccaat gttacacac                                39

<210> SEQ ID NO 47
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 47
gtgtgtaaca ttggacacat tgacgtggag atc                                      33

<210> SEQ ID NO 48
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 48
gatctccacg tcaatgtgtc caatgttaca cac                                      33

<210> SEQ ID NO 49
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 49
gccgagggtc gggggggtcaa cctgggttgt gcc                                     33

<210> SEQ ID NO 50
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases
```

```
<400> SEQUENCE: 50
ggcacaaccc aggttgaccc cccgaccctc ggc                                    33

<210> SEQ ID NO 51
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 51
cagtggtcca gctgcaacat ctcctccacc caggac                                 36

<210> SEQ ID NO 52
<211> LENGTH: 36
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 52
gtcctgggtg gaggagatgt tgcagctgga ccactg                                 36

<210> SEQ ID NO 53
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 53
gaggagacca cgtccggggt ccacaacctc                                        30

<210> SEQ ID NO 54
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 54
gaggttgtgg accccggacg tggtctcctc                                        30

<210> SEQ ID NO 55
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 55
ggtcggctgg tcggcctggg ttgtgcc                                           27

<210> SEQ ID NO 56
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 56
```
ggcacaaccc aggccgacca gccgacc         27

<210> SEQ ID NO 57
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 57
ggtcggctgg tcgacctggg ttgtgcc         27

<210> SEQ ID NO 58
<211> LENGTH: 27
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 58
ggcacaaccc aggtcgacca gccgacc         27

<210> SEQ ID NO 59
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 59
gtgcagtggt ccagcgccaa catcttctcc acc         33

<210> SEQ ID NO 60
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 60
ggtggagaag atgttggcgc tggaccactg cac         33

<210> SEQ ID NO 61
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 61
gtgcagtggt ccagcggcaa catcttctcc acc         33

<210> SEQ ID NO 62
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 62

```
ggtggagaag atgttgccgc tggaccactg cac                                33
```

<210> SEQ ID NO 63
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 63

```
gtgtgtaaca ttggagcctt tgacgtggag                                    30
```

<210> SEQ ID NO 64
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 64

```
ctccacgtca aaggctccaa tgttacacac                                    30
```

<210> SEQ ID NO 65
<211> LENGTH: 39
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 65

```
gtgtgtaaca ttggacactt tgccgtggag atcgatgtc                          39
```

<210> SEQ ID NO 66
<211> LENGTH: 39
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 66

```
gacatcgatc tccacggcaa agtgtccaat gttacacac                          39
```

<210> SEQ ID NO 67
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 67

```
atctctgagg agacctatac tggggtccac aac                                33
```

<210> SEQ ID NO 68
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 68

```
gttgtggacc ccagtatagg tctcctcaga gat                                33
```

<210> SEQ ID NO 69
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 69
atctctgagg agaccacgta tggggtccac aac                          33

<210> SEQ ID NO 70
<211> LENGTH: 33
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 70
gttgtggacc ccatacgtgg tctcctcaga gat                          33

<210> SEQ ID NO 71
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 71
ggtcggctgg tcaactttgg ttgtgccatg                              30

<210> SEQ ID NO 72
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 72
catggcacaa ccaaagttga ccagccgacc                              30

<210> SEQ ID NO 73
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 73
atgcgtatgc gggaggaata ctcggcctcc                              30

<210> SEQ ID NO 74
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 74
ggaggccgag tattcctccc gcatacgcat                              30

```
<210> SEQ ID NO 75
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 75
gcccgcatcg ctggctctct gcacatgacc                                         30

<210> SEQ ID NO 76
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 76
ggtcatgtgc agagagccag cgatgcgggc                                         30

<210> SEQ ID NO 77
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 77
ggctgcctgc acatgggggt ggagacggcc                                         30

<210> SEQ ID NO 78
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 78
ggccgtctcc accccatgt gcaggcagcc                                          30

<210> SEQ ID NO 79
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 79
ctgcacatga ccgtggatac ggccgtcctc                                         30

<210> SEQ ID NO 80
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 80
gaggacggcc gtatccacgg tcatgtgcag                                         30
```

```
<210> SEQ ID NO 81
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 81
ggctgcctgc acatgtctgt ggagacggcc                                          30

<210> SEQ ID NO 82
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 82
ggccgtctcc acagacatgt gcaggcagcc                                          30

<210> SEQ ID NO 83
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 83
ggtcggctgg tcaactatgg ttgtgccatg                                          30

<210> SEQ ID NO 84
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 84
catggcacaa ccatagttga ccagccgacc                                          30

<210> SEQ ID NO 85
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 85
ggtcggctgg tcaacattgg ttgtgccatg                                          30

<210> SEQ ID NO 86
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 86
catggcacaa ccaatgttga ccagccgacc                                          30

<210> SEQ ID NO 87
```

<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 87
tgcaacatct tcggtaccca ggaccatgcg          30

<210> SEQ ID NO 88
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 88
tgcaacatct tcggtaccca ggaccatgcg          30

<210> SEQ ID NO 89
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 89
gcccgcatcg ctggctgcgg tcacatgacc          30

<210> SEQ ID NO 90
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 90
ggtcatgtga ccgcagccag cgatgcgggc          30

<210> SEQ ID NO 91
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 91
ggcattccgg tgactgcctg gaagggcgaa          30

<210> SEQ ID NO 92
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 92
ttcgcccttc caggcagtca ccggaatgcc          30

<210> SEQ ID NO 93
<211> LENGTH: 30

```
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 93
accctgtact cgctgacgg gcccctcaac                                    30

<210> SEQ ID NO 94
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 94
gttgaggggc ccgtcagcga agtacagggt                                   30

<210> SEQ ID NO 95
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 95
agcaagtttg acgctctcta tggctgccgg                                   30

<210> SEQ ID NO 96
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 96
ccggcagcca tagagagcgt caaacttgct                                   30

<210> SEQ ID NO 97
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 97
ctgggttgtg ccgctggcca ccccagcttc                                   30

<210> SEQ ID NO 98
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 98
gaagctgggg tggccagcgg cacaacccag                                   30

<210> SEQ ID NO 99
<211> LENGTH: 30
<212> TYPE: DNA
```

-continued

```
<213> ORGANISM: Artificial Sequence
<220> FEATURE:
<223> OTHER INFORMATION: Oligonucleotide used for site-directed
      mutagenesis of human SAH hydrolases

<400> SEQUENCE: 99
ctgggttgtg ccatgggccg tcccagcttc                              30

<210> SEQ ID NO 100
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 100
gaagctggga cggcccatgg cacaacccag                              30

<210> SEQ ID NO 101
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 101
ttcgtgatga gtaactccag taccaaccag                              30

<210> SEQ ID NO 102
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 102
ctggttggta ctggagttac tcatcacgaa                              30

<210> SEQ ID NO 103
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 103
atgattctgg acgaagggggg cgacctcacc                             30

<210> SEQ ID NO 104
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 104
ggtgaggtcg ccccttcgt ccagaatcat                               30

<210> SEQ ID NO 105
<211> LENGTH: 30
<212> TYPE: DNA
<213> ORGANISM: Artificial Sequence
```

```
<220> FEATURE:
<223> OTHER INFORMATION: Oligonucleotide used for site-directed
      mutagenesis of human SAH hydrolases

<400> SEQUENCE: 105
atctctgagg agggtacgac tggggtccac                                           30

<210> SEQ ID NO 106
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 106
gtggacccca gtcgtaccct cctcagagat                                           30

<210> SEQ ID NO 107
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 107
tggtccagct gcggtatctt ctccacccag                                           30

<210> SEQ ID NO 108
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 108
ctgggtggag aagataccgc agctggacca                                           30

<210> SEQ ID NO 109
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 109
atgattctgg acgacggggg cgaactcacc                                           30

<210> SEQ ID NO 110
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 110
ggtgagttcg ccccccgtcgt ccagaatcat                                          30

<210> SEQ ID NO 111
<211> LENGTH: 30
<212> TYPE: DNA
<213> ORGANISM: Artificial Sequence
<220> FEATURE:
```

<223> OTHER INFORMATION: Oligonucleotide used for site-directed
      mutagenesis of human SAH hydrolases

<400> SEQUENCE: 111
atctctggtg agaccacgac tggggtccac                                    30

<210> SEQ ID NO 112
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 112
gtggacccca gtcgtggtct caccagagat                                    30

<210> SEQ ID NO 113
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 113
gccatcaatg tcgctgactc cgtcaccaag                                    30

<210> SEQ ID NO 114
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 114
cttggtgacg gagtcagcga cattgatggc                                    30

<210> SEQ ID NO 115
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 115
atgattgccg gcgctgtagc ggtggtagca                                    30

<210> SEQ ID NO 116
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 116
tgctaccacc gctacagcgc cggcaatcat                                    30

<210> SEQ ID NO 117
<211> LENGTH: 30
<212> TYPE: DNA
<213> ORGANISM: Artificial Sequence
<220> FEATURE:
<223> OTHER INFORMATION: Oligonucleotide used for site-directed mutagenesis of human SAH hydrolases

<400> SEQUENCE: 117
gtggtagcag gctctggtga tgtgggcaag                                    30

<210> SEQ ID NO 118
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 118
cttgcccaca tcaccagagc ctgctaccac                                    30

<210> SEQ ID NO 119
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 119
ggtgatgtgg gcgctggctg tgcccaggcc                                    30

<210> SEQ ID NO 120
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 120
ggcctgggca cagccagcgc ccacatcacc                                    30

<210> SEQ ID NO 121
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 121
gccctgcggg gttctggagc ccgcgtcatc                                    30

<210> SEQ ID NO 122
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 122
gatgacgcgg gctccagaac cccgcagggc                                    30

<210> SEQ ID NO 123
<211> LENGTH: 29
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 123
ggagccgcgt ccttatcacc gagattgac                                    29

<210> SEQ ID NO 124
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 124
gtcaatctcg gtgataagga cgcgggctcc                                   30

<210> SEQ ID NO 125
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 125
attgacccca tcgctgcact gcaggctgcc                                   30

<210> SEQ ID NO 126
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 126
ggcagcctgc agtgcagcga tggggtcaat                                   30

<210> SEQ ID NO 127
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 127
gtgaccacca tgggtgaggc ctgtcaggag                                   30

<210> SEQ ID NO 128
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 128
ctcctgacag gcctcaccca tggtggtcac                                   30

<210> SEQ ID NO 129
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 129
gaggcctgtc aggaggataa catctttgtc                              30

<210> SEQ ID NO 130
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 130
gacaaagatg ttatcctcct gacaggcctc                              30

<210> SEQ ID NO 131
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 131
gacatcatcc ttggcgatca ctttgagcag                              30

<210> SEQ ID NO 132
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 132
ctgctcaaag tgatcgccaa ggatgatgtc                              30

<210> SEQ ID NO 133
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 133
cagatgaagg gtgatgccat tgtgtgtaac                              30

<210> SEQ ID NO 134
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 134
gttacacaca atggcatcac ccttcatctg                              30

<210> SEQ ID NO 135
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 135

```
aacattggaa cttttgacgt ggagatcgat                                    30
```

<210> SEQ ID NO 136
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 136

```
atcgatctcc acgtcaaaag ttccaatgtt                                    30
```

<210> SEQ ID NO 137
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 137

```
gagatcgatg tcagatggct caacgagaac                                    30
```

<210> SEQ ID NO 138
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 138

```
gttctcgttg agccatctga catcgatctc                                    30
```

<210> SEQ ID NO 139
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 139

```
gtgaacatcg gtccgcaggt ggaccggtat                                    30
```

<210> SEQ ID NO 140
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 140

```
ataccggtcc acctgcggac cgatgttcac                                    30
```

<210> SEQ ID NO 141
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 141

```
gaccggtatg ctttgaagaa tgggcgccgc                                              30
```

<210> SEQ ID NO 142
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 142

```
gcggcgccca ttcttcaaag cataccggtc                                              30
```

<210> SEQ ID NO 143
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 143

```
atgagtaacg gtttcaccaa ccaggtgatg                                              30
```

<210> SEQ ID NO 144
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 144

```
catcacctgg ttggtgaaac cgttactcat                                              30
```

<210> SEQ ID NO 145
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 145

```
catccagaca agtctcccgt tggggttcat                                              30
```

<210> SEQ ID NO 146
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 146

```
atgaacccca acgggagact tgtctggatg                                              30
```

<210> SEQ ID NO 147
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 147

```
ggggttcatt tcgctcccaa gaagctggat                                              30
```

<210> SEQ ID NO 148
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 148
atccagcttc ttgggagcga aatgaacccc                              30

<210> SEQ ID NO 149
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 149
catttcctgc ccggtaagct ggatgaggca                              30

<210> SEQ ID NO 150
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 150
tgcctcatcc agcttaccgg gcaggaaatg                              30

<210> SEQ ID NO 151
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 151
gcagtggctg aagccgctct gggcaagctg                              30

<210> SEQ ID NO 152
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 152
cagcttgccc agagcggctt cagccactgc                              30

<210> SEQ ID NO 153
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 153
cacctgggcc gtctgaatgt gaagttgacc                              30

<210> SEQ ID NO 154
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 154
ggtcaacttc acattcagac ggcccaggtg                                    30

<210> SEQ ID NO 155
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 155
cacctgggcg atctgaatgt gaagttgacc                                    30

<210> SEQ ID NO 156
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 156
ggtcaacttc acattcagat cgcccaggtg                                    30

<210> SEQ ID NO 157
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 157
aatgtgaagt tgtctaagct aactgagaag                                    30

<210> SEQ ID NO 158
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 158
cttctcagtt agcttagaca acttcacatt                                    30

<210> SEQ ID NO 159
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 159
gtgaagttga ccaagggtac tgagaagcaa                                    30

<210> SEQ ID NO 160
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 160
ttgcttctca gtacccttgg tcaacttcac                                    30

<210> SEQ ID NO 161
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 161
tacctgggca tgacttgtga tggcccttc                                     30

<210> SEQ ID NO 162
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 162
gaagggccca tcacaagtca tgcccaggta                                    30

<210> SEQ ID NO 163
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 163
tcctgtgatg gcgctttcaa gccggatcac                                    30

<210> SEQ ID NO 164
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 164
gtgatccggc ttgaaagcgc catcacagga                                    30

<210> SEQ ID NO 165
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 165
tgtgatggcc cctctaagcc ggatcactac                                    30

<210> SEQ ID NO 166

```
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 166
gtagtgatcc ggcttagagg ggccatcaca                                      30

<210> SEQ ID NO 167
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 167
tgtgatggcc ccttcaagcc gggtcactac                                      30

<210> SEQ ID NO 168
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 168
gtagtgaccc ggcttgaagg ggccatcaca                                      30

<210> SEQ ID NO 169
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 169
tgtgatggcc ccttcaaggc tgatcactac                                      30

<210> SEQ ID NO 170
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 170
gtagtgatca gccttgaagg ggccatcaca                                      30

<210> SEQ ID NO 171
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 171
tgtgatggcc ccttcaagcc ggatgcttac                                      30

<210> SEQ ID NO 172
<211> LENGTH: 30
```

```
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 172
gtaagcatcc ggcttgaagg ggccatcaca                              30

<210> SEQ ID NO 173
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 173
ggccccttca agccggatca cactcgctac                              30

<210> SEQ ID NO 174
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 174
gtagcgagtg tgatccggct tgaaggggcc                              30

<210> SEQ ID NO 175
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 175
ggccccttca agccggatca ctacaaatac                              30

<210> SEQ ID NO 176
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 176
gtatttgtag tgatccggct tgaaggggcc                              30

<210> SEQ ID NO 177
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 177
ggccccttca agccggatca ctacggttac                              30

<210> SEQ ID NO 178
<211> LENGTH: 30
<212> TYPE: DNA
```

-continued

<213> ORGANISM: Artificial Sequence
<220> FEATURE:
<223> OTHER INFORMATION: Oligonucleotide used for site-directed
      mutagenesis of human SAH hydrolases

<400> SEQUENCE: 178
gtaaccgtag tgatccggct tgaaggggcc                              30

<210> SEQ ID NO 179
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 179
cccttcaagc cggatcacta ccgctcttga                              30

<210> SEQ ID NO 180
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 180
tcaagagcgg tagtgatccg gcttgaaggg                              30

<210> SEQ ID NO 181
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 181
cccttcaagc cggatcacta ccgcgcttga                              30

<210> SEQ ID NO 182
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 182
tcaagcgcgg tagtgatccg gcttgaaggg                              30

<210> SEQ ID NO 183
<211> LENGTH: 30
<212> TYPE: DNA
<213> ORGANISM: Artificial Sequence
<220> FEATURE:
<223> OTHER INFORMATION: Oligonucleotide used for site-directed
      mutagenesis of human SAH hydrolases

<400> SEQUENCE: 183
cccttcaagc cggatcacta ccgcttttga                              30

<210> SEQ ID NO 184
<211> LENGTH: 30
<212> TYPE: DNA
<213> ORGANISM: Artificial Sequence
<220> FEATURE:
<223> OTHER INFORMATION: Oligonucleotide used for site-directed
     mutagenesis of human SAH hydrolases

<400> SEQUENCE: 184
tcaaaagcgg tagtgatccg gcttgaaggg                              30

<210> SEQ ID NO 185
<211> LENGTH: 2057
<212> TYPE: DNA
<213> ORGANISM: Mus musculus

<400> SEQUENCE: 185

| | | | | |
|---|---|---|---|---|
| ccagcatgtc | tgataaactg | ccctacaaag | tcgcggacat | cggactggcc gcctggggac | 60 |
| ggaaggctct | ggatatagct | gagaatgaga | tgccaggatt | gatgcgcatg cgggagatgt | 120 |
| actcagcctc | caagccactg | aagggtgctc | gcattgctgg | ctgcctgcac atgaccgtgg | 180 |
| agactgctgt | tctcattgag | actctcgtgg | ccctgggtgc | tgaggtgcgg tggtccagct | 240 |
| gcaacatctt | ctctactcag | gaccatgcag | cggctgccat | tgccaaggct ggcattccag | 300 |
| tgtttgcctg | gaagggcgag | acagatgagg | agtacctgtg | gtgcattgag cagacgctgc | 360 |
| acttcaagga | cggacccctc | aacatgattc | tggatgatgg | tggtgacctt actaacctca | 420 |
| tccacaccaa | atacccacag | cttctgtcag | gcatccgagg | tatctctgag agaccacga | 480 |
| ctggggtcca | caacctctac | aagatgatgt | ccaatgggat | actgaacgtg cctgccatca | 540 |
| atgtcaacga | ttctgtcacc | aagagcaagt | ttgacaacct | ctatggctgc cgggagtccc | 600 |
| tcatagatgg | catcaaacgg | gccacagatg | tgatgattgc | gggcaaggtg gcggtggtgg | 660 |
| caggctatgg | tgatgtgggc | aagggctgtg | cccaggccct | gagggggtttt ggggcccgag | 720 |
| tcatcatcac | cgagatcgac | cccatcaatg | cactgcaagc | tgccatggag ggctatgagg | 780 |
| taaccactat | ggacgaagcc | tgtaaggagg | gcaacatctt | tgtcaccacc acaggctgtg | 840 |
| tggatatcat | ccttggccgg | cactttgagc | agatgaagga | tgacgccatt gtctgtaaca | 900 |
| ttggacactt | cgatgtggag | attgatgtga | agtggctcaa | tgagaacgcg gtggagaaag | 960 |
| tgaacatcaa | gccccaggtg | gaccgctact | ggctaaagaa | tgggcgccgc atcatcttgc | 1020 |
| tggctgaagg | ccgtctggtc | aacctgggtt | gtgccatggg | acaccccagc ttcgtgatga | 1080 |
| gcaactcctt | cacaaaccag | gtgatggcac | agattgagct | gtggacccac ccagataaat | 1140 |
| accctgttgg | ggttcacttc | ctgcctaaga | agctggatga | ggcggtggct gaagcccacc | 1200 |
| tgggcaagct | gaatgtgaag | ctgaccaagc | tgactgagaa | gcaagcccag tacctgggca | 1260 |
| tgccatcaa | cggcccctttc | aagcctgatc | actaccgcta | ctgagagctg gggctgtcct | 1320 |
| tcaccttcca | gctgccatcc | aagttccggg | cccacctctc | gtccccaaga gccaatgtca | 1380 |
| ccaactttgt | ggttagtttg | cctgtgttct | gatccgtccc | cgccccccca tcctcactgt | 1440 |
| ggctggtcac | tccgtctttg | gcctctgctg | caccccctcat | actgttccat atgtggcatc | 1500 |
| gagaacagag | agaggtacct | ggtaggcatc | cacagggac | atgatctcag aagtcttgga | 1560 |
| agtcctgagg | ctggatgttg | ctagtgatgg | tcacaagcca | tgcaccttat cattgatacc | 1620 |
| ctcacttggt | ctttagatct | gtgtgcctgg | tttgcagatc | cattggtttc tcagtccagg | 1680 |
| acccaagaac | gagctccacc | aaagagcagg | aaccctggga | gttttgaaggc ccccgagagc | 1740 |
| tgggcctttt | tactgttggg | cagtctctta | aacctcatga | tactgagttg gtactttttt | 1800 |
| tggtccctat | ttcacaaggg | ttcaggatag | attaaccaag | aaaggacaag tgacagactg | 1860 |
| aaagggggctg | gaaaacaaga | ggaaaggcct | gtcactgtat | agttgatggt tcctgtcaca | 1920 |

```
agcccaggtc acaaacagat taatttgttt tataatgttt atatgctatt tagaatgtta    1980
acaaaggaag gtggataaaa tacagtttct actgcctaaa gaattttggc tctattaaaa    2040
tgtaagtgtg tggctgg                                                   2057
```

<210> SEQ ID NO 186
<211> LENGTH: 2029
<212> TYPE: DNA
<213> ORGANISM: Rattus rattus

<400> SEQUENCE: 186

```
ctcactctag cggacttcgc cagcatggct gataaactgc cctacaaagt cgcggacatt      60
ggactggctg cctggggacg gaaggccctg gacatagctg agaacgagat gccaggtttg     120
atgcgcatgc gggagatgta ctcagcctcc aagccactga agggcgctcg cattgctggc     180
tgcctgcaca tgactgtgga gactgctgtc ctcattgaga ctctcgtggc cctgggtgct     240
gaggtgcggt ggtccagctg caacatcttc tccactcagg accatgcagc ggctgccatt     300
gccaaggctg gcattccagt gtttgcctgg aagggagaga cggatgaaga gtacctgtgg     360
tgcattgagc agacgttgca cttcaaggac ggacccctca acatgattct ggatgatggc     420
ggtgacctta ctaacctcat ccacaccaaa cacccacagc ttctgtcagg catccgaggt     480
atctctgagg agaccacgac tggcgtccac aacctctaca agatgatggc caatgggata     540
ctgaaggtgc ctgccatcaa cgtcaacgat tctgtcacca agagcaagtt tgacaacctc     600
tatggctgcc gggagtccct catagatggc atcaaacggg caacagatgt gatgattgcg     660
ggcaaggtgg cagtggtagc aggctatggt gatgtgggca agggttgtgc ccaggccctg     720
cggggtttcg gggcccgagt catcatcacc gagattgacc ccatcaatgc actgcaagct     780
gccatggagg gctacgaggt aaccaccatg gacgaggcct gtaaggaggg caacatcttt     840
gtgaccacca cgggctgtgt tgatatcatc cttggtcggc actttgaaca gatgaaggat     900
gatgccattg tctgtaacat tggacacttc gacgtggaga ttgatgtgaa gtggctcaat     960
gagaacgctg tggagaaggt gaacatcaag ccccaggtgg accgctactt gctaaagaat    1020
gggcaccgca tcatcttgct ggctgagggc cgtctggtca acctgggttg tgccatgggc    1080
caccccagct tcgtgatgag caactccttc acaaaccagg tgatggcaca gattgagctg    1140
tggacccacc cagacaaata ccccgtgggg gttcacttcc tgcctaagaa gctggatgag    1200
gcagtggctc aagcccacct gggcaagctg aacgtcaagc tgaccaagct gactgagaag    1260
caggctcagt acctgggcat gcccattaac ggccccttca gcctgatca ctaccgctac    1320 tgagagctgg gactgccctt caccttccag ctgccatcct tgttccaggc cctacctctc    1380
gttcccaaga gcaaatgtca ccaactttgc agttacttct ccggtgttct gctccctccc    1440
ccggccctca tccacactgt gactggtctt tctgtctttg gcttctgctg tacccctcat    1500
actgttccct atgtggcata gagaacagag aggtacctgg gaggcatcca cagggatct    1560 gagctcttgg aaggtctgag gctggatgtt gctggtggtc acaagcccat gcaccttact    1620
atccaaactc tcgcttggtc tttagatccg tgtgcttggt ttacagacca atggtttctc    1680
ggcccaggac ccaagaagga gctctaccat ggggдаagga accactggag tttgaaggct    1740
cctgagagct tggccttttt actgttgggc tgtctcttaa acctcctaat actgagтттgg    1800 ctacttttgg tccctatttc acaagggtta ggacagatta accaagaaag gacaagtgac    1860
agagactgaa aggggctgga aaaacaaata gggaaaggcc tgtcacctac ggtataattg    1920
```

-continued

| | |
|---|---|
| atggttccta tcacaagcct ggatcacaaa cagattaatt tgttctatgt ttatatactg | 1980 |
| tttagaatgt taacacagga aggtggataa aatacagttt ctagtgcct | 2029 |

<210> SEQ ID NO 187
<211> LENGTH: 2211
<212> TYPE: DNA
<213> ORGANISM: Homo sapiens

<400> SEQUENCE: 187

| | |
|---|---|
| ctgaggccca gccccttcg cccgtttcca tcacgagtgc cgccagcatg tctgacaaac | 60 |
| tgccctacaa agtcgccgac atcggcctgg ctgcctgggg acgcaaggcc ctggacattg | 120 |
| ctgagaacga gatgccgggc ctgatgcgta tgcgggagcg gtactcggcc tccaagccac | 180 |
| tgaagggcgc ccgcatcgct ggctgcctgc acatgaccgt ggagacggcc gtcctcattg | 240 |
| agaccctcgt cacccctggg gctgaggtgc agtggtccag ctgcaacatc ttctccaccc | 300 |
| agaaccatgc ggcggctgcc attgccaagg ctggcattcc ggtgtatgcc tggaagggcg | 360 |
| aaacggacga ggagtacctg tggtgcattg agcagaccct gtacttcaag gacgggcccc | 420 |
| tcaacatgat tctggacgac gggggcgacc tcaccaacct catccacacc aagtacccgc | 480 |
| agcttctgcc aggcatccga ggcatctctg aggagaccac gactggggtc cacaacctct | 540 |
| acaagatgat ggccaatggg atcctcaagg tgcctgccat caatgtcaat gactccgtca | 600 |
| ccaagagcaa gtttgacaac ctctatggct gccgggagtc cctcatagat ggcatcaagc | 660 |
| gggccacaga tgtgatgatt gccggcaagg tagcggtggt agcaggctat ggtgatgtgg | 720 |
| gcaagggctg tgcccaggcc ctgcggggtt tcggagcccg cgtcatcatc accgagattg | 780 |
| acccatcaa cgcactgcag gctgccatgg agggctatga ggtgaccacc atggatgagg | 840 |
| cctgtcagga gggcaacatc tttgtcacca ccacaggctg tattgacatc atccttggcc | 900 |
| ggtaggtgcc agatgggggg tcccggggag tgagggagga gggcagagtt gggacagctt | 960 |
| tctgtccctg acaatctccc acggtcttgg gctgcctgac aggcacttg agcagatgaa | 1020 |
| ggatgatgcc attgtgtgta acattggaca ctttgacgtg gagatcgatg tcaagtggct | 1080 |
| caacgagaac gccgtggaga aggtgaacat caagccgcag gtggaccggt atcggttgaa | 1140 |
| gaatgggcgc cgcatcatcc tgctggccga gggtcggctg gtcaacctgg ttgtgccat | 1200 |
| ggccaccccc agcttcgtga tgagtaactc cttcaccaac caggtgatgg cgcagatcga | 1260 |
| gctgtggacc catccagaca agtaccccgt tgggttcat ttcctgccca agaagctgga | 1320 |
| tgaggcagtg gctgaagccc acctgggcaa gctgaatgtg aagttgacca agctaactga | 1380 |
| gaagcaagcc cagtacctgg gcatgtcctg tgatggcccc ttcaagccgg atcactaccg | 1440 |
| ctactgagag ccaggtctgc gtttcaccct ccagctgctg tccttgccca ggccccacct | 1500 |
| ctcctcccta agagctaatg gcaccaactt tgtgattggt ttgtcagtgt cccccatcga | 1560 |
| ctctctgggg ctgatcactt agtttttggc ctctgctgca gccgtcatac tgttccaaat | 1620 |
| gtggcagcgg gaacagagta ccctcttcaa gccccggtca tgatggaggt cccagccaca | 1680 |
| gggaaccatg agctcagtgg tcttggaaca gctcactaag tcagtccttc cttagcctgg | 1740 |
| aagtcagtag tggagtcaca aagcccatgt gttttgccat ctaggccttc acctggtctg | 1800 |
| tggacttata cctgtgtgct tggtttacag gtccagtggt tcttcagccc atgacagatg | 1860 |
| agaaggggct atattgaagg gcaaagagga actgttgttt gaattttcct gagagcctgg | 1920 |
| cttagtgctg ggccttctct taaacctcat tacaatgagg ttagtacttt tagtccctgt | 1980 |
| tttacagggg ttagaataga ctgttaaggg gcaactgaga aagaacagag aagtgacagc | 2040 |

| | |
|---|---|
| tagggggttga gagggggccag aaaaacatga atgcaggcag atttcgtgaa atctgccacc | 2100 |
| actttataac cagatggttc ctttcacaac cctgggtcaa aaagagaata atttggccta | 2160 |
| taatgttaaa agaaagcagg aaggtgggta aataaaaatc ttggtgcctg g | 2211 |

<210> SEQ ID NO 188
<211> LENGTH: 2084
<212> TYPE: DNA
<213> ORGANISM: Homo sapiens

<400> SEQUENCE: 188

| | |
|---|---|
| ggcccagccc ccttcgcccg tttccatcac gagtgccgcc agcatgtctg acaaactgcc | 60 |
| ctacaaagtc gccgacatcg gcctggctgc ctggggacgc aaggccctgg acattgctga | 120 |
| gaacgagatg ccgggcctga tgcgtatgcg ggagcggtac tcggcctcca agccactgaa | 180 |
| gggcgcccgc atcgctggct gcctgcacat gaccgtggag acggccgtcc tcattgagac | 240 |
| cctcgtcacc ctgggtgctg aggtgcagtg gtccagctgc aacatcttct ccacccagga | 300 |
| ccatgcggcg gctgccattg ccaaggctgg cattccggtg tatgcctgga agggcgaaac | 360 |
| ggacgaggag tacctgtggt gcattgagca gaccctgtac ttcaaggacg ggcccctcaa | 420 |
| catgattctg gacgacgggg cgacctcac caacctcatc cacaccaagt acccgcagct | 480 |
| tctgccaggc atccgaggca tctctgagga gaccacgact ggggtccaca acctctacaa | 540 |
| gatgatggcc aatgggatcc tcaaggtgcc tgccatcaat gtcaatgact ccgtcaccaa | 600 |
| gagcaagttt gacaacctct atggctgccg ggagtccctc atagatggca tcaagcgggc | 660 |
| cacagatgtg atgattgccg gcaaggtagc ggtggtagca ggctatgtg atgtgggcaa | 720 |
| gggctgtgcc caggccctgc gggggtttcgg agcccgcgtc atcatcaccg agattgaccc | 780 |
| catcaacgca ctgcaggctg ccatggaggg ctatgaggtg accaccatgg atgaggcctg | 840 |
| tcaggagggc aacatcttg tcaccaccac aggctgtatt gacatcatcc ttggccggca | 900 |
| ctttgagcag atgaaggatg atgccattgt gtgtaacatt ggacactttg acgtggagat | 960 |
| cgatgtcaag tggctcaacg agaacgccgt ggagaaggtg aacatcaagc cgcaggtgga | 1020 |
| ccggtatcgg ttgaagaatg gcgccgcat catcctgctg gccgagggtc ggctggtcaa | 1080 |
| cctgggttgt gccatgggcc accccagctt cgtgatgagt aactccttca ccaaccaggt | 1140 |
| gatggcgcag atcgagctgt ggacccatcc agacaagtac cccgttgggg ttcatttcct | 1200 |
| gcccaagaag ctggatgagg cagtggctga agcccacctg gcaagctga atgtgaagtt | 1260 |
| gaccaagcta actgagaagc aagcccagta cctgggcatg tcctgtgatg ccccttcaa | 1320 |
| gccggatcac taccgctact gagagccagg tctgcgtttc accctccagc tgctgtcctt | 1380 |
| gcccaggccc cacctctcct ccctaagagc taatggcacc aactttgtga ctggttttgtc | 1440 |
| agtgtccccc atcgactctc tggggctgat cacttagttt ttggcctctg ctgcagccgt | 1500 |
| catactgttc caaatgtggc agcgggaaca gagtacccctc ttcaagcccc ggtcatgatg | 1560 |
| gaggtcccag ccacagggaa ccatgagctc agtggtcttg aacagctca ctaagtcagt | 1620 |
| ccttccttag cctggaagcc agtagtggag tcacaaagcc catgtgttt gccatctagg | 1680 |
| ccttcacctg gtctgtggac ttatacctgt gtgcttggtt tacaggtcca gtggttcttc | 1740 |
| agcccatgac agatgagaag gggctatatt gaagggcaaa gaggaactgt tgtttgaatt | 1800 |
| ttcctgagag cctggcttag tgctgggcct tctcttaaac ctcattacaa tgaggttagt | 1860 |
| acttttagtc cctgtttttac aggggttaga atagactgtt aaggggcaac tgagaaagaa | 1920 |

```
cagagaagtg acagctaggg gttgagaggg gccagaaaaa catgaatgca ggcagatttc    1980
gtgaaatctg ccaccacttt ataaccagat ggttcctttc acaaccctgg gtcaaaaaga    2040
gaataatttg gcctataatg ttaaaagaaa gcaggaaggt gggt                     2084
```